US012611519B2

(12) United States Patent
Hughett, Sr. et al.

(10) Patent No.: US 12,611,519 B2
(45) Date of Patent: Apr. 28, 2026

(54) INTERMITTENT-CATHETER ASSEMBLY AND METHODS THEREOF

(71) Applicant: C. R. Bard, Inc., Franklin Lakes, NJ (US)

(72) Inventors: James David Hughett, Sr., Monroe, GA (US); Pooja Kulkarni, Pune (IN)

(73) Assignee: C. R. Bard, Inc., Franklin Lakes, NJ (US)

( * ) Notice: Subject to any disclaimer, the term of this patent is extended or adjusted under 35 U.S.C. 154(b) by 341 days.

(21) Appl. No.: 18/025,875

(22) PCT Filed: Sep. 10, 2021

(86) PCT No.: PCT/US2021/049867
§ 371 (c)(1),
(2) Date: Mar. 10, 2023

(87) PCT Pub. No.: WO2022/056263
PCT Pub. Date: Mar. 17, 2022

(65) Prior Publication Data
US 2023/0364379 A1 Nov. 16, 2023

Related U.S. Application Data

(60) Provisional application No. 63/077,469, filed on Sep. 11, 2020.

(51) Int. Cl.
A61M 25/00 (2006.01)
(52) U.S. Cl.
CPC .............................. A61M 25/0017 (2013.01)
(58) Field of Classification Search
CPC ............ A61M 25/002; A61M 25/0017; A61M 2025/0175; A61M 25/0111;
(Continued)

(56) References Cited

U.S. PATENT DOCUMENTS

| | | |
|---|---|---|
| 426,931 A | 4/1890 | Flower |
| 734,498 A | 7/1903 | Bachler |

(Continued)

FOREIGN PATENT DOCUMENTS

| | | |
|---|---|---|
| AU | 2016283336 A1 | 12/2017 |
| AU | 2014362360 B2 | 1/2020 |

(Continued)

OTHER PUBLICATIONS

EP 24164460.8 filed Mar. 19, 2024 Extended European Search Report dated Jun. 19, 2024.

(Continued)

*Primary Examiner* — Adam Marcetich
(74) *Attorney, Agent, or Firm* — Rutan & Tucker LLP

(57) ABSTRACT

An intermittent-catheter assembly (100) includes an intermittent catheter and a catheter housing (102). The intermittent catheter includes a funnel and a catheter tube fluidly coupled to the funnel. The catheter housing (102) includes the intermittent catheter disposed in the catheter housing while in a packaged state of the intermittent-catheter assembly. The catheter housing includes an inner sleeve (104) and an outer sleeve (102). The inner sleeve (104) includes a longitudinal cavity containing a majority of the intermittent catheter in the packaged state of the intermittent-catheter assembly. The outer sleeve (106) is slidably disposed over the inner sleeve (104). The catheter housing (102) is configured to expose the intermittent catheter for removal from the catheter housing (102) when the outer sleeve (106) is grasped and slid toward an exposed end of the inner sleeve (104) in opposition to a force applied to the exposed end of the inner sleeve (104).

11 Claims, 25 Drawing Sheets

(58) Field of Classification Search
CPC .. A61M 2025/0004; A61M 2210/1089; A61M
25/00; A61M 25/0136; A61M 2202/0496;
A61M 2210/1085; A61M 2210/1096;
A61M 27/008; B65D 47/141; B65D
81/22; B65D 43/162; B65D 55/16; B65D
77/04; B65D 21/086; B65D 83/0418;
B65D 90/62; B65D 90/626; B65D
5/6617; B65D 5/6688; B65D 43/20;
B65D 11/12; B25H 3/003
See application file for complete search history.

(56) References Cited

U.S. PATENT DOCUMENTS

| | | | |
|---|---|---|---|
| 1,131,865 A | 3/1915 | Putnam et al. | |
| 1,235,142 A | 7/1917 | Ichilian | |
| 1,304,396 A | 5/1919 | Smith | |
| 1,643,289 A | 9/1927 | Peglay | |
| 1,661,494 A | 3/1928 | Nielsen | |
| 1,876,229 A | 9/1932 | Oliver et al. | |
| 1,888,349 A | 11/1932 | Jacoby | |
| 1,978,497 A * | 10/1934 | Lind | A24F 15/12 |
| | | | 206/265 |
| 2,043,630 A | 6/1936 | Raiche | |
| 2,213,210 A | 9/1940 | Egbert | |
| 2,228,992 A | 1/1941 | Fry | |
| 2,230,226 A | 2/1941 | Auzin | |
| 2,248,934 A | 7/1941 | Auzin | |
| 2,262,749 A * | 11/1941 | Berwald | B65D 5/5092 |
| | | | 229/162.1 |
| 2,285,502 A | 6/1942 | Dreyfus | |
| 2,308,484 A | 1/1943 | Auzin et al. | |
| 2,314,262 A | 3/1943 | Winder | |
| 2,320,157 A | 5/1943 | Raiche | |
| 2,322,858 A | 6/1943 | Limbert et al. | |
| 2,330,399 A | 9/1943 | Winder | |
| 2,330,400 A | 9/1943 | Winder | |
| 2,389,831 A | 11/1945 | Welsh | |
| 2,390,070 A | 12/1945 | Auzin | |
| 2,481,488 A | 9/1949 | Auzin | |
| 2,494,393 A | 1/1950 | Lamson | |
| 2,610,626 A | 9/1952 | Edwards | |
| 2,638,093 A | 5/1953 | Kulick | |
| 2,648,463 A | 8/1953 | Robert | |
| 2,649,619 A | 8/1953 | Killian | |
| 2,649,854 A | 8/1953 | Salm | |
| 2,690,595 A | 10/1954 | Raiche | |
| 2,712,161 A | 7/1955 | Moss | |
| 2,856,932 A | 10/1958 | Griffitts | |
| 2,912,981 A | 11/1959 | Keough | |
| 2,919,697 A | 1/1960 | Kim | |
| 3,035,691 A | 5/1962 | Kai et al. | |
| 3,044,468 A | 7/1962 | Birtwell | |
| 3,053,257 A | 9/1962 | Birtwell | |
| 3,076,464 A | 2/1963 | Rosenberg | |
| 3,169,527 A | 2/1965 | Sheridan | |
| 3,173,566 A | 3/1965 | Talbert | |
| 3,211,151 A | 10/1965 | Foderick et al. | |
| 3,246,075 A | 4/1966 | Dansard | |
| 3,249,285 A | 5/1966 | Franz et al. | |
| 3,304,353 A | 2/1967 | Harautuneian | |
| 3,344,791 A | 10/1967 | Foderick | |
| 3,345,988 A | 10/1967 | Vitello | |
| 3,394,704 A | 7/1968 | Dery | |
| 3,394,705 A | 7/1968 | Abramson | |
| 3,403,682 A | 10/1968 | McDonell | |
| 3,409,016 A | 11/1968 | Foley | |
| 3,434,869 A | 3/1969 | Davidson | |
| 3,463,141 A | 8/1969 | Mozolf | |
| 3,478,743 A | 11/1969 | Ericson | |
| 3,503,400 A | 3/1970 | Osthagen | |
| 3,508,959 A | 4/1970 | Krahnke | |
| 3,509,884 A | 5/1970 | Bell | |
| 3,520,305 A | 7/1970 | Davis | |
| 3,539,674 A | 11/1970 | Dereniuk et al. | |
| 3,544,668 A | 12/1970 | Dereniuk | |
| 3,548,805 A | 12/1970 | Datsenko | |
| 3,556,294 A | 1/1971 | Walck et al. | |
| 3,556,874 A | 1/1971 | McClain | |
| 3,566,874 A | 3/1971 | Shepherd et al. | |
| 3,593,713 A | 7/1971 | Bogoff et al. | |
| 3,598,127 A | 8/1971 | Wepsic | |
| 3,606,889 A | 9/1971 | Arblaster | |
| 3,642,004 A | 2/1972 | Osthagen et al. | |
| 3,646,929 A | 3/1972 | Bonnar | |
| 3,648,704 A | 3/1972 | Jackson | |
| 3,648,891 A * | 3/1972 | Katz | B65D 11/12 |
| | | | 221/268 |
| 3,651,615 A | 3/1972 | Bohner et al. | |
| 3,683,928 A | 8/1972 | Kuntz | |
| 3,695,921 A | 10/1972 | Shepherd et al. | |
| 3,699,956 A | 10/1972 | Kitrilakis et al. | |
| 3,699,964 A | 10/1972 | Ericson | |
| 3,708,324 A | 1/1973 | Stebleton | |
| 3,726,281 A | 4/1973 | Norton et al. | |
| 3,739,783 A | 6/1973 | Broerman | |
| 3,761,013 A | 9/1973 | Schuster | |
| 3,762,399 A | 10/1973 | Riedell | |
| 3,768,102 A | 10/1973 | Kwan-Gett et al. | |
| 3,788,324 A | 1/1974 | Lim | |
| 3,794,042 A | 2/1974 | De Klotz et al. | |
| 3,797,478 A | 3/1974 | Walsh et al. | |
| 3,802,987 A | 4/1974 | Noll | |
| 3,835,992 A | 9/1974 | Adams, IV | |
| 3,838,728 A | 10/1974 | Voegele | |
| 3,841,304 A | 10/1974 | Jones | |
| 3,854,483 A | 12/1974 | Powers | |
| 3,861,395 A | 1/1975 | Taniguchi | |
| 3,875,937 A | 4/1975 | Schmitt et al. | |
| 3,879,516 A | 4/1975 | Wolvek | |
| 3,882,220 A | 5/1975 | Ryder | |
| 3,889,685 A | 6/1975 | Miller, Jr. et al. | |
| 3,894,540 A | 7/1975 | Bonner, Jr. | |
| 3,898,993 A | 8/1975 | Taniguchi | |
| 3,924,634 A | 12/1975 | Taylor et al. | |
| 3,926,309 A | 12/1975 | Center | |
| 3,926,705 A | 12/1975 | Todd | |
| 3,930,580 A | 1/1976 | Bazell et al. | |
| 3,934,721 A | 1/1976 | Juster et al. | |
| 3,962,519 A | 6/1976 | Rusch et al. | |
| 3,967,728 A | 7/1976 | Gordon et al. | |
| 3,981,299 A | 9/1976 | Murray | |
| 3,983,879 A | 10/1976 | Todd | |
| 4,026,296 A | 5/1977 | Stoy et al. | |
| 4,029,104 A | 6/1977 | Kerber | |
| 4,051,849 A | 10/1977 | Poncy et al. | |
| 4,055,682 A | 10/1977 | Merrill | |
| 4,062,363 A | 12/1977 | Bonner, Jr. | |
| 4,069,359 A | 1/1978 | DeMarse et al. | |
| 4,091,922 A | 5/1978 | Egler | |
| 4,119,094 A | 10/1978 | Micklus et al. | |
| 4,120,715 A | 10/1978 | Ockwell et al. | |
| 4,133,303 A | 1/1979 | Patel | |
| 4,140,127 A | 2/1979 | Cianci et al. | |
| 4,149,539 A | 4/1979 | Cianci | |
| 4,168,699 A | 9/1979 | Hauser | |
| 4,170,996 A | 10/1979 | Wu | |
| 4,186,745 A | 2/1980 | Lewis et al. | |
| 4,187,851 A | 2/1980 | Hauser | |
| 4,196,731 A | 4/1980 | Laurin et al. | |
| 4,198,983 A | 4/1980 | Becker et al. | |
| 4,198,984 A | 4/1980 | Taylor | |
| 4,209,010 A | 6/1980 | Ward et al. | |
| 4,225,371 A | 9/1980 | Taylor et al. | |
| 4,230,115 A | 10/1980 | Walz, Jr. et al. | |
| 4,245,639 A | 1/1981 | La Rosa | |
| 4,246,909 A | 1/1981 | Wu et al. | |
| 4,249,535 A | 2/1981 | Hargest, III | |
| 4,252,760 A | 2/1981 | Foster et al. | |
| 4,265,848 A | 5/1981 | Rusch | |
| 4,266,999 A | 5/1981 | Baier | |
| 4,269,310 A | 5/1981 | Uson | |
| 4,284,459 A | 8/1981 | Patel et al. | |
| 4,287,227 A | 9/1981 | Kamada et al. | |

(56)                    References Cited

U.S. PATENT DOCUMENTS

| | | | |
|---|---|---|---|
| 4,306,557 A | 12/1981 | North |
| 4,311,146 A | 1/1982 | Wonder |
| 4,311,659 A | 1/1982 | Rey et al. |
| 4,318,406 A | 3/1982 | McLeod |
| 4,318,947 A | 3/1982 | Joung |
| 4,341,817 A | 7/1982 | Tozier et al. |
| 4,343,788 A | 8/1982 | Mustacich et al. |
| 4,350,161 A | 9/1982 | Davis, Jr. |
| 4,351,333 A | 9/1982 | Lazarus et al. |
| 4,366,901 A | 1/1983 | Short |
| 4,367,732 A | 1/1983 | Poulsen et al. |
| 4,378,018 A | 3/1983 | Alexander et al. |
| 4,378,796 A | 4/1983 | Milhaud |
| 4,379,506 A | 4/1983 | Davidson |
| 4,381,008 A | 4/1983 | Thomas et al. |
| 4,381,380 A | 4/1983 | LeVeen et al. |
| 4,392,848 A | 7/1983 | Lucas et al. |
| 4,395,806 A | 8/1983 | Wonder et al. |
| 4,411,648 A | 10/1983 | Davis et al. |
| 4,419,097 A | 12/1983 | Rowland |
| 4,428,365 A | 1/1984 | Hakky |
| 4,449,971 A | 5/1984 | Cawood |
| 4,457,299 A | 7/1984 | Cornwell |
| 4,472,226 A | 9/1984 | Redinger et al. |
| 4,475,910 A | 10/1984 | Conway et al. |
| 4,477,325 A | 10/1984 | Osburn |
| 4,479,795 A | 10/1984 | Mustacich et al. |
| 4,486,504 A | 12/1984 | Chung |
| 4,515,593 A | 5/1985 | Norton |
| 4,517,971 A | 5/1985 | Sorbonne |
| 4,534,768 A | 8/1985 | Osburn et al. |
| 4,539,234 A | 9/1985 | Sakamoto et al. |
| 4,540,409 A | 9/1985 | Nystrom et al. |
| 4,552,269 A | 11/1985 | Chang |
| 4,553,533 A | 11/1985 | Leighton |
| 4,560,382 A | 12/1985 | Sono et al. |
| 4,563,184 A | 1/1986 | Korol |
| 4,568,340 A | 2/1986 | Giacalone |
| 4,571,239 A | 2/1986 | Heyman |
| 4,571,240 A | 2/1986 | Samson et al. |
| 4,571,241 A | 2/1986 | Christopher |
| 4,576,599 A | 3/1986 | Lipner |
| 4,581,026 A | 4/1986 | Schneider |
| 4,581,028 A | 4/1986 | Fox, Jr. et al. |
| 4,582,762 A | 4/1986 | Onohara et al. |
| 4,585,666 A | 4/1986 | Lambert |
| 4,586,974 A | 5/1986 | Nystrom et al. |
| 4,589,874 A | 5/1986 | Riedel et al. |
| 4,592,920 A | 6/1986 | Murtfeldt |
| 4,597,765 A | 7/1986 | Klatt |
| 4,597,931 A | 7/1986 | Watanabe et al. |
| 4,601,713 A | 7/1986 | Fuqua |
| 4,603,152 A | 7/1986 | Laurin et al. |
| 4,607,746 A | 8/1986 | Stinnette |
| 4,610,670 A | 9/1986 | Spencer |
| 4,612,337 A | 9/1986 | Fox, Jr. et al. |
| 4,613,324 A | 9/1986 | Ghajar |
| 4,615,692 A | 10/1986 | Giacalone et al. |
| 4,615,697 A | 10/1986 | Robinson |
| 4,619,642 A | 10/1986 | Spencer |
| 4,622,033 A | 11/1986 | Taniguchi |
| 4,623,329 A | 11/1986 | Drobish et al. |
| 4,626,250 A | 12/1986 | Schneider |
| 4,627,844 A | 12/1986 | Schmitt |
| 4,634,433 A | 1/1987 | Osborne |
| 4,637,907 A | 1/1987 | Hegel et al. |
| 4,638,790 A | 1/1987 | Conway et al. |
| 4,639,246 A | 1/1987 | Dudley |
| 4,640,688 A | 2/1987 | Hauser |
| 4,652,259 A | 3/1987 | D'Neil |
| 4,664,657 A | 5/1987 | Williamitis et al. |
| 4,673,401 A | 6/1987 | Jensen et al. |
| 4,677,143 A | 6/1987 | Laurin et al. |
| 4,681,572 A | 7/1987 | Tokarz et al. |
| 4,685,913 A | 8/1987 | Austin |
| 4,686,124 A | 8/1987 | Onohara et al. |
| 4,687,470 A | 8/1987 | Okada |
| 4,692,152 A | 9/1987 | Emde |
| 4,692,154 A | 9/1987 | Singery et al. |
| 4,696,672 A | 9/1987 | Mochizuki et al. |
| 4,699,616 A | 10/1987 | Nowak et al. |
| 4,704,102 A | 11/1987 | Guthery |
| 4,710,169 A | 12/1987 | Christopher |
| 4,710,181 A | 12/1987 | Fuqua |
| 4,723,946 A | 2/1988 | Kay |
| 4,731,064 A | 3/1988 | Heyden |
| 4,737,219 A | 4/1988 | Taller et al. |
| 4,738,667 A | 4/1988 | Galloway |
| 4,739,768 A | 4/1988 | Engelson |
| 4,747,845 A | 5/1988 | Korol |
| 4,754,877 A | 7/1988 | Johansson et al. |
| 4,759,753 A | 7/1988 | Schneider et al. |
| 4,762,128 A | 8/1988 | Rosenbluth |
| 4,769,013 A | 9/1988 | Lorenz et al. |
| 4,769,099 A | 9/1988 | Therriault et al. |
| 4,772,473 A | 9/1988 | Patel et al. |
| 4,773,901 A | 9/1988 | Norton |
| 4,775,371 A | 10/1988 | Mueller, Jr. |
| 4,784,651 A | 11/1988 | Hickey et al. |
| 4,790,834 A | 12/1988 | Austin |
| 4,790,835 A | 12/1988 | Elias |
| D299,865 S | 2/1989 | Kamstrup-Larsen et al. |
| 4,810,247 A | 3/1989 | Glassman |
| 4,811,847 A | 3/1989 | Reif et al. |
| 4,813,935 A | 3/1989 | Haber et al. |
| 4,820,270 A | 4/1989 | Hardcastle et al. |
| 4,820,289 A | 4/1989 | Coury et al. |
| 4,820,291 A | 4/1989 | Terauchi et al. |
| 4,820,292 A | 4/1989 | Korol et al. |
| 4,834,721 A | 5/1989 | Onohara et al. |
| 4,838,876 A | 6/1989 | Wong et al. |
| 4,846,784 A | 7/1989 | Haber |
| 4,846,909 A | 7/1989 | Klug et al. |
| 4,850,969 A | 7/1989 | Jackson |
| 4,861,337 A | 8/1989 | George |
| 4,863,424 A | 9/1989 | Blake, III et al. |
| 4,863,444 A | 9/1989 | Blomer |
| 4,863,449 A | 9/1989 | Therriault et al. |
| 4,867,748 A | 9/1989 | Samuelsen |
| 4,874,373 A | 10/1989 | Luther et al. |
| 4,876,109 A | 10/1989 | Mayer et al. |
| 4,885,049 A | 12/1989 | Johannesson |
| 4,886,508 A | 12/1989 | Washington |
| 4,888,005 A | 12/1989 | Dingeman et al. |
| 4,893,623 A | 1/1990 | Rosenbluth |
| 4,894,059 A | 1/1990 | Larsen et al. |
| 4,902,503 A | 2/1990 | Umemura et al. |
| 4,904,260 A | 2/1990 | Ray et al. |
| 4,917,113 A | 4/1990 | Conway et al. |
| 4,917,686 A | 4/1990 | Bayston et al. |
| RE33,206 E | 5/1990 | Conway et al. |
| 4,923,450 A | 5/1990 | Maeda et al. |
| 4,925,668 A | 5/1990 | Khan et al. |
| 4,930,522 A | 6/1990 | Busnel et al. |
| 4,931,056 A | 6/1990 | Ghajar et al. |
| 4,932,938 A | 6/1990 | Goldberg et al. |
| 4,932,948 A | 6/1990 | Kernes et al. |
| 4,934,999 A | 6/1990 | Bader |
| 4,935,260 A | 6/1990 | Shlenker |
| 4,950,256 A | 8/1990 | Luther et al. |
| 4,957,487 A | 9/1990 | Gerow |
| 4,963,137 A | 10/1990 | Heyden |
| 4,968,294 A | 11/1990 | Salama |
| 4,968,507 A | 11/1990 | Zentner et al. |
| 4,976,703 A | 12/1990 | Franetzki et al. |
| 4,981,471 A | 1/1991 | Quinn et al. |
| 4,994,047 A | 2/1991 | Walker et al. |
| 4,997,426 A | 3/1991 | Dingeman et al. |
| 5,004,454 A | 4/1991 | Beyar et al. |
| 5,007,897 A | 4/1991 | Kalb et al. |
| 5,013,306 A | 5/1991 | Solomon et al. |
| 5,013,717 A | 5/1991 | Solomon et al. |
| 5,019,096 A | 5/1991 | Fox, Jr. et al. |
| 5,019,378 A | 5/1991 | Allen |

(56)                    References Cited

U.S. PATENT DOCUMENTS

| | | | |
|---|---|---|---|
| 5,019,601 A | 5/1991 | Allen | |
| 5,045,078 A | 9/1991 | Asta | |
| 5,059,190 A | 10/1991 | Novak | |
| 5,071,406 A | 12/1991 | Jang | |
| 5,077,352 A | 12/1991 | Elton | |
| 5,078,707 A | 1/1992 | Peter Klug | |
| 5,082,006 A | 1/1992 | Jonasson | |
| 5,084,037 A | 1/1992 | Barnett | |
| 5,087,252 A | 2/1992 | Denard | |
| 5,088,980 A | 2/1992 | Leighton | |
| 5,089,205 A | 2/1992 | Huang et al. | |
| 5,090,424 A | 2/1992 | Simon et al. | |
| 5,098,379 A | 3/1992 | Conway et al. | |
| 5,100,396 A | 3/1992 | Zamierowski | |
| 5,102,401 A | 4/1992 | Lambert et al. | |
| 5,102,405 A | 4/1992 | Conway et al. | |
| 5,109,378 A | 4/1992 | Proctor et al. | |
| 5,109,601 A | 5/1992 | McBride | |
| 5,112,306 A | 5/1992 | Burton et al. | |
| 5,114,398 A | 5/1992 | Trick et al. | |
| 5,118,007 A * | 6/1992 | Lewis | B65D 83/049 |
| | | | 206/536 |
| 5,128,088 A | 7/1992 | Shimomura et al. | |
| 5,131,906 A | 7/1992 | Chen | |
| 5,137,671 A | 8/1992 | Conway et al. | |
| 5,140,999 A | 8/1992 | Ardito | |
| 5,147,341 A | 9/1992 | Starke et al. | |
| 5,165,952 A | 11/1992 | Solomon et al. | |
| 5,174,290 A | 12/1992 | Fiddian-Green | |
| 5,176,666 A | 1/1993 | Conway et al. | |
| 5,179,174 A | 1/1993 | Elton | |
| 5,180,591 A | 1/1993 | Magruder et al. | |
| 5,186,172 A | 2/1993 | Fiddian-Green | |
| 5,188,596 A | 2/1993 | Condon et al. | |
| 5,197,957 A | 3/1993 | Wendler | |
| 5,201,724 A | 4/1993 | Hukins et al. | |
| 5,209,726 A | 5/1993 | Goosen | |
| 5,209,728 A | 5/1993 | Kraus et al. | |
| 5,211,640 A | 5/1993 | Wendler | |
| 5,224,953 A | 7/1993 | Morgentaler | |
| 5,226,530 A | 7/1993 | Golden | |
| 5,234,411 A | 8/1993 | Vaillancourt et al. | |
| 5,236,422 A | 8/1993 | Eplett, Jr. | |
| 5,242,391 A | 9/1993 | Place et al. | |
| 5,242,398 A | 9/1993 | Knoll et al. | |
| 5,242,428 A | 9/1993 | Palestrant | |
| 5,261,896 A | 11/1993 | Conway et al. | |
| 5,263,947 A | 11/1993 | Kay | |
| 5,269,755 A | 12/1993 | Bodicky | |
| 5,269,770 A | 12/1993 | Conway et al. | |
| 5,270,358 A | 12/1993 | Asmus | |
| 5,282,795 A | 2/1994 | Finney | |
| 5,290,306 A | 3/1994 | Trotta et al. | |
| 5,306,226 A | 4/1994 | Salama | |
| 5,334,175 A | 8/1994 | Conway et al. | |
| 5,336,211 A | 8/1994 | Metz | |
| 5,346,483 A | 9/1994 | Thaxton, Sr. | |
| 5,348,536 A | 9/1994 | Young et al. | |
| 5,352,182 A | 10/1994 | Kalb et al. | |
| 5,354,132 A | 10/1994 | Young et al. | |
| 5,360,402 A | 11/1994 | Conway et al. | |
| 5,360,414 A | 11/1994 | Yarger | |
| 5,366,449 A | 11/1994 | Gilberg | |
| 5,368,575 A | 11/1994 | Chang | |
| 5,370,899 A | 12/1994 | Conway et al. | |
| 5,376,085 A | 12/1994 | Conway et al. | |
| 5,380,312 A | 1/1995 | Goulter | |
| 5,395,333 A | 3/1995 | Brill | |
| 5,409,014 A | 4/1995 | Napoli et al. | |
| 5,409,495 A | 4/1995 | Osborn | |
| 5,415,165 A | 5/1995 | Fiddian-Green | |
| 5,415,635 A | 5/1995 | Bagaoisan et al. | |
| 5,417,226 A | 5/1995 | Juma | |
| 5,417,666 A | 5/1995 | Coulter | |
| 5,423,784 A | 6/1995 | Metz | |
| 5,433,705 A | 7/1995 | Giebel et al. | |
| 5,433,713 A | 7/1995 | Trotta | |
| 5,445,626 A | 8/1995 | Gigante et al. | |
| 5,447,231 A | 9/1995 | Kastenhofer | |
| 5,451,424 A | 9/1995 | Solomon et al. | |
| 5,454,798 A | 10/1995 | Kubalak et al. | |
| 5,456,251 A | 10/1995 | Fiddian-Green | |
| 5,464,650 A | 11/1995 | Berg et al. | |
| 5,466,229 A | 11/1995 | Elson et al. | |
| 5,476,434 A | 12/1995 | Kalb et al. | |
| 5,479,945 A | 1/1996 | Simon | |
| 5,482,740 A | 1/1996 | Conway et al. | |
| 5,483,976 A | 1/1996 | McLaughlin et al. | |
| 5,497,601 A | 3/1996 | Gonzalez | |
| 5,501,669 A | 3/1996 | Conway et al. | |
| 5,509,427 A | 4/1996 | Simon et al. | |
| 5,509,889 A | 4/1996 | Kalb et al. | |
| 5,509,899 A | 4/1996 | Fan et al. | |
| 5,513,659 A | 5/1996 | Buuck et al. | |
| 5,513,660 A | 5/1996 | Simon et al. | |
| 5,514,112 A | 5/1996 | Chu et al. | |
| 5,520,636 A | 5/1996 | Korth et al. | |
| 5,531,715 A | 7/1996 | Engelson et al. | |
| 5,531,717 A | 7/1996 | Roberto et al. | |
| 5,536,258 A | 7/1996 | Folden | |
| 5,538,584 A | 7/1996 | Metz | |
| 5,554,140 A | 9/1996 | Michels et al. | |
| 5,554,141 A | 9/1996 | Wendler | |
| 5,558,900 A | 9/1996 | Fan et al. | |
| 5,562,599 A | 10/1996 | Beyschlag | |
| 5,567,495 A | 10/1996 | Modak et al. | |
| 5,569,219 A | 10/1996 | Hakki et al. | |
| 5,582,599 A | 12/1996 | Daneshvar | |
| 5,591,292 A | 1/1997 | Blomqvist | |
| 5,593,718 A | 1/1997 | Conway et al. | |
| 5,599,321 A | 2/1997 | Conway et al. | |
| 5,601,537 A | 2/1997 | Frassica | |
| 5,607,417 A | 3/1997 | Batich et al. | |
| 5,614,143 A | 3/1997 | Hager | |
| 5,616,126 A | 4/1997 | Malekmehr et al. | |
| 5,620,109 A * | 4/1997 | Madden | B65D 83/04 |
| | | | 206/536 |
| 5,624,395 A | 4/1997 | Mikhail et al. | |
| 5,630,429 A | 5/1997 | Dann | |
| 5,643,235 A | 7/1997 | Figuerido | |
| 5,645,048 A | 7/1997 | Brodsky et al. | |
| 5,653,700 A | 8/1997 | Byrne et al. | |
| 5,670,111 A | 9/1997 | Conway et al. | |
| 5,671,755 A | 9/1997 | Simon et al. | |
| 5,688,516 A | 11/1997 | Raad et al. | |
| 5,695,456 A | 12/1997 | Cartmell et al. | |
| 5,695,485 A | 12/1997 | Duperret et al. | |
| 5,702,381 A | 12/1997 | Cottenden | |
| 5,704,353 A | 1/1998 | Kalb et al. | |
| 5,707,357 A | 1/1998 | Mikhail et al. | |
| 5,709,672 A | 1/1998 | Illner | |
| 5,711,841 A | 1/1998 | Jaker | |
| 5,724,994 A | 3/1998 | Simon et al. | |
| 5,730,733 A | 3/1998 | Mortier et al. | |
| 5,736,152 A | 4/1998 | Dunn | |
| 5,749,826 A | 5/1998 | Faulkner | |
| 5,752,525 A | 5/1998 | Simon et al. | |
| 5,756,144 A | 5/1998 | Wolff et al. | |
| 5,762,996 A | 6/1998 | Lucas et al. | |
| 5,779,670 A | 7/1998 | Bidwell et al. | |
| 5,782,808 A | 7/1998 | Folden | |
| 5,785,694 A | 7/1998 | Cohen et al. | |
| 5,788,687 A | 8/1998 | Batich et al. | |
| 5,789,018 A | 8/1998 | Engelson et al. | |
| 5,795,332 A | 8/1998 | Lucas et al. | |
| 5,795,334 A | 8/1998 | Cochrane, III | |
| 5,795,524 A | 8/1998 | Basso, Jr. et al. | |
| 5,800,339 A | 9/1998 | Salama | |
| 5,806,527 A | 9/1998 | Borodulin et al. | |
| 5,810,789 A | 9/1998 | Powers et al. | |
| 5,817,067 A | 10/1998 | Tsukada et al. | |
| 5,820,583 A | 10/1998 | Demopulos et al. | |
| 5,820,607 A | 10/1998 | Tcholakian et al. | |
| 5,827,247 A | 10/1998 | Kay | |

(56)  References Cited

U.S. PATENT DOCUMENTS

| 5,827,249 | A | 10/1998 | Jensen |
|---|---|---|---|
| 5,830,932 | A | 11/1998 | Kay |
| 5,840,151 | A | 11/1998 | Munsch |
| 5,848,691 | A | 12/1998 | Morris et al. |
| 5,853,518 | A | 12/1998 | Utas |
| 5,871,475 | A | 2/1999 | Frassica |
| 5,877,243 | A | 3/1999 | Sarangapani |
| 5,895,374 | A | 4/1999 | Rodsten |
| 5,897,535 | A | 4/1999 | Feliziani et al. |
| 5,902,631 | A | 5/1999 | Wang et al. |
| 5,906,575 | A | 5/1999 | Conway et al. |
| 5,919,170 | A | 7/1999 | Woessner |
| 5,941,856 | A | 8/1999 | Kovacs et al. |
| 5,958,167 | A | 9/1999 | Van Driel et al. |
| 5,971,954 | A | 10/1999 | Conway et al. |
| 5,980,483 | A | 11/1999 | Dimitri |
| 5,980,507 | A | 11/1999 | Fassuliotis et al. |
| 5,989,230 | A | 11/1999 | Frassica |
| 5,997,517 | A | 12/1999 | Whitbourne |
| 6,004,305 | A | 12/1999 | Hursman et al. |
| 6,007,521 | A | 12/1999 | Bidwell et al. |
| 6,007,524 | A | 12/1999 | Schneider |
| 6,007,526 | A | 12/1999 | Passalaqua et al. |
| 6,024,751 | A | 2/2000 | Lovato et al. |
| 6,050,934 | A | 4/2000 | Mikhail et al. |
| 6,053,905 | A | 4/2000 | Daignault, Jr. et al. |
| 6,056,715 | A | 5/2000 | Demopulos et al. |
| 6,059,107 | A | 5/2000 | Nosted et al. |
| 6,063,063 | A | 5/2000 | Harboe et al. |
| 6,065,597 | A | 5/2000 | Pettersson et al. |
| 6,070,275 | A | 6/2000 | Garlock |
| 6,090,075 | A | 7/2000 | House |
| 6,097,976 | A | 8/2000 | Yang et al. |
| 6,102,929 | A | 8/2000 | Conway et al. |
| 6,113,582 | A | 9/2000 | Dwork |
| 6,119,697 | A | 9/2000 | Engel et al. |
| 6,131,575 | A | 10/2000 | Lenker et al. |
| 6,132,399 | A | 10/2000 | Shultz |
| 6,156,049 | A | 12/2000 | Lovato et al. |
| 6,162,201 | A | 12/2000 | Cohen et al. |
| 6,183,461 | B1 | 2/2001 | Matsuura et al. |
| 6,186,990 | B1 | 2/2001 | Chen et al. |
| 6,190,353 | B1 | 2/2001 | Makower et al. |
| 6,206,885 | B1 | 3/2001 | Ghahremani et al. |
| 6,210,394 | B1 | 4/2001 | Demopulos et al. |
| 6,217,569 | B1 | 4/2001 | Fiore |
| 6,221,056 | B1 | 4/2001 | Silverman |
| 6,231,501 | B1 | 5/2001 | Ditter |
| 6,238,383 | B1 | 5/2001 | Karram et al. |
| 6,254,570 | B1 | 7/2001 | Rutner et al. |
| 6,254,582 | B1 | 7/2001 | O'Donnell et al. |
| 6,254,585 | B1 | 7/2001 | Demopulos et al. |
| 6,256,525 | B1 | 7/2001 | Yang et al. |
| 6,261,255 | B1 | 7/2001 | Mullis et al. |
| 6,261,271 | B1 | 7/2001 | Solomon et al. |
| 6,261,279 | B1 | 7/2001 | Demopulos et al. |
| 6,270,902 | B1 | 8/2001 | Tedeschi et al. |
| 6,280,425 | B1 | 8/2001 | Del Guercio |
| 6,287,285 | B1 | 9/2001 | Michal et al. |
| 6,293,923 | B1 | 9/2001 | Yachia et al. |
| 6,296,627 | B1 | 10/2001 | Edwards |
| 6,299,598 | B1 | 10/2001 | Bander |
| 6,306,176 | B1 | 10/2001 | Whitbourne |
| 6,306,422 | B1 | 10/2001 | Batich et al. |
| 6,309,104 | B1 | 10/2001 | Koch et al. |
| 6,315,711 | B1 | 11/2001 | Conway et al. |
| 6,329,488 | B1 | 12/2001 | Terry et al. |
| 6,340,359 | B1 | 1/2002 | Silverman |
| 6,340,465 | B1 | 1/2002 | Hsu et al. |
| 6,355,004 | B1 | 3/2002 | Pedersen et al. |
| 6,358,229 | B1 | 3/2002 | Tihon |
| 6,368,315 | B1 | 4/2002 | Gillis et al. |
| 6,368,317 | B2 | 4/2002 | Chang |
| 6,379,334 | B1 | 4/2002 | Frassica |
| 6,383,434 | B2 | 5/2002 | Conway et al. |
| 6,387,080 | B1 | 5/2002 | Rodsten |
| 6,391,010 | B1 | 5/2002 | Wilcox |
| 6,391,014 | B1 | 5/2002 | Silverman |
| 6,398,718 | B1 | 6/2002 | Yachia et al. |
| 6,402,726 | B1 | 6/2002 | Genese |
| 6,409,717 | B1 | 6/2002 | Israelsson et al. |
| 6,423,041 | B1 | 7/2002 | Grant |
| 6,437,038 | B1 | 8/2002 | Chen |
| 6,440,060 | B1 | 8/2002 | Latour, Jr. |
| 6,458,867 | B1 | 10/2002 | Wang et al. |
| 6,468,245 | B2 | 10/2002 | Alexandersen |
| 6,479,000 | B2 | 11/2002 | Conway et al. |
| 6,479,726 | B1 | 11/2002 | Cole |
| 6,485,476 | B1 | 11/2002 | von Dyck et al. |
| 6,509,319 | B1 | 1/2003 | Raad et al. |
| 6,544,240 | B1 | 4/2003 | Borodulin et al. |
| 6,551,293 | B1 | 4/2003 | Mitchell |
| 6,558,369 | B2 | 5/2003 | Rosenblum |
| 6,558,792 | B1 | 5/2003 | Vaabengaard et al. |
| 6,558,798 | B2 | 5/2003 | Zhong et al. |
| 6,578,709 | B1 | 6/2003 | Kavanagh et al. |
| 6,579,539 | B2 | 6/2003 | Lawson et al. |
| 6,582,401 | B1 | 6/2003 | Windheuser et al. |
| 6,596,401 | B1 | 7/2003 | Terry et al. |
| 6,602,244 | B2 | 8/2003 | Kavanagh et al. |
| 6,613,014 | B1 | 9/2003 | Chi |
| 6,613,342 | B2 | 9/2003 | Aoki |
| 6,626,888 | B1 | 9/2003 | Conway et al. |
| 6,629,969 | B2 | 10/2003 | Chan et al. |
| 6,632,204 | B2 | 10/2003 | Guldfeldt et al. |
| 6,634,498 | B2 | 10/2003 | Kayerod et al. |
| 6,638,269 | B2 | 10/2003 | Wilcox |
| 6,648,906 | B2 | 11/2003 | Lasheras et al. |
| 6,659,937 | B2 | 12/2003 | Polsky et al. |
| 6,682,555 | B2 | 1/2004 | Cioanta et al. |
| 6,693,189 | B2 | 2/2004 | Holt et al. |
| 6,695,831 | B1 | 2/2004 | Tsukada et al. |
| 6,706,025 | B2 | 3/2004 | Engelson et al. |
| 6,711,436 | B1 | 3/2004 | Duhaylongsod |
| 6,716,895 | B1 | 4/2004 | Terry |
| 6,719,709 | B2 | 4/2004 | Whalen et al. |
| 6,723,350 | B2 | 4/2004 | Burrell et al. |
| 6,730,113 | B2 | 5/2004 | Eckhardt et al. |
| 6,733,474 | B2 | 5/2004 | Kusleika |
| 6,736,805 | B2 | 5/2004 | Israelsson et al. |
| 6,740,273 | B2 | 5/2004 | Lee |
| 6,746,421 | B2 | 6/2004 | Yachia et al. |
| 6,767,551 | B2 | 7/2004 | McGhee et al. |
| 6,780,504 | B2 | 8/2004 | Rupprecht et al. |
| 6,783,520 | B1 | 8/2004 | Candray et al. |
| D496,266 | S | 9/2004 | Nestenborg |
| 6,787,156 | B1 | 9/2004 | Bar-Shalom |
| 6,797,743 | B2 | 9/2004 | McDonald et al. |
| 6,824,532 | B2 | 11/2004 | Gillis et al. |
| 6,835,183 | B2 | 12/2004 | Ennox et al. |
| 6,835,410 | B2 | 12/2004 | Chabrecek et al. |
| 6,840,379 | B2 | 1/2005 | Franks-Farah et al. |
| 6,848,574 | B1 | 2/2005 | Israelsson et al. |
| 6,849,070 | B1 | 2/2005 | Hansen et al. |
| 6,852,098 | B2 | 2/2005 | Byrne |
| 6,852,105 | B2 | 2/2005 | Bolmsjo et al. |
| D503,335 | S | 3/2005 | Risberg et al. |
| 6,869,416 | B2 | 3/2005 | Windheuser et al. |
| 6,872,195 | B2 | 3/2005 | Modak et al. |
| 6,887,223 | B2 | 5/2005 | Bisbee |
| 6,887,230 | B2 | 5/2005 | Kubalak et al. |
| 6,889,740 | B2 | 5/2005 | Globensky et al. |
| 6,918,924 | B2 | 7/2005 | Lasheras et al. |
| 6,926,708 | B1 | 8/2005 | Franks-Farah et al. |
| 6,939,339 | B1 | 9/2005 | Axexandersen et al. |
| 6,939,554 | B2 | 9/2005 | McDonald et al. |
| 6,941,171 | B2 | 9/2005 | Mann et al. |
| 6,942,634 | B2 | 9/2005 | Odland |
| 6,945,957 | B2 | 9/2005 | Freyman |
| 6,949,598 | B2 | 9/2005 | Terry |
| 6,951,902 | B2 | 10/2005 | McDonald et al. |
| 6,972,040 | B2 | 12/2005 | Rioux et al. |
| 7,001,370 | B2 | 2/2006 | Kubalak et al. |
| 7,033,367 | B2 | 4/2006 | Ghahremani et al. |

(56)         References Cited

U.S. PATENT DOCUMENTS

| | | | |
|---|---|---|---|
| 7,048,717 | B1 | 5/2006 | Frassica |
| 7,059,330 | B1 | 6/2006 | Makower et al. |
| 7,066,912 | B2 | 6/2006 | Nestenborg et al. |
| 7,087,041 | B2 | 8/2006 | von Dyck et al. |
| 7,087,048 | B2 | 8/2006 | Israelsson et al. |
| 7,094,220 | B2 | 8/2006 | Tanghoj et al. |
| 7,112,298 | B2 | 9/2006 | Kampa et al. |
| 7,160,277 | B2 | 1/2007 | Elson et al. |
| 7,166,092 | B2 | 1/2007 | Elson et al. |
| 7,195,608 | B2 | 3/2007 | Burnett |
| 7,204,940 | B2 | 4/2007 | McDonald et al. |
| 7,211,275 | B2 | 5/2007 | Mng et al. |
| 7,244,242 | B2 | 7/2007 | Freyman |
| 7,250,043 | B2 | 7/2007 | Chan et al. |
| 7,255,687 | B2 | 8/2007 | Huang et al. |
| 7,270,647 | B2 | 9/2007 | Karpowicz et al. |
| 7,294,117 | B2 | 11/2007 | Provost-Tine et al. |
| 7,311,690 | B2 | 12/2007 | Burnett |
| 7,311,698 | B2 | 12/2007 | Tanghoj et al. |
| 7,329,412 | B2 | 2/2008 | Modak et al. |
| 7,331,948 | B2 | 2/2008 | Skarda |
| 7,334,679 | B2 | 2/2008 | Givens, Jr. |
| 7,374,040 | B2 | 5/2008 | Lee et al. |
| 7,380,658 | B2 | 6/2008 | Murray et al. |
| 7,402,559 | B2 | 7/2008 | Catania et al. |
| 7,445,812 | B2 | 11/2008 | Schmidt et al. |
| 7,458,964 | B2 | 12/2008 | Mosler et al. |
| 7,476,223 | B2 | 1/2009 | McBride |
| 7,507,229 | B2 | 3/2009 | Hewitt et al. |
| 7,517,343 | B2 | 4/2009 | Tanghoj et al. |
| 7,537,589 | B2 | 5/2009 | Tsukada et al. |
| 7,571,804 | B2 | 8/2009 | Kjellmann Bruun et al. |
| 7,601,158 | B2 | 10/2009 | House |
| 7,615,045 | B2 | 11/2009 | Israelsson et al. |
| 7,628,784 | B2 | 12/2009 | Diaz et al. |
| 7,632,256 | B2 | 12/2009 | Mosler et al. |
| D609,819 | S | 2/2010 | Tomes et al. |
| 7,662,146 | B2 | 2/2010 | House |
| 7,670,331 | B2 | 3/2010 | Tanghoej |
| 7,682,353 | B2 | 3/2010 | Tanghoj et al. |
| 7,682,669 | B1 | 3/2010 | Michal et al. |
| 7,691,091 | B1 | 4/2010 | Baggett |
| 7,691,476 | B2 | 4/2010 | Finley |
| 7,717,902 | B2 | 5/2010 | Sauer |
| 7,749,529 | B2 | 7/2010 | Ash et al. |
| 7,770,726 | B2 | 8/2010 | Murray et al. |
| 7,770,728 | B2 | 8/2010 | Kaern |
| 7,780,640 | B1 | 8/2010 | Amador |
| 7,780,642 | B2 | 8/2010 | Rasmussen et al. |
| 7,789,873 | B2 | 9/2010 | Kubalak et al. |
| 7,820,734 | B2 | 10/2010 | McGhee |
| 7,823,722 | B2 | 11/2010 | Bezou et al. |
| 7,846,133 | B2 | 12/2010 | Windheuser et al. |
| 7,867,220 | B2 | 1/2011 | Tanghoj |
| 7,886,907 | B2 | 2/2011 | Murray et al. |
| 7,896,857 | B2 | 3/2011 | Kay et al. |
| 7,918,831 | B2 | 4/2011 | House |
| 7,938,838 | B2 | 5/2011 | House |
| 7,947,021 | B2 | 5/2011 | Bourne et al. |
| 7,985,217 | B2 | 7/2011 | Mosler et al. |
| 8,007,464 | B2 | 8/2011 | Gellman |
| 8,011,505 | B2 | 9/2011 | Murray et al. |
| 8,051,981 | B2 | 11/2011 | Murray et al. |
| 8,052,673 | B2 | 11/2011 | Nestenborg |
| 8,053,030 | B2 | 11/2011 | Gilman |
| 8,066,693 | B2 | 11/2011 | Tanghoj et al. |
| 8,127,922 | B2 | 3/2012 | Nordholm et al. |
| 8,133,580 | B2 | 3/2012 | Dias et al. |
| 8,163,327 | B2 | 4/2012 | Finley |
| 8,177,774 | B2 | 5/2012 | House |
| 8,181,778 | B1 | 5/2012 | van Groningen et al. |
| 8,192,413 | B2 | 6/2012 | Bjerregaard |
| 8,201,689 | B2 | 6/2012 | Kaern |
| 8,205,745 | B2 | 6/2012 | Murray et al. |
| 8,207,393 | B2 | 6/2012 | Bach |
| 8,230,993 | B2 | 7/2012 | Tanghoej |
| 8,267,919 | B2 | 9/2012 | Utas et al. |
| 8,282,624 | B2 | 10/2012 | Tanghoej et al. |
| 8,287,519 | B2 | 10/2012 | Smith |
| 8,287,890 | B2 | 10/2012 | Elton |
| 8,298,202 | B2 | 10/2012 | McCray |
| 8,303,556 | B2 | 11/2012 | White |
| 8,317,775 | B2 | 11/2012 | House |
| 8,328,792 | B2 | 12/2012 | Nishtala et al. |
| 8,356,457 | B2 | 1/2013 | Murray et al. |
| 8,377,498 | B2 | 2/2013 | Rindlav-Westling et al. |
| 8,377,559 | B2 | 2/2013 | Gilman |
| 8,382,708 | B2 | 2/2013 | Mayback et al. |
| 8,398,615 | B2 | 3/2013 | Torstensen et al. |
| 8,409,171 | B2 | 4/2013 | Hannon et al. |
| 8,454,569 | B2 | 6/2013 | Kull-Osterlin et al. |
| 8,459,455 | B2 | 6/2013 | Frojd |
| 8,475,434 | B2 | 7/2013 | Frojd |
| 8,523,843 | B2 | 9/2013 | Kavanagh et al. |
| 8,556,884 | B2 | 10/2013 | Hong et al. |
| 8,608,718 | B1 | 12/2013 | Patterson-Young |
| 8,668,683 | B2 | 3/2014 | Golden |
| 8,720,685 | B2 | 5/2014 | Murray et al. |
| 8,805,533 | B2 | 8/2014 | Boggs, II et al. |
| 8,871,869 | B2 | 10/2014 | Dias et al. |
| 8,888,747 | B2 | 11/2014 | House |
| 8,919,553 | B2 | 12/2014 | Murray et al. |
| 8,974,438 | B2 | 3/2015 | Hong et al. |
| 8,998,882 | B2 | 4/2015 | Knapp et al. |
| 9,033,149 | B2 | 5/2015 | Terry |
| 9,072,862 | B2 | 7/2015 | Murray et al. |
| 9,078,760 | B2 | 7/2015 | Marshall |
| 9,108,020 | B1 | 8/2015 | Feloney |
| 9,114,227 | B2 | 8/2015 | Blanchard |
| 9,138,510 | B2 | 9/2015 | Madsen |
| 9,144,659 | B2 | 9/2015 | Tanghoj |
| 9,168,354 | B2 | 10/2015 | Hannon et al. |
| 9,186,438 | B2 | 11/2015 | Gravesen et al. |
| 9,192,506 | B2 | 11/2015 | Tanghoej et al. |
| 9,192,740 | B2 | 11/2015 | Frojd |
| 9,199,057 | B2 | 12/2015 | Nielsen |
| 9,205,222 | B2 | 12/2015 | Tanghoj |
| 9,220,866 | B2 | 12/2015 | Van Groningen et al. |
| 9,289,575 | B2 | 3/2016 | Dye |
| 9,314,585 | B2 | 4/2016 | Nestenborg et al. |
| 9,345,855 | B2 | 5/2016 | Young |
| 9,511,204 | B2 | 12/2016 | Tanghøj |
| 9,561,889 | B2 | 2/2017 | Dayrit et al. |
| 9,649,472 | B2 | 5/2017 | Kearns et al. |
| 9,669,187 | B2 | 6/2017 | Tjassens et al. |
| 9,687,628 | B2 | 6/2017 | Paz |
| 9,694,113 | B2 | 7/2017 | Knapp et al. |
| 9,694,157 | B2 | 7/2017 | Palmer |
| 9,707,375 | B2 | 7/2017 | Conway et al. |
| 9,731,093 | B2 | 8/2017 | Terry |
| 9,775,965 | B2 | 10/2017 | Tanghoej et al. |
| 9,801,979 | B2 | 10/2017 | Utas et al. |
| 9,821,139 | B2 | 11/2017 | Carleo |
| 9,872,969 | B2 | 1/2018 | Conway et al. |
| 9,884,167 | B2 | 2/2018 | Gustavsson |
| 9,918,869 | B2 | 3/2018 | Henry et al. |
| 9,937,334 | B2 | 4/2018 | Fröjd et al. |
| 10,112,031 | B2 | 10/2018 | Matthiassen |
| 10,118,019 | B2 | 11/2018 | Murray et al. |
| 10,149,961 | B2 | 12/2018 | Carleo |
| 10,166,366 | B2 | 1/2019 | Murray et al. |
| 10,179,676 | B1 | 1/2019 | Taylor |
| 10,207,076 | B2 | 2/2019 | Foley et al. |
| 10,265,499 | B2 | 4/2019 | Hong et al. |
| 10,328,237 | B2 | 6/2019 | Kelly et al. |
| 10,406,322 | B2 | 9/2019 | O'Flynn et al. |
| 10,441,454 | B2 | 10/2019 | Tanghoej et al. |
| 10,449,328 | B2 | 10/2019 | Tanghoej et al. |
| 10,449,329 | B2 | 10/2019 | Foley et al. |
| 10,518,000 | B2 | 12/2019 | Knapp et al. |
| 10,561,817 | B2 | 2/2020 | Hannon et al. |
| 10,569,046 | B2 | 2/2020 | Steindahl et al. |
| 10,569,051 | B2 | 2/2020 | Conway et al. |
| 10,639,451 | B2 | 5/2020 | Kearns et al. |

(56) References Cited

U.S. PATENT DOCUMENTS

| | | |
|---|---|---|
| 10,646,688 B2 | 5/2020 | Hannon et al. |
| 10,702,671 B2 | 7/2020 | Terry |
| 10,758,704 B2 | 9/2020 | Hickmott et al. |
| 10,765,833 B2 | 9/2020 | Kearns |
| 10,857,324 B2 | 12/2020 | Yin et al. |
| 10,874,825 B2 | 12/2020 | Yin et al. |
| RE48,426 E | 2/2021 | Murray et al. |
| 10,912,917 B2 | 2/2021 | Terry |
| 11,020,561 B2 | 6/2021 | O'Brien et al. |
| 11,103,676 B2 | 8/2021 | McMenamin et al. |
| 11,129,961 B2 | 9/2021 | O'Flynn |
| 11,141,562 B2 | 10/2021 | McMenamin et al. |
| 11,154,688 B2 | 10/2021 | Schertiger |
| 11,167,107 B2 | 11/2021 | Schertiger et al. |
| 11,235,130 B2 | 2/2022 | Murray et al. |
| 11,235,675 B2 | 2/2022 | Choi et al. |
| 11,241,566 B1 | 2/2022 | Lindsay |
| 11,253,675 B2 | 2/2022 | Fletter |
| 11,344,702 B2 | 5/2022 | Subramaniam et al. |
| 11,400,257 B2 | 8/2022 | Tierney et al. |
| 11,420,017 B2 | 8/2022 | Hilton et al. |
| 11,534,573 B2 | 12/2022 | Hannon et al. |
| 11,547,833 B2 | 1/2023 | Murray et al. |
| 11,607,524 B2 | 3/2023 | Conway et al. |
| 2001/0001443 A1 | 5/2001 | Kayerod et al. |
| 2001/0027299 A1 | 10/2001 | Yang et al. |
| 2001/0031933 A1 | 10/2001 | Cannon |
| 2001/0031952 A1 | 10/2001 | Karram et al. |
| 2001/0047147 A1 | 11/2001 | Slepian et al. |
| 2001/0054562 A1 | 12/2001 | Pettersson et al. |
| 2002/0007175 A1 | 1/2002 | Chang |
| 2002/0032406 A1 | 3/2002 | Kusleika |
| 2002/0037943 A1 | 3/2002 | Madsen |
| 2002/0045855 A1 | 4/2002 | Frassica |
| 2002/0055730 A1 | 5/2002 | Yachia et al. |
| 2002/0077611 A1 | 6/2002 | von Dyck et al. |
| 2002/0082551 A1 | 6/2002 | Yachia et al. |
| 2002/0087131 A1 | 7/2002 | Wolff et al. |
| 2002/0094322 A1 | 7/2002 | Lawson et al. |
| 2002/0095133 A1 | 7/2002 | Gillis et al. |
| 2002/0099356 A1 | 7/2002 | Unger et al. |
| 2002/0103467 A1 | 8/2002 | Kubalak |
| 2002/0107467 A1 | 8/2002 | Levin |
| 2002/0132013 A1 | 9/2002 | Moulis |
| 2002/0132049 A1 | 9/2002 | Leonard et al. |
| 2002/0133130 A1 | 9/2002 | Wilcox |
| 2002/0156440 A1 | 10/2002 | Israelsson et al. |
| 2002/0165427 A1 | 11/2002 | Yachia et al. |
| 2002/0169438 A1 | 11/2002 | Sauer |
| 2002/0182265 A1 | 12/2002 | Burrell et al. |
| 2003/0004496 A1 | 1/2003 | Tanghoj |
| 2003/0018293 A1 | 1/2003 | Tanghoj et al. |
| 2003/0018302 A1 | 1/2003 | Kavanagh et al. |
| 2003/0018322 A1 | 1/2003 | Tanghoj et al. |
| 2003/0023222 A1 | 1/2003 | Chen |
| 2003/0028174 A1 | 2/2003 | Chan et al. |
| 2003/0036802 A1 | 2/2003 | Lennox et al. |
| 2003/0055403 A1 | 3/2003 | Nestenborg et al. |
| 2003/0060807 A1 | 3/2003 | Tanghoj et al. |
| 2003/0065292 A1 | 4/2003 | Darouiche et al. |
| 2003/0083644 A1 | 5/2003 | Avaltroni |
| 2003/0130646 A1 | 7/2003 | Kubalak et al. |
| 2003/0132307 A1 | 7/2003 | Park |
| 2003/0135200 A1 | 7/2003 | Byrne |
| 2003/0163079 A1 | 8/2003 | Burnett |
| 2003/0168365 A1 | 9/2003 | Kaern |
| 2003/0195478 A1 | 10/2003 | Russo |
| 2003/0225392 A1 | 12/2003 | McMichael et al. |
| 2003/0233084 A1 | 12/2003 | Slepian et al. |
| 2004/0030301 A1 | 2/2004 | Hunter |
| 2004/0034329 A1 | 2/2004 | Mankus et al. |
| 2004/0044307 A1 | 3/2004 | Richardson et al. |
| 2004/0049152 A1 | 3/2004 | Nayak |
| 2004/0049170 A1 | 3/2004 | Snell |
| 2004/0055925 A1 | 3/2004 | Franks-Farah et al. |
| 2004/0059280 A1 | 3/2004 | Makower et al. |
| 2004/0068251 A1 | 4/2004 | Chan et al. |
| 2004/0074794 A1 | 4/2004 | Conway et al. |
| 2004/0097892 A1 | 5/2004 | Evans et al. |
| 2004/0116551 A1 | 6/2004 | Terry |
| 2004/0122382 A1 | 6/2004 | Johnson et al. |
| 2004/0127848 A1 | 7/2004 | Freyman |
| 2004/0133156 A1 | 7/2004 | Diaz et al. |
| 2004/0147871 A1 | 7/2004 | Burnett |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0176747 A1 | 9/2004 | Feneley |
| 2004/0193143 A1 | 9/2004 | Sauer |
| 2004/0234572 A1 | 11/2004 | Martinod et al. |
| 2004/0236293 A1 | 11/2004 | Tanghoj et al. |
| 2004/0243104 A1 | 12/2004 | Seddon |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0003118 A1 | 1/2005 | Takala |
| 2005/0011790 A1 | 1/2005 | Harrold |
| 2005/0015076 A1 | 1/2005 | Giebmeyer et al. |
| 2005/0031872 A1 | 2/2005 | Schmidt et al. |
| 2005/0033222 A1 | 2/2005 | Haggstrom et al. |
| 2005/0043715 A1 | 2/2005 | Nestenborg et al. |
| 2005/0049577 A1 | 3/2005 | Snell et al. |
| 2005/0059990 A1 | 3/2005 | Ayala et al. |
| 2005/0065499 A1 | 3/2005 | Douk et al. |
| 2005/0070882 A1 | 3/2005 | McBride |
| 2005/0080399 A1 | 4/2005 | Bolmsjo et al. |
| 2005/0096582 A1 | 5/2005 | Burnett |
| 2005/0101923 A1 | 5/2005 | Elson et al. |
| 2005/0101924 A1 | 5/2005 | Elson et al. |
| 2005/0107735 A1 | 5/2005 | Lennox et al. |
| 2005/0107771 A1 | 5/2005 | Finkbeiner |
| 2005/0109648 A1 | 5/2005 | Kerzman et al. |
| 2005/0137522 A1 | 6/2005 | Aoki |
| 2005/0137582 A1 | 6/2005 | Kull-Osterlin et al. |
| 2005/0143690 A1 | 6/2005 | High |
| 2005/0148950 A1 | 7/2005 | Windheuser et al. |
| 2005/0177104 A1 | 8/2005 | Conway |
| 2005/0197531 A1 | 9/2005 | Cabiri et al. |
| 2005/0199521 A1 | 9/2005 | Givens |
| 2005/0209580 A1 | 9/2005 | Freyman |
| 2005/0214443 A1 | 9/2005 | Madsen |
| 2005/0245901 A1 | 11/2005 | Floyd |
| 2005/0251108 A1 | 11/2005 | Frassica |
| 2005/0256447 A1 | 11/2005 | Richardson et al. |
| 2005/0273034 A1 | 12/2005 | Burnett |
| 2005/0282977 A1 | 12/2005 | Stempel et al. |
| 2005/0283136 A1 | 12/2005 | Skarda |
| 2006/0025753 A1 | 2/2006 | Kubalak et al. |
| 2006/0027854 A1 | 2/2006 | Kim et al. |
| 2006/0030864 A1 | 2/2006 | Kennedy et al. |
| 2006/0036208 A1 | 2/2006 | Burnett |
| 2006/0041246 A1 | 2/2006 | Provost-Tine et al. |
| 2006/0054557 A1 | 3/2006 | Hori et al. |
| 2006/0058777 A1 | 3/2006 | Nielsen |
| 2006/0064065 A1 | 3/2006 | Russo |
| 2006/0079835 A1 | 4/2006 | Frassica |
| 2006/0079854 A1 | 4/2006 | Kay et al. |
| 2006/0100511 A1 | 5/2006 | Eriksen |
| 2006/0122566 A1 | 6/2006 | Huang et al. |
| 2006/0122568 A1 | 6/2006 | Elson et al. |
| 2006/0142737 A1 | 6/2006 | Tanghoj |
| 2006/0172096 A1 | 8/2006 | Kyle et al. |
| 2006/0184112 A1 | 8/2006 | Horn et al. |
| 2006/0184145 A1 | 8/2006 | Ciok et al. |
| 2006/0189962 A1 | 8/2006 | Burtoft |
| 2006/0196783 A1 | 9/2006 | Bruun et al. |
| 2006/0200079 A1 | 9/2006 | Magnusson |
| 2006/0229576 A1 | 10/2006 | Conway et al. |
| 2006/0240069 A1 | 10/2006 | Utas et al. |
| 2006/0263404 A1 | 11/2006 | Nielsen et al. |
| 2006/0271019 A1 | 11/2006 | Stoller et al. |
| 2006/0276894 A1 | 12/2006 | Finley |
| 2006/0278546 A1 | 12/2006 | State et al. |

(56)          References Cited

U.S. PATENT DOCUMENTS

| | | |
|---|---|---|
| 2006/0293642 A1 | 12/2006 | Sraelsson et al. |
| 2007/0005024 A1 | 1/2007 | Weber et al. |
| 2007/0005041 A1 | 1/2007 | Frassica et al. |
| 2007/0010798 A1 | 1/2007 | Stoller et al. |
| 2007/0016168 A1 | 1/2007 | Conway |
| 2007/0016169 A1 | 1/2007 | Utas et al. |
| 2007/0049879 A1 | 3/2007 | Gutierrez |
| 2007/0059350 A1 | 3/2007 | Kennedy et al. |
| 2007/0066963 A1 | 3/2007 | Tanghoj |
| 2007/0084749 A1 | 4/2007 | Demelo et al. |
| 2007/0088330 A1 | 4/2007 | House |
| 2007/0106233 A1 | 5/2007 | Huang et al. |
| 2007/0108076 A1 | 5/2007 | Miller et al. |
| 2007/0112327 A1 | 5/2007 | Yun et al. |
| 2007/0112333 A1 | 5/2007 | Hoang et al. |
| 2007/0149929 A1 | 6/2007 | Utas et al. |
| 2007/0161971 A1 | 7/2007 | House |
| 2007/0197957 A1 | 8/2007 | Hunter et al. |
| 2007/0218102 A1 | 9/2007 | Chudzik et al. |
| 2007/0225635 A1 | 9/2007 | Lynn |
| 2007/0225649 A1 | 9/2007 | House |
| 2007/0225687 A1 | 9/2007 | House |
| 2007/0244449 A1 | 10/2007 | Najafi et al. |
| 2007/0287800 A1 | 12/2007 | Acquarulo et al. |
| 2007/0289887 A1 | 12/2007 | Murray et al. |
| 2008/0006554 A1 | 1/2008 | Duffy et al. |
| 2008/0015518 A1 | 1/2008 | Huang et al. |
| 2008/0015527 A1 | 1/2008 | House |
| 2008/0021382 A1 | 1/2008 | Freyman |
| 2008/0027414 A1 | 1/2008 | Tanghoj et al. |
| 2008/0033471 A1 | 2/2008 | Paz et al. |
| 2008/0050446 A1 | 2/2008 | Ziegler et al. |
| 2008/0051762 A1 | 2/2008 | Tsukada et al. |
| 2008/0051763 A1 | 2/2008 | Frojd |
| 2008/0063324 A1 | 3/2008 | Bernard et al. |
| 2008/0077099 A1 | 3/2008 | House |
| 2008/0082051 A1 | 4/2008 | Miller et al. |
| 2008/0085949 A1 | 4/2008 | McGhee |
| 2008/0091145 A1 | 4/2008 | House |
| 2008/0097362 A1 | 4/2008 | Mosler et al. |
| 2008/0097394 A1 | 4/2008 | Lampropoulos et al. |
| 2008/0097411 A1 | 4/2008 | House |
| 2008/0103464 A1 | 5/2008 | Mosler et al. |
| 2008/0119803 A1 | 5/2008 | Lund |
| 2008/0125513 A1 | 5/2008 | Kristiansen |
| 2008/0140010 A1 | 6/2008 | Kennedy et al. |
| 2008/0140052 A1 | 6/2008 | Moller et al. |
| 2008/0171973 A1 | 7/2008 | House |
| 2008/0171998 A1 | 7/2008 | House |
| 2008/0172016 A1 | 7/2008 | House |
| 2008/0172040 A1 | 7/2008 | Smith |
| 2008/0172042 A1 | 7/2008 | House |
| 2008/0177217 A1 | 7/2008 | Polaschegg |
| 2008/0179208 A1 | 7/2008 | Murray et al. |
| 2008/0183262 A1 | 7/2008 | Dowling |
| 2008/0193497 A1 | 8/2008 | Samuelsen et al. |
| 2008/0200907 A1 | 8/2008 | Nestenborg |
| 2008/0215021 A1 | 9/2008 | Cisko, Jr. et al. |
| 2008/0243081 A1 | 10/2008 | Nance et al. |
| 2008/0243091 A1 | 10/2008 | Humphreys et al. |
| 2008/0249467 A1 | 10/2008 | Burnett et al. |
| 2008/0249482 A1 | 10/2008 | Erez |
| 2008/0275463 A1 | 11/2008 | High |
| 2008/0279907 A1 | 11/2008 | Ash et al. |
| 2008/0281291 A1 | 11/2008 | Tihon et al. |
| 2009/0000970 A1 | 1/2009 | Bordeau et al. |
| 2009/0005725 A1 | 1/2009 | Shorey |
| 2009/0012208 A1 | 1/2009 | Madsen et al. |
| 2009/0024111 A1 | 1/2009 | Borodulin et al. |
| 2009/0043287 A1 | 2/2009 | Mosler et al. |
| 2009/0048537 A1 | 2/2009 | Lydon et al. |
| 2009/0048570 A1 | 2/2009 | Jensen |
| 2009/0054876 A1 | 2/2009 | Borodulin et al. |
| 2009/0062754 A1 | 3/2009 | Tang |
| 2009/0065605 A1 | 3/2009 | Roche et al. |
| 2009/0071851 A1 | 3/2009 | Maki et al. |
| 2009/0099532 A1 | 4/2009 | Cuevas et al. |
| 2009/0101531 A1 | 4/2009 | Nordholm et al. |
| 2009/0112171 A1 | 4/2009 | Ng et al. |
| 2009/0131917 A1 | 5/2009 | Kavanagh et al. |
| 2009/0137985 A1 | 5/2009 | Tanghoej et al. |
| 2009/0137986 A1 | 5/2009 | Golden et al. |
| 2009/0149837 A1 | 6/2009 | Tanghoj et al. |
| 2009/0156882 A1 | 6/2009 | Chi Sing et al. |
| 2009/0163884 A1 | 6/2009 | Kull-Osterlin et al. |
| 2009/0200187 A1 | 8/2009 | Nestenborg et al. |
| 2009/0208368 A1 | 8/2009 | Waldrep et al. |
| 2009/0221992 A1 | 9/2009 | Hannon et al. |
| 2009/0299334 A1 | 12/2009 | Nishtala et al. |
| 2009/0314795 A1 | 12/2009 | Rapko et al. |
| 2009/0318900 A1 | 12/2009 | Tanghoj et al. |
| 2010/0010086 A1 | 1/2010 | Ash et al. |
| 2010/0030197 A1 | 2/2010 | House |
| 2010/0036363 A1 | 2/2010 | Watanabe et al. |
| 2010/0047123 A1 | 2/2010 | Solomon et al. |
| 2010/0086580 A1 | 4/2010 | Nyman et al. |
| 2010/0133172 A1 | 6/2010 | Song et al. |
| 2010/0152686 A1 | 6/2010 | Ryder et al. |
| 2010/0155268 A1 | 6/2010 | Murray et al. |
| 2010/0198195 A1 | 8/2010 | Nishtala et al. |
| 2010/0228233 A1 | 9/2010 | Kahn |
| 2010/0256576 A1 | 10/2010 | Aggarwal et al. |
| 2010/0258568 A1 | 10/2010 | Frederiksen et al. |
| 2010/0263327 A1 | 10/2010 | Murray et al. |
| 2010/0324540 A1 | 12/2010 | Paulen et al. |
| 2011/0028943 A1 | 2/2011 | Lawson et al. |
| 2011/0056852 A1 | 3/2011 | Frojd |
| 2011/0059874 A1 | 3/2011 | Rooijmans et al. |
| 2011/0060317 A1 | 3/2011 | Frojd |
| 2011/0114520 A1 | 5/2011 | Matthison-Hansen |
| 2011/0127186 A1 | 6/2011 | Enns et al. |
| 2011/0137243 A1 | 6/2011 | Hossainy et al. |
| 2011/0137296 A1 | 6/2011 | Tanghoj |
| 2011/0144579 A1 | 6/2011 | Elton |
| 2011/0147238 A1 | 6/2011 | Tanghoej et al. |
| 2011/0152843 A1 | 6/2011 | Wedlin et al. |
| 2011/0160704 A1 | 6/2011 | Park |
| 2011/0178507 A1 | 7/2011 | Bracken et al. |
| 2011/0184386 A1 | 7/2011 | House |
| 2011/0213025 A1 | 9/2011 | Finch, Jr. |
| 2011/0224653 A1 | 9/2011 | Torstensen |
| 2011/0284409 A1 | 11/2011 | Murray et al. |
| 2011/0295239 A1 | 12/2011 | Gustavsson |
| 2012/0037525 A1 | 2/2012 | Peck et al. |
| 2012/0168324 A1 | 7/2012 | Carleo |
| 2012/0179102 A1 | 7/2012 | Blanchard et al. |
| 2012/0179144 A1 | 7/2012 | Carleo |
| 2012/0193255 A1 | 8/2012 | Lareau et al. |
| 2012/0219742 A1 | 8/2012 | Gravesen et al. |
| 2012/0228165 A1 | 9/2012 | Murray et al. |
| 2012/0239005 A1 | 9/2012 | Conway et al. |
| 2012/0271101 A1 | 10/2012 | Tan |
| 2012/0284991 A1 | 11/2012 | Kusz et al. |
| 2012/0308805 A1 | 12/2012 | Sella |
| 2012/0310210 A1 | 12/2012 | Campbell et al. |
| 2012/0316515 A1 | 12/2012 | Terry |
| 2012/0330255 A1 | 12/2012 | Carlin |
| 2013/0006226 A1 | 1/2013 | Hong et al. |
| 2013/0037306 A1 | 2/2013 | Kim |
| 2013/0048516 A1 | 2/2013 | Nishtala et al. |
| 2013/0077899 A1 | 3/2013 | Odabashian et al. |
| 2013/0085469 A1 | 4/2013 | Polaschegg |
| 2013/0131647 A1 | 5/2013 | Nielsen |
| 2013/0138083 A1 | 5/2013 | Tennican |
| 2013/0138088 A1 | 5/2013 | Nielsen |
| 2013/0146599 A1 | 6/2013 | Murray et al. |
| 2013/0153446 A1 | 6/2013 | Utas et al. |
| 2013/0161208 A1 | 6/2013 | Gustavsson |
| 2013/0161227 A1 | 6/2013 | Gustavsson |
| 2013/0186778 A1 | 7/2013 | Terry |
| 2013/0218136 A1 | 8/2013 | Tanghoej et al. |
| 2013/0231641 A1 | 9/2013 | Gustavsson |
| 2013/0253426 A1 | 9/2013 | Campbell et al. |
| 2013/0261608 A1 | 10/2013 | Tanghoj |

(56)　　　　References Cited

U.S. PATENT DOCUMENTS

| | | |
|---|---|---|
| 2013/0264227 A1 | 10/2013 | Frojd |
| 2013/0289537 A1 | 10/2013 | Schertiger et al. |
| 2014/0066904 A1 | 3/2014 | Young |
| 2014/0066905 A1 | 3/2014 | Young |
| 2014/0193474 A1 | 7/2014 | Babcock et al. |
| 2014/0194857 A1 | 7/2014 | Eilat |
| 2014/0224678 A1* | 8/2014 | Schertiger ........... A61M 25/002 |
| | | 206/210 |
| 2014/0262859 A1 | 9/2014 | Knapp et al. |
| 2014/0271351 A1 | 9/2014 | Nielsen et al. |
| 2014/0271400 A1 | 9/2014 | Cheng et al. |
| 2015/0001107 A1 | 1/2015 | Gustavsson |
| 2015/0051587 A1 | 2/2015 | Rolsted et al. |
| 2015/0068927 A1 | 3/2015 | McBurney et al. |
| 2015/0105756 A1 | 4/2015 | O'Brien et al. |
| 2015/0126975 A1 | 5/2015 | Wuthier |
| 2015/0133898 A1 | 5/2015 | Murray et al. |
| 2015/0202405 A1 | 7/2015 | Schertiger et al. |
| 2015/0231377 A1 | 8/2015 | Tierney et al. |
| 2015/0238726 A1 | 8/2015 | Terry |
| 2015/0258305 A1 | 9/2015 | Dye |
| 2015/0265801 A1 | 9/2015 | Rostami |
| 2015/0273116 A1 | 10/2015 | Knapp et al. |
| 2015/0273183 A1 | 10/2015 | Foley et al. |
| 2015/0297861 A1 | 10/2015 | Passalaqua et al. |
| 2015/0297862 A1 | 10/2015 | Sadik et al. |
| 2015/0306342 A1 | 10/2015 | Rostami et al. |
| 2015/0314103 A1 | 11/2015 | Hannon et al. |
| 2015/0335854 A1 | 11/2015 | Dvarsater et al. |
| 2015/0335856 A1 | 11/2015 | Utas et al. |
| 2015/0335872 A1 | 11/2015 | Yang et al. |
| 2015/0343171 A1 | 12/2015 | Hannon |
| 2015/0352324 A1 | 12/2015 | Palmer |
| 2015/0359996 A1 | 12/2015 | Arora et al. |
| 2016/0001037 A1 | 1/2016 | Hong et al. |
| 2016/0038652 A1 | 2/2016 | Gilman |
| 2016/0038713 A1 | 2/2016 | Keams et al. |
| 2016/0120688 A1 | 5/2016 | Lee |
| 2016/0166822 A1 | 6/2016 | Dodson et al. |
| 2016/0175488 A1 | 6/2016 | Klein et al. |
| 2016/0184551 A1 | 6/2016 | Nyman et al. |
| 2016/0193447 A1 | 7/2016 | Matthiassen |
| 2016/0220784 A1 | 8/2016 | Palmer |
| 2016/0317715 A1 | 11/2016 | Rostami et al. |
| 2016/0325088 A1 | 11/2016 | Nordquist et al. |
| 2016/0325089 A1 | 11/2016 | Burkholz |
| 2017/0173300 A1* | 6/2017 | Hannon ............ A61M 25/0097 |
| 2017/0217658 A1* | 8/2017 | Whitehurst .............. B65D 5/38 |
| 2017/0296704 A1 | 10/2017 | Knapp et al. |
| 2017/0326334 A1 | 11/2017 | Terry |
| 2018/0021481 A1 | 1/2018 | Yin et al. |
| 2018/0050173 A1 | 2/2018 | Kearns |
| 2018/0071486 A1 | 3/2018 | O'Flynn |
| 2018/0104444 A1 | 4/2018 | Yin et al. |
| 2018/0169377 A1 | 6/2018 | Hickmott et al. |
| 2019/0047766 A1 | 2/2019 | Brooks et al. |
| 2019/0083746 A1 | 3/2019 | Murray et al. |
| 2019/0105462 A1 | 4/2019 | Schertiger |
| 2019/0110879 A1* | 4/2019 | Camp ................. A61M 25/002 |
| 2019/0126004 A1 | 5/2019 | O'Brien et al. |
| 2019/0151605 A1* | 5/2019 | McMenamin ....... B65D 43/162 |
| 2019/0151610 A1 | 5/2019 | Fletter |
| 2019/0216985 A1 | 7/2019 | Mcburney et al. |
| 2019/0255280 A1 | 8/2019 | Palmer |
| 2019/0321593 A1 | 10/2019 | Crawford |
| 2019/0358435 A1 | 11/2019 | Andersin et al. |
| 2019/0381272 A1 | 12/2019 | Terry |
| 2020/0001043 A1 | 1/2020 | Heneghan et al. |
| 2020/0016380 A1 | 1/2020 | Murray et al. |
| 2020/0115102 A1* | 4/2020 | Hawry ...................... A61J 1/03 |
| 2020/0155261 A1 | 5/2020 | O'Flynn et al. |
| 2020/0155794 A1 | 5/2020 | Ziebol |
| 2020/0155796 A1 | 5/2020 | Hannon et al. |
| 2020/0171218 A1 | 6/2020 | Dong et al. |
| 2020/0179647 A1 | 6/2020 | Conway et al. |
| 2020/0188631 A1 | 6/2020 | Hannon et al. |
| 2020/0222659 A1 | 7/2020 | Schertiger et al. |
| 2020/0230349 A1 | 7/2020 | McMenamin et al. |
| 2020/0238048 A1 | 7/2020 | Palmer |
| 2020/0246594 A1 | 8/2020 | Miller |
| 2020/0281751 A1 | 9/2020 | Schreck et al. |
| 2020/0345977 A1 | 11/2020 | Hickmott et al. |
| 2020/0361076 A1 | 11/2020 | Richart |
| 2020/0383822 A1 | 12/2020 | Palmer |
| 2020/0391005 A1 | 12/2020 | Murray et al. |
| 2020/0398023 A1 | 12/2020 | Conway et al. |
| 2020/0398024 A1 | 12/2020 | Fletter et al. |
| 2021/0008361 A1 | 1/2021 | Aronson |
| 2021/0100979 A1 | 4/2021 | Donnelly et al. |
| 2021/0113808 A1 | 4/2021 | Yin et al. |
| 2021/0187238 A1 | 6/2021 | O'Brien et al. |
| 2021/0212808 A1 | 7/2021 | Wu et al. |
| 2021/0283367 A1* | 9/2021 | Peters .................. B65D 25/005 |
| 2021/0290894 A1 | 9/2021 | Palmer |
| 2021/0290895 A1 | 9/2021 | Nielsen et al. |
| 2021/0402135 A1 | 12/2021 | McMenamin et al. |
| 2022/0023585 A1 | 1/2022 | Schertiger et al. |
| 2022/0054295 A1 | 2/2022 | Becker |
| 2022/0112018 A1 | 4/2022 | Montano et al. |
| 2022/0117850 A1* | 4/2022 | Romeo .............. B65D 83/0418 |
| 2022/0142810 A1 | 5/2022 | Whittaker |
| 2022/0241549 A1 | 8/2022 | Murray et al. |
| 2022/0273837 A1 | 9/2022 | Paul et al. |
| 2022/0362536 A1 | 11/2022 | Nguyen et al. |
| 2023/0058911 A1 | 2/2023 | Nabors et al. |
| 2023/0072221 A1 | 3/2023 | Donnelly et al. |
| 2023/0073264 A1 | 3/2023 | Kandrac et al. |
| 2023/0075906 A1 | 3/2023 | Piashevich et al. |
| 2023/0077075 A1 | 3/2023 | Kandrac et al. |
| 2023/0166073 A1 | 6/2023 | Radmer |
| 2023/0293848 A1 | 9/2023 | Legaspi et al. |
| 2023/0293849 A1 | 9/2023 | Hughett, Sr. et al. |
| 2024/0108850 A1 | 4/2024 | Mn et al. |
| 2024/0269426 A1 | 8/2024 | Siddiqui |
| 2024/0325685 A1 | 10/2024 | Daw et al. |
| 2025/0082897 A1 | 3/2025 | Pfleger |
| 2025/0114231 A1 | 4/2025 | Legaspi et al. |
| 2025/0288774 A1 | 9/2025 | Kulkarni et al. |
| 2025/0289618 A1 | 9/2025 | Simonsen et al. |
| 2025/0325785 A1 | 10/2025 | Kulkarni et al. |

FOREIGN PATENT DOCUMENTS

| | | |
|---|---|---|
| AU | 2022354188 A1 | 3/2024 |
| BR | PI0803737 A2 | 1/2010 |
| CA | 763930 A | 7/1967 |
| CA | 2770300 A1 | 2/2011 |
| CA | 2769026 C | 4/2015 |
| CA | 3083014 A1 | 5/2019 |
| CN | 1106744 A | 8/1995 |
| CN | 2907580 Y | 6/2007 |
| CN | 101035573 A | 9/2007 |
| CN | 101365501 A | 2/2009 |
| CN | 102939127 A | 2/2013 |
| CN | 102939129 A | 2/2013 |
| CN | 102973986 A | 3/2013 |
| CN | 102973987 A | 3/2013 |
| CN | 107088243 A | 8/2017 |
| CN | 111870742 A | 11/2020 |
| CN | 217015042 U | 7/2022 |
| CN | 116056746 A | 5/2023 |
| DE | 352014 C | 4/1922 |
| DE | 1913976 U | 4/1965 |
| DE | 4135502 C1 | 2/1993 |
| DE | 4303899 A1 | 8/1994 |
| DE | 19826746 C1 | 11/1999 |
| DE | 10038521 A1 | 2/2002 |
| DE | 10213411 A1 | 10/2003 |
| DE | 10259002 A1 | 10/2003 |
| DE | 10334372 A1 | 2/2005 |
| DE | 202005009946 U1 | 9/2005 |
| DE | 202005009947 U1 | 9/2005 |
| DE | 102007018275 A1 | 3/2008 |
| DE | 102009025347 A1 | 12/2010 |

(56)  References Cited

FOREIGN PATENT DOCUMENTS

| | | | |
|---|---|---|---|
| DE | 202012000538 | U1 | 3/2012 |
| DE | 202011107059 | U1 | 1/2013 |
| DE | 202013002466 | U1 | 3/2013 |
| DE | 102011085864 | A1 | 5/2013 |
| DE | 102012000844 | A1 | 7/2013 |
| DE | 102016120294 | A1 | 4/2018 |
| DE | 112018000170 | T5 | 10/2019 |
| EP | 0055023 | A2 | 6/1982 |
| EP | 0182409 | A1 | 5/1986 |
| EP | 0184629 | A2 | 6/1986 |
| EP | 0187846 | A1 | 7/1986 |
| EP | 0193406 | A2 | 9/1986 |
| EP | 0218203 | A1 | 4/1987 |
| EP | 0236458 | A1 | 9/1987 |
| EP | 247559 | A1 | 12/1987 |
| EP | 0252918 | A1 | 1/1988 |
| EP | 0298634 | A1 | 1/1989 |
| EP | 0303487 | A2 | 2/1989 |
| EP | 0335564 | A1 | 10/1989 |
| EP | 0352043 | A1 | 1/1990 |
| EP | 0390720 | A1 | 10/1990 |
| EP | 0407218 | A1 | 1/1991 |
| EP | 0217771 | B1 | 12/1991 |
| EP | 0471553 | A1 | 2/1992 |
| EP | 0479935 | A1 | 4/1992 |
| EP | 0528965 | A1 | 3/1993 |
| EP | 0553960 | A1 | 8/1993 |
| EP | 0590104 | A1 | 4/1994 |
| EP | 0598191 | A1 | 5/1994 |
| EP | 0663196 | A1 | 7/1995 |
| EP | 0677299 | A1 | 10/1995 |
| EP | 0680895 | A1 | 11/1995 |
| EP | 0685179 | A1 | 12/1995 |
| EP | 0699086 | A1 | 3/1996 |
| EP | 0767639 | A1 | 4/1997 |
| EP | 0768069 | A1 | 4/1997 |
| EP | 0795339 | A1 | 9/1997 |
| EP | 0815037 | A1 | 1/1998 |
| EP | 0909249 | A1 | 4/1999 |
| EP | 0923398 | A1 | 6/1999 |
| EP | 0935478 | A1 | 8/1999 |
| EP | 0959930 | A1 | 12/1999 |
| EP | 0977610 | A2 | 2/2000 |
| EP | 1018323 | A1 | 7/2000 |
| EP | 1023882 | A1 | 8/2000 |
| EP | 1047360 | A1 | 11/2000 |
| EP | 1115450 | A1 | 7/2001 |
| EP | 1131022 | A1 | 9/2001 |
| EP | 1175355 | A1 | 1/2002 |
| EP | 1237615 | A1 | 9/2002 |
| EP | 1245205 | A2 | 10/2002 |
| EP | 1308146 | A1 | 5/2003 |
| EP | 1321163 | A1 | 6/2003 |
| EP | 1347723 | A1 | 10/2003 |
| EP | 1406690 | A2 | 4/2004 |
| EP | 1409060 | A2 | 4/2004 |
| EP | 1090656 | B1 | 5/2004 |
| EP | 1420846 | A1 | 5/2004 |
| EP | 1420847 | A2 | 5/2004 |
| EP | 1427467 | A2 | 6/2004 |
| EP | 1485158 | A2 | 12/2004 |
| EP | 1498151 | A2 | 1/2005 |
| EP | 1567219 | A1 | 8/2005 |
| EP | 1578308 | A1 | 9/2005 |
| EP | 1145729 | B1 | 11/2005 |
| EP | 1606196 | A2 | 12/2005 |
| EP | 1615690 | A1 | 1/2006 |
| EP | 1629799 | A1 | 3/2006 |
| EP | 1629860 | | 3/2006 |
| EP | 1641510 | A1 | 4/2006 |
| EP | 1642610 | | 4/2006 |
| EP | 1642611 | | 4/2006 |
| EP | 1695678 | A1 | 8/2006 |
| EP | 1357868 | B1 | 9/2006 |
| EP | 1723980 | A2 | 11/2006 |
| EP | 1744803 | A2 | 1/2007 |
| EP | 1757251 | A2 | 2/2007 |
| EP | 1786501 | A2 | 5/2007 |
| EP | 1788990 | A1 | 5/2007 |
| EP | 1793938 | A1 | 6/2007 |
| EP | 1799163 | A1 | 6/2007 |
| EP | 1824534 | A2 | 8/2007 |
| EP | 1824549 | A2 | 8/2007 |
| EP | 1858575 | A1 | 11/2007 |
| EP | 1904003 | A2 | 4/2008 |
| EP | 1948279 | A1 | 7/2008 |
| EP | 1955683 | A1 | 8/2008 |
| EP | 2060296 | A1 | 5/2009 |
| EP | 2106821 | A1 | 10/2009 |
| EP | 2275058 | A1 | 1/2011 |
| EP | 2292293 | A1 | 3/2011 |
| EP | 2292294 | A1 | 3/2011 |
| EP | 2308542 | A1 | 4/2011 |
| EP | 2423125 | A1 | 2/2012 |
| EP | 2423126 | A1 | 2/2012 |
| EP | 2423127 | A1 | 2/2012 |
| EP | 2450076 | A1 | 5/2012 |
| EP | 2459264 | A1 | 6/2012 |
| EP | 2464411 | A1 | 6/2012 |
| EP | 2468347 | A1 | 6/2012 |
| EP | 2500056 | A2 | 9/2012 |
| EP | 2515988 | A1 | 10/2012 |
| EP | 2542291 | A1 | 1/2013 |
| EP | 1578468 | B1 | 4/2013 |
| EP | 2574354 | A1 | 4/2013 |
| EP | 2424470 | B1 | 8/2013 |
| EP | 2504054 | B1 | 9/2013 |
| EP | 2644224 | A2 | 10/2013 |
| EP | 1962937 | B1 | 8/2014 |
| EP | 2774648 | A1 | 9/2014 |
| EP | 2515985 | B1 | 12/2014 |
| EP | 2686054 | B1 | 12/2014 |
| EP | 2908897 | A1 | 8/2015 |
| EP | 2898918 | A3 | 9/2015 |
| EP | 2914222 | A1 | 9/2015 |
| EP | 2967968 | A1 | 1/2016 |
| EP | 1852139 | B1 | 5/2016 |
| EP | 2777747 | B1 | 5/2017 |
| EP | 3199130 | A1 | 8/2017 |
| EP | 3231471 | A1 | 10/2017 |
| EP | 3078393 | B1 | 11/2017 |
| EP | 3272385 | A1 | 1/2018 |
| EP | 3222316 | B1 | 5/2018 |
| EP | B352831 | A1 | 8/2018 |
| EP | 3250278 | A4 | 9/2018 |
| EP | 2782629 | B1 | 4/2019 |
| EP | 3313494 | B1 | 5/2019 |
| EP | 3478353 | A1 | 5/2019 |
| EP | 2826514 | B1 | 6/2019 |
| EP | 3490654 | A1 | 6/2019 |
| EP | 2946803 | B1 | 7/2019 |
| EP | B551103 | A1 | 10/2019 |
| EP | 3566739 | A1 | 11/2019 |
| EP | 3570925 | A1 | 11/2019 |
| EP | 3092024 | B1 | 12/2019 |
| EP | 3583972 | A2 | 12/2019 |
| EP | 3388103 | B1 | 1/2020 |
| EP | 3585460 | A1 | 1/2020 |
| EP | 3590573 | A1 | 1/2020 |
| EP | 3079752 | B1 | 4/2020 |
| EP | 3100758 | B1 | 4/2020 |
| EP | 2826515 | B1 | 5/2020 |
| EP | 3079748 | B1 | 5/2020 |
| EP | 3651844 | A1 | 5/2020 |
| EP | 3655081 | A1 | 5/2020 |
| EP | 2651485 | B1 | 6/2020 |
| EP | 3038690 | B1 | 7/2020 |
| EP | 3119464 | B1 | 9/2020 |
| EP | 3132823 | B1 | 9/2020 |
| EP | 3299056 | B1 | 9/2020 |
| EP | 3701993 | A1 | 9/2020 |
| EP | 3709940 | A1 | 9/2020 |
| EP | 3710095 | A1 | 9/2020 |
| EP | 3711806 | A1 | 9/2020 |

(56) References Cited

FOREIGN PATENT DOCUMENTS

| | | | |
|---|---|---|---|
| EP | 3711807 A1 | 9/2020 |
| EP | 3711808 A1 | 9/2020 |
| EP | 3713632 A2 | 9/2020 |
| EP | 3392167 B1 | 10/2020 |
| EP | 2468346 B1 | 11/2020 |
| EP | 3077031 B1 | 11/2020 |
| EP | 3738640 A1 | 11/2020 |
| EP | B756601 A1 | 12/2020 |
| EP | 3769803 A2 | 1/2021 |
| EP | 2995268 B1 | 3/2021 |
| EP | 3793627 A1 | 3/2021 |
| EP | 2968833 B1 | 5/2021 |
| EP | 3952973 A1 | 2/2022 |
| EP | 3082929 B1 | 3/2022 |
| EP | 3310421 B1 | 3/2022 |
| EP | 3725355 B1 | 5/2022 |
| EP | 2688629 B1 | 12/2022 |
| ES | 2645658 B1 | 10/2018 |
| FR | 1558162 A | 2/1969 |
| FR | 96086 E | 5/1972 |
| FR | 2127704 A5 | 10/1972 |
| FR | 2351634 A1 | 12/1977 |
| FR | 2731345 A1 | 9/1996 |
| FR | 2794638 A1 | 12/2000 |
| FR | 2855399 A1 | 12/2004 |
| FR | 3042716 B1 | 10/2021 |
| GB | 322426 A | 12/1929 |
| GB | 1131865 A | 10/1968 |
| GB | 2007507 A | 5/1979 |
| GB | 2106784 A | 4/1983 |
| GB | 2150938 A | 7/1985 |
| GB | 2187670 A | 9/1987 |
| GB | 2231801 A | 11/1990 |
| GB | 2239804 A | 7/1991 |
| GB | 2319507 | 5/1998 |
| GB | 2284764 B | 8/1998 |
| GB | 2427362 B | 9/2008 |
| GB | 2462267 A | 2/2010 |
| GB | 2469824 B | 8/2011 |
| GB | 2532459 B | 12/2016 |
| GB | 2565585 A | 2/2019 |
| GB | 2581356 A | 8/2020 |
| GB | 2561843 B | 9/2021 |
| JP | S5512265 B2 | 3/1980 |
| JP | S59218157 A | 12/1984 |
| JP | S59228856 A | 12/1984 |
| JP | 10218157 A | 1/1990 |
| JP | H09206370 A | 8/1997 |
| JP | H10151094 A | 6/1998 |
| JP | H10277144 A | 10/1998 |
| JP | 2001500414 A | 1/2001 |
| JP | 200150329 A | 2/2001 |
| JP | 2002530148 A | 9/2002 |
| JP | 2002282275 A | 10/2002 |
| JP | 2002543885 A | 12/2002 |
| JP | 2007501656 A | 2/2007 |
| JP | 2007167158 A | 7/2007 |
| JP | 2008-51549 A | 3/2008 |
| JP | 2008508077 A | 3/2008 |
| JP | 2008526377 A | 7/2008 |
| JP | 2009125583 A | 6/2009 |
| JP | 2010538106 A | 12/2010 |
| JP | 2011510110 A | 3/2011 |
| JP | 2013500125 | 1/2013 |
| JP | 2013515572 | 5/2013 |
| KR | 1020160035437 A | 3/2016 |
| RU | 2009105497 A | 8/2010 |
| WO | 1984001102 A1 | 3/1984 |
| WO | 198401296 A1 | 4/1984 |
| WO | 1986000816 A1 | 2/1986 |
| WO | 1986006284 A1 | 11/1986 |
| WO | 1987001582 A1 | 3/1987 |
| WO | 1989003232 A1 | 4/1989 |
| WO | 1989009626 A1 | 10/1989 |
| WO | 1990004431 A1 | 5/1990 |
| WO | 1991005577 A1 | 5/1991 |
| WO | 1991010466 A1 | 7/1991 |
| WO | 1991017728 A1 | 11/1991 |
| WO | 1992008426 A1 | 5/1992 |
| WO | 1992010220 A1 | 6/1992 |
| WO | 1992011826 A1 | 7/1992 |
| WO | 1992019192 A1 | 11/1992 |
| WO | 1993000054 A1 | 1/1993 |
| WO | 9311821 A1 | 6/1993 |
| WO | 9314806 A1 | 8/1993 |
| WO | 1994006377 A1 | 3/1994 |
| WO | 1994016747 A1 | 8/1994 |
| WO | 1994026215 A1 | 11/1994 |
| WO | 1995008968 A1 | 4/1995 |
| WO | 1995009667 A1 | 4/1995 |
| WO | 1995017862 A1 | 7/1995 |
| WO | 1995034253 A1 | 12/1995 |
| WO | 1996000541 A1 | 1/1996 |
| WO | 1996004119 A1 | 2/1996 |
| WO | 9607447 A1 | 3/1996 |
| WO | 1996019254 A1 | 6/1996 |
| WO | 1996026688 A1 | 9/1996 |
| WO | 1996030277 A1 | 10/1996 |
| WO | 1996034587 A1 | 11/1996 |
| WO | 9641653 A1 | 12/1996 |
| WO | 1996038192 A1 | 12/1996 |
| WO | 1996039096 A1 | 12/1996 |
| WO | 1997025947 A1 | 7/1997 |
| WO | 1997026937 A1 | 7/1997 |
| WO | 1997041811 A1 | 11/1997 |
| WO | 1998006642 | 2/1998 |
| WO | 1998011932 | 3/1998 |
| WO | 1998019729 | 5/1998 |
| WO | 9846176 A1 | 10/1998 |
| WO | 1999007313 A1 | 2/1999 |
| WO | 1999030761 A1 | 6/1999 |
| WO | 1999036009 A1 | 7/1999 |
| WO | 2000016843 | 3/2000 |
| WO | 2000025848 A2 | 5/2000 |
| WO | 0030696 A1 | 6/2000 |
| WO | 2000030575 A1 | 6/2000 |
| WO | 2000047494 A1 | 8/2000 |
| WO | 2001043807 A1 | 6/2001 |
| WO | 0152763 A1 | 7/2001 |
| WO | 2001093935 A1 | 12/2001 |
| WO | 2002036192 A1 | 5/2002 |
| WO | 2002053070 A1 | 7/2002 |
| WO | 2002060361 A2 | 8/2002 |
| WO | 03008028 A2 | 1/2003 |
| WO | 2003002177 | 1/2003 |
| WO | 2003002178 A2 | 1/2003 |
| WO | 2003008029 | 1/2003 |
| WO | 2003022333 A1 | 3/2003 |
| WO | 2003064279 A1 | 8/2003 |
| WO | 03092779 A1 | 11/2003 |
| WO | 03093357 A1 | 11/2003 |
| WO | 2004004611 A1 | 1/2004 |
| WO | 2004004796 A1 | 1/2004 |
| WO | 2004030722 A2 | 4/2004 |
| WO | 2004032992 A2 | 4/2004 |
| WO | 2004045696 | 6/2004 |
| WO | 2004050155 A1 | 6/2004 |
| WO | 2004052440 A1 | 6/2004 |
| WO | 2004056290 A1 | 7/2004 |
| WO | 2004056414 A1 | 7/2004 |
| WO | 2004056909 A1 | 7/2004 |
| WO | 2004075944 A2 | 9/2004 |
| WO | 2004089454 A1 | 10/2004 |
| WO | 2005004964 A1 | 1/2005 |
| WO | 2005014055 A2 | 2/2005 |
| WO | 2005061035 A1 | 7/2005 |
| WO | 2005092418 A1 | 10/2005 |
| WO | 2006005349 A2 | 1/2006 |
| WO | 2006009509 A1 | 1/2006 |
| WO | 2006009596 A1 | 1/2006 |
| WO | 2006017439 A2 | 2/2006 |
| WO | 2006021590 A1 | 3/2006 |
| WO | 2006027349 A1 | 3/2006 |
| WO | 2006033234 A1 | 3/2006 |

(56) References Cited

FOREIGN PATENT DOCUMENTS

| | | | |
|---|---|---|---|
| WO | 2006037321 | A1 | 4/2006 |
| WO | 2006097109 | A2 | 9/2006 |
| WO | 2006110695 | A2 | 10/2006 |
| WO | 2006112782 | A1 | 10/2006 |
| WO | 2006130776 | A2 | 12/2006 |
| WO | 2007001526 | A2 | 1/2007 |
| WO | 2007038988 | A1 | 4/2007 |
| WO | 2007050685 | | 5/2007 |
| WO | 2007083033 | A2 | 7/2007 |
| WO | 2008089770 | A1 | 7/2008 |
| WO | 2008104573 | A2 | 9/2008 |
| WO | 2008104603 | A1 | 9/2008 |
| WO | 2008138351 | A1 | 11/2008 |
| WO | 2008138352 | A1 | 11/2008 |
| WO | 2008151074 | A1 | 12/2008 |
| WO | 2009000277 | A1 | 12/2008 |
| WO | 2009012336 | A1 | 1/2009 |
| WO | 2009017541 | A1 | 2/2009 |
| WO | 2009043872 | A1 | 4/2009 |
| WO | 2009068043 | A2 | 6/2009 |
| WO | 2009080265 | A1 | 7/2009 |
| WO | 2009108243 | A1 | 9/2009 |
| WO | 2010006620 | A1 | 1/2010 |
| WO | 2010041084 | A1 | 4/2010 |
| WO | 2010054659 | A1 | 5/2010 |
| WO | 2010054666 | A1 | 5/2010 |
| WO | 2010129362 | A1 | 11/2010 |
| WO | 2010130261 | A1 | 11/2010 |
| WO | 2010149174 | A1 | 12/2010 |
| WO | 2010149175 | A1 | 12/2010 |
| WO | 2010151682 | A2 | 12/2010 |
| WO | 2011011023 | A1 | 1/2011 |
| WO | 2011014201 | A1 | 2/2011 |
| WO | 2011019359 | A1 | 2/2011 |
| WO | 2011026929 | A1 | 3/2011 |
| WO | 2011026930 | A1 | 3/2011 |
| WO | 2011063816 | A1 | 6/2011 |
| WO | 2011073403 | A1 | 6/2011 |
| WO | 2011076211 | A1 | 6/2011 |
| WO | 2011079129 | A1 | 6/2011 |
| WO | 2011109393 | A1 | 9/2011 |
| WO | 2012016570 | A2 | 2/2012 |
| WO | 2012016571 | A2 | 2/2012 |
| WO | 2012079590 | A1 | 6/2012 |
| WO | 2012085124 | A1 | 6/2012 |
| WO | 2012126474 | A1 | 9/2012 |
| WO | 2012134804 | A1 | 10/2012 |
| WO | 2012139214 | A1 | 10/2012 |
| WO | 2013010745 | A1 | 1/2013 |
| WO | 2013029621 | A1 | 3/2013 |
| WO | 2013075725 | A1 | 5/2013 |
| WO | 2014062225 | A1 | 4/2014 |
| WO | 2014081859 | A1 | 5/2014 |
| WO | 2014142917 | A1 | 9/2014 |
| WO | 2014142923 | A1 | 9/2014 |
| WO | 2014165046 | A1 | 10/2014 |
| WO | 15069843 | A2 | 5/2015 |
| WO | 2015075841 | A1 | 5/2015 |
| WO | 15090338 | A1 | 6/2015 |
| WO | 2015089189 | A2 | 6/2015 |
| WO | 2015105942 | A1 | 7/2015 |
| WO | 15142506 | A1 | 9/2015 |
| WO | 2015184365 | A1 | 12/2015 |
| WO | 201603323 | A1 | 1/2016 |
| WO | 2016008493 | A1 | 1/2016 |
| WO | 2016116915 | A1 | 7/2016 |
| WO | 2016206701 | A1 | 12/2016 |
| WO | 2017185052 | A1 | 10/2017 |
| WO | 2018029279 | A1 | 2/2018 |
| WO | 2018059637 | A1 | 4/2018 |
| WO | 2018134748 | A1 | 7/2018 |
| WO | 2018150975 | A1 | 8/2018 |
| WO | 2018156589 | A2 | 8/2018 |
| WO | 2018219433 | A1 | 12/2018 |
| WO | 2019002066 | A2 | 1/2019 |
| WO | 2019014344 | A1 | 1/2019 |
| WO | 2019070984 | A1 | 4/2019 |
| WO | 2019083104 | A1 | 5/2019 |
| WO | 2019083839 | A1 | 5/2019 |
| WO | 2019099845 | A1 | 5/2019 |
| WO | 2019099975 | A2 | 5/2019 |
| WO | 2019113203 | A1 | 6/2019 |
| WO | 2019123004 | A1 | 6/2019 |
| WO | 2019245679 | A1 | 12/2019 |
| WO | 2020006527 | A1 | 1/2020 |
| WO | 2020015804 | A1 | 1/2020 |
| WO | 2020106822 | A1 | 5/2020 |
| WO | 2020125908 | A1 | 6/2020 |
| WO | 2020223146 | A1 | 11/2020 |
| WO | 2020237286 | A1 | 12/2020 |
| WO | 2020251961 | A1 | 12/2020 |
| WO | 2020252003 | A1 | 12/2020 |
| WO | 2020263859 | A1 | 12/2020 |
| WO | 2021034487 | A1 | 2/2021 |
| WO | 2021041048 | A1 | 3/2021 |
| WO | 2021041703 | A1 | 3/2021 |
| WO | 2021051158 | A1 | 3/2021 |
| WO | 2021077103 | A1 | 4/2021 |
| WO | 2021087099 | A1 | 5/2021 |
| WO | 2021092271 | A1 | 5/2021 |
| WO | 2021097519 | A1 | 5/2021 |
| WO | 2021108115 | A1 | 6/2021 |
| WO | 2021115840 | A1 | 6/2021 |
| WO | 2021127040 | A1 | 6/2021 |
| WO | 2021183718 | A1 | 9/2021 |
| WO | 2022031520 | A1 | 2/2022 |
| WO | 2022031550 | A1 | 2/2022 |
| WO | 2022056263 | A2 | 3/2022 |
| WO | 2022223978 | A1 | 10/2022 |
| WO | 2022223980 | A1 | 10/2022 |
| WO | 2022223983 | A1 | 10/2022 |
| WO | 2022223985 | A1 | 10/2022 |
| WO | 2022223987 | A1 | 10/2022 |
| WO | 2022260831 | A1 | 12/2022 |
| WO | 2023003682 | A1 | 1/2023 |
| WO | 2023055832 | A1 | 4/2023 |
| WO | 2023180707 | A1 | 9/2023 |
| WO | 2023211421 | A1 | 11/2023 |
| WO | 2024112323 | A1 | 5/2024 |
| WO | 2024112324 | A1 | 5/2024 |
| WO | 2024112325 | A1 | 5/2024 |
| WO | 2024112799 | A1 | 5/2024 |
| WO | 2024112805 | A1 | 5/2024 |

OTHER PUBLICATIONS

PCT/US2022/045084 filed Sep. 28, 2022 International Search Report and Written Opinion dated Jan. 3, 2023.

PCT/US2023/080761 filed Nov. 21, 2023 International Search Report and Written Opinion dated Apr. 9, 2024.

PCT/US2023/080769 filed Nov. 21, 2023 International Search Report and Written Opinion dated Mar. 15, 2024.

PCT/US2025/019799 filed Mar. 13, 2025 International Search Report and Written Opinion dated Jun. 4, 2025.

U.S. Appl. No. 18/019,464, filed Feb. 2, 2023 Non-Final Office Action dated Jul. 30, 2025.

U.S. Appl. No. 18/019,464, filed Feb. 2, 2023 Restriction Requirement dated May 6, 2025.

U.S. Appl. No. 18/019,647, filed Feb. 3, 2023 Non-Final Office Action dated Jul. 31, 2025.

U.S. Appl. No. 18/019,647, filed Feb. 3, 2023 Restriction Requirement dated May 8, 2025.

U.S. Appl. No. 18/604,394, filed Mar. 13, 2024 Non-Final Office Action dated Jul. 15, 2025.

PCT/US2022/026177 filed Apr. 25, 2022 International Search Report & Written Opinion dated Mar. 20, 2023.

U.S. Appl. No. 17/796,611, filed Jul. 29, 2022 Non-Final Office Action dated Mar. 20, 2025.

"Medifilm." Datasheet [online]. Mylan Technologies Inc., 2003 [retrieved on Feb. 14, 2020]. Retrieved from the Internet: <URL: https://web.archive.org/web/20030205090818/http://www.mylantech.com/products/medifilm.html>.

(56)         References Cited

OTHER PUBLICATIONS

"Tripartite Biocompatibility Guidance for Medical Devices," DSMA (Apr. 24, 1987).
Akzo Nobel, "Ethomeen C/25 technical data sheet" Mar. 10, 2009.
Amirkhai Il et al., "Nitric Oxide Complexes of Trimethylaluminium" Journal of Organometallic Chemistry, 149 (1978).
ANGUS "Chemie GmbHTechnical Data Sheet", AMP-95, TDS 10A (2000).
AU 2014248744 filed Jul. 9, 2015 Examiner's Report dated Jul. 26, 2017.
AU 2015306630 filed Feb. 2, 2017 Office Action dated Aug. 2, 2018.
BR PI 0506836-3 filed Jan. 18, 2005, Technical Report dated Jul. 28, 2015.
BR1120170040301 filed Feb. 21, 2017 Office Action dated Aug. 20, 2019.
CA 2,769,026 filed Jan. 24, 2012 First Examination Report dated Nov. 4, 2013.
CN 201080058895.4 filed Jun. 21, 2012 First Office Action dated Feb. 27, 2014.
CN 201080058895.4 filed Jun. 21, 2012 Second Office Action dated Nov. 3, 2014.
CN 201080058895.4 filed Jun. 21, 2012 Third Office Action dated May 4, 2015.
CN 201480013064.3 filed Sep. 8, 2015 Office Action dated Jun. 29, 2017.
CN 201480013064.3 filed Sep. 8, 2015 Office Action dated Oct. 10, 2016.
CN 20158004662.3 filed Feb. 24, 2017 Office Action dated Jul. 8, 2019.
CN 20158004662.3 filed Feb. 24, 2017 Office Action dated Sep. 20, 2019.
EP 09848341.5 filed Feb. 27, 2012 extended European Search Report dated Apr. 4, 2013.
EP 09848341.5 filed Feb. 27, 2012 supplemental European Search Report dated Nov. 8, 2013.
EP 10840071.4 filed Jul. 4, 2012 Exam Report dated Apr. 29, 2014.
EP 10840071.4 filed Jul. 4, 2012 extended European Search Report dated Apr. 17, 2013.
EP 10840071.4 filed Jul. 4, 2012 Notice of Opposition dated Apr. 24, 2017.
EP 10840071.4 filed Jul. 4, 2012 Office Action dated Jul. 9, 2015.
EP 11751198.0 filed Sep. 28, 2012 Exam Report dated Feb. 7, 2014.
EP 11751198.0 filed Sep. 28, 2012 extended European search report dated Jul. 9, 2013.
EP 14779919.1 filed Sep. 10, 2015 Extended European Search Report dated Aug. 23, 2016.
EP 14779919.1 filed Sep. 10, 2015 Office Action dated Jul. 4, 2017.
EP 15836062.8 filed Feb. 17, 2017 Extended European Search Report dated Feb. 20, 2018.
EP 15836062.8 filed Feb. 17, 2017 Office Action dated Feb. 19, 2019.
EP 16171279.9 filed May 25, 2016 Extended European Search Report, dated Aug. 23, 2016.
EP 16171279.9 filed May 25, 2016 Intent to Grant, dated Jun. 13, 2017.
EP 17201044.9 filed Nov. 10, 2017 Extended European Search Report dated Jan. 18, 2018.
EP 17201044.9 filed Nov. 10, 2017 Office Action dated Jul. 4, 2019.
Hollister, "Vapro intermittent catheter brochure" (2009).
Johnson et al. "Activities of a Nitrofurazone-Containing Urinary Catheter and a Silver Hydrogel Catheter against Multidrug-Resistant Bacteria Characteristic of Catheter-Associated Urinary Tract Infection" Antimicrobial Agents and Chemotherapy, Dec. 1999.
JP 2012-546157 filed Jun. 12, 2012 Decision of Rejection dated Aug. 21, 2015.
JP 2012-546157 filed Jun. 12, 2012 First Office Action dated Sep. 16, 2014.
JP 2015-243156 filed Dec. 14, 2015 Office Action dated Sep. 16, 2016.
JP 2016-501444 filed Sep. 11, 2015 Office Action dated Dec. 14, 2017.
JP 2017-511223 filed Feb. 24, 2017 Office Action dated Jun. 4, 2019.
Lubrizol, "Neutralizing Carbopol® * and Pemulen™ * Polymers in Aqueous and Hydroalcoholic Systems" Technical Data Sheet TDS-237 Edition: Sep. 16, 2009.
Moore et al., "The Swelling of Cotton in Water: A Microscopical Study," Textile Research Journal, vol. 20, Issue 9 pp. 620-630, Sep. 1, 1950.
MX/a/2015/009904 filed Jul. 30, 2015 Office Action dated Jun. 29, 2018.
MX/a/2017/002457 filed Feb. 23, 2017 Office Action dated Sep. 4, 2019.
Newman "Intermittent Catheterization and Current Best Practices: Catheter Design and Types"; http://www.medscape.com/viewarticle/745908_8, last accessed May 31, 2013.
Newman et al. "Review of Intermittent Catheterization and Current Best Practices," Urological Nursing, vol. 31, No. 1 pp. 12-29, 48, Jan. 2011.
Norton, J.A. et al., Surgery: Basic Science and Clinical Evidence Springer, 2nd ed., 2008, p. 281.
PCT/US2006/041633 filed Oct. 25, 2006 International Preliminary Report on Patentability dated Mar. 24, 2009.
PCT/US2006/041633 filed Oct. 25, 2006 Search Report dated Aug. 12, 2008.
PCT/US2006/041633 filed Oct. 25, 2006 Written Opinion dated Aug. 12, 2008.
U.S. Appl. No. 13/662,278, filed Oct. 26, 2012 Examiner's Answer dated Jun. 2, 2017.
U.S. Appl. No. 13/662,278, filed Oct. 26, 2012 Final Office Action dated Feb. 20, 2015.
U.S. Appl. No. 13/662,278, filed Oct. 26, 2012 Final Office Action dated Oct. 19, 2016.
U.S. Appl. No. 13/662,278, filed Oct. 26, 2012 Non-Final Office Action dated Jul. 7, 2016.
U.S. Appl. No. 13/662,278, filed Oct. 26, 2012 Non-Final Office Action dated Sep. 12, 2014.
U.S. Appl. No. 13/662,278, filed Oct. 26, 2012 Non-Final Office Action dated Sep. 17, 2015.
U.S. Appl. No. 13/802,095, filed Mar. 13, 2013 Non-Final Office Action dated Aug. 15, 2014.
U.S. Appl. No. 13/802,095, filed Mar. 13, 2013 Notice of Allowance dated Nov. 28, 2014.
U.S. Appl. No. 14/681,023, filed Apr. 7, 2015 Non-Final Office Action dated Nov. 9, 2016.
U.S. Appl. No. 14/681,023, filed Apr. 7, 2015 Notice of Allowance dated Mar. 8, 2017.
U.S. Appl. No. 14/707,954, filed May 8, 2015 Non-Final Office Action dated Dec. 1, 2016.
U.S. Appl. No. 15/506,723, filed Feb. 24, 2017 Final Office Action dated Dec. 9, 2019.
U.S. Appl. No. 15/506,723, filed Feb. 24, 2017 Non-Final Office Action dated Aug. 27, 2019.
U.S. Appl. No. 15/506,723, filed Feb. 24, 2017 Notice of Allowance dated Jul. 29, 2020.
U.S. Appl. No. 15/639,844, filed Jun. 30, 2017 Non-Final Office Action dated Jul. 10, 2019.
U.S. Appl. No. 15/639,844, filed Jun. 30, 2017 Notice of Allowance dated Aug. 13, 2019.
U.S. Appl. No. 15/669,697, filed Aug. 4, 2017 Non-Final Office Action dated Oct. 18, 2018.
U.S. Appl. No. 15/669,697, filed Aug. 4, 2017 Notice of Allowance dated Mar. 1, 2019.
U.S. Appl. No. 15/724,879, filed Oct. 4, 2017 Advisory Action dated Jan. 29, 2019.
U.S. Appl. No. 15/724,879, filed Oct. 4, 2017 Examiner's Answer dated Jul. 25, 2019.
U.S. Appl. No. 15/724,879, filed Oct. 4, 2017 Final Office Action dated Dec. 4, 2018.

(56) References Cited

OTHER PUBLICATIONS

U.S. Appl. No. 15/724,879, filed Oct. 4, 2017 Non-Final Office Action dated Jul. 19, 2018.
U.S. Appl. No. 15/724,879, filed Oct. 4, 2017 Notice of Allowance dated Aug. 14, 2020.
U.S. Appl. No. 15/724,879, filed Oct. 4, 2017 PTAB Decision on Appeal dated Jul. 1, 2020.
U.S. Appl. No. 15/724,879, filed Oct. 4, 2017 Restriction Requirement dated Mar. 7, 2018.
U.S. Appl. No. 16/453,809, filed Jun. 26, 2019 Notice of Allowance dated Apr. 14, 2020.
U.S. Appl. No. 17/114,275, filed Dec. 7, 2020 Final Office Action dated May 23, 2023.
U.S. Appl. No. 17/114,275, filed Dec. 7, 2020 Non-Final Office Action dated Jan. 31, 2023.
U.S. Appl. No. 17/114,275, filed Dec. 7, 2020 Notice of Allowance dated Aug. 9, 2023.
Wong, "Hydrogels, water-absorbing polymers" Catalyst, vol. 18, Issue 1, pp. 18-21, Sep. 2007.
PCT/US2021/043771 filed Jul. 29, 2021 International Search Report and Written Opinion dated Jan. 24, 2022.
PCT/US2021/044021 filed Jul. 30, 2021 International Search Report and Written Opinion dated Jan. 24, 2022.
PCT/US2021/049867 filed Sep. 10, 2021 International Search Report and Written Opinion dated Mar. 11, 2022.
PCT/US2009/055389 filed Aug. 28, 2009 International Search Report dated Oct. 20, 2009.
PCT/US2009/055389 filed Aug. 28, 2009 Written Opinion dated Oct. 20, 2009.
PCT/US2009/055395 filed Aug. 28, 2009 International Preliminary Report on Patentability dated Jan. 31, 2012.
PCT/US2009/055395 filed Aug. 28, 2009 International Search Report dated Oct. 15, 2009.
PCT/US2009/055395 filed Aug. 28, 2009 Written Opinion dated Oct. 15, 2009.
PCT/US2010/061597 filed Dec. 21, 2010 International Preliminary Report on Patentability dated Jun. 26, 2012 and Written Opinion dated Feb. 28, 2011.
PCT/US2010/061597 filed Dec. 21, 2010 International Search Report dated Feb. 28, 2011.
PCT/US2011/026681 filed Mar. 1, 2011 International Preliminary Report on Patentability dated Sep. 4, 2012.
PCT/US2011/026681 filed Mar. 1, 2011 International Search Report dated Apr. 27, 2011.
PCT/US2011/026681 filed Mar. 1, 2011 Written Opinion dated Apr. 27, 2011.
PCT/US2014/024231 filed Mar. 12, 2014 International Search Report and Written Opinion dated Jul. 10, 2014.
PCT/US2022/029431 filed May 16, 2022 International Search Report and Written Opinion dated Sep. 15, 2022.
PCT/US2022/035565 filed Jun. 29, 2022 International Search Report and Written Opinion dated Sep. 27, 2022.
PCTUS2018054378 filed Oct. 4, 2018 International Preliminary Report on Patentability dated Jan. 2, 2019.
PCTUS2018054378 filed Oct. 4, 2018 International Search Report and Written opinion dated Jan. 2, 2019.
Peppas, "Hydrogels," Biomaterial Science: An Introduction to Materials in Medicine. 2nd Edition, pp. 100-107, Aug. 18, 2004.
Piyush Gupta et al. Hydrogels: from controlled release to pH-responsive drug delivery, May 2002, DDT vol. 7, No. 10, pp. 569-579. (Year: 2002).
RU 2015140616 filed Sep. 24, 2015 Office Action dated Feb. 21, 2018.
U.S. Appl. No. 12/091,916, filed Feb. 2, 2009 Final Office Action dated Sep. 22, 2011.
U.S. Appl. No. 12/091,916, filed Feb. 2, 2009 Non-Final Office Action dated May 10, 2011.
U.S. Appl. No. 12/091,916, filed Feb. 2, 2009 Non-Final Office Action dated Nov. 24, 2010.

U.S. Appl. No. 12/091,916, filed Feb. 2, 2009 Notice of Allowance dated Aug. 17, 2012.
U.S. Appl. No. 13/387,447, filed Mar. 22, 2012 Advisory Action dated Feb. 27, 2014.
U.S. Appl. No. 13/387,447, filed Mar. 22, 2012 Examiner's Answer dated Oct. 5, 2016.
U.S. Appl. No. 13/387,447, filed Mar. 22, 2012 Final Office Action dated Dec. 11, 2013.
U.S. Appl. No. 13/387,447, filed Mar. 22, 2012 Final Office Action dated Oct. 31, 2014.
U.S. Appl. No. 13/387,447, filed Mar. 22, 2012 Final Office Action dated Oct. 5, 2015.
U.S. Appl. No. 13/387,447, filed Mar. 22, 2012 Non-Final Office Action dated Jan. 15, 2013.
U.S. Appl. No. 13/387,447, filed Mar. 22, 2012 Non-Final Office Action dated Jul. 15, 2014.
U.S. Appl. No. 13/387,447, filed Mar. 22, 2012 Non-Final Office Action dated Jun. 6, 2013.
U.S. Appl. No. 13/387,447, filed Mar. 22, 2012 Non-Final Office Action dated Mar. 12, 2015.
U.S. Appl. No. 13/387,447, filed Mar. 22, 2012 Notice of Allowance dated Jul. 30, 2018.
U.S. Appl. No. 13/387,447, filed Mar. 22, 2012 Patent Board Decision dated Jun. 1, 2018.
U.S. Appl. No. 13/389,753, filed Mar. 20, 2012 Decision on Appeal dated Jun. 29, 2017.
U.S. Appl. No. 13/389,753, filed Mar. 20, 2012 Examiner's Answer dated Aug. 27, 2015.
U.S. Appl. No. 13/389,753, filed Mar. 20, 2012 Final Office Action dated Dec. 10, 2014.
U.S. Appl. No. 13/389,753, filed Mar. 20, 2012 Non-Final Office Action dated Jul. 21, 2014.
U.S. Appl. No. 13/389,753, filed Mar. 20, 2012 Notice of Allowance dated Jul. 5, 2017.
U.S. Appl. No. 13/516,660, filed Aug. 27, 2012 Advisory Action dated Nov. 19, 2019.
U.S. Appl. No. 13/516,660, filed Aug. 27, 2012 Advisory Action dated Sep. 22, 2016.
U.S. Appl. No. 13/516,660, filed Aug. 27, 2012 Board Decision dated Jan. 22, 2019.
U.S. Appl. No. 13/516,660, filed Aug. 27, 2012 Examiner's Answer dated Nov. 22, 2017.
U.S. Appl. No. 13/516,660, filed Aug. 27, 2012 Final Office Action dated Jun. 29, 2016.
U.S. Appl. No. 13/516,660, filed Aug. 27, 2012 Final Office Action dated Sep. 9, 2019.
U.S. Appl. No. 13/516,660, filed Aug. 27, 2012 Non-Final Office Action dated Jan. 8, 2020.
U.S. Appl. No. 13/516,660, filed Aug. 27, 2012 Non-Final Office Action dated Mar. 15, 2019.
U.S. Appl. No. 13/516,660, filed Aug. 27, 2012 Non-Final Office Action dated Mar. 8, 2016.
U.S. Appl. No. 13/516,660, filed Aug. 27, 2012 Notice of Allowance dated Oct. 27, 2020.
U.S. Appl. No. 13/582,698, filed Sep. 4, 2012 Non-Final Office Action dated Sep. 24, 2014.
U.S. Appl. No. 13/662,278, filed Oct. 26, 2012 Board Decision dated Aug. 23, 2018.
PCT/US2022/050645 filed Nov. 21, 2022 International Search Report and Written Opinion dated Jun. 28, 2023.
PCT/US2022/050646 filed Nov. 21, 2022 International Search Report and Written Opinion dated May 30, 2023.
PCT/US2022/050648 filed Nov. 21, 2022 International Search Report and Written Opinion dated Jun. 16, 2023.
PCT/US2025/023972 filed Apr. 9, 2025 International Search Report and Written Opinion dated Sep. 18, 2025.
U.S. Appl. No. 17/796,611, filed Jul. 29, 2022 Advisory Action dated Nov. 28, 2025.
U.S. Appl. No. 17/796,611, filed Jul. 29, 2022 Final Office Action dated Sep. 24, 2025.
U.S. Appl. No. 18/019,464, filed Feb. 2, 2023 Notice of Allowance dated Nov. 25, 2025.

(56)  References Cited

OTHER PUBLICATIONS

U.S. Appl. No. 18/019,647, filed Feb. 3, 2023 Non-Final Office Action dated Nov. 17, 2025.
U.S. Appl. No. 18/536,063, filed Dec. 11, 2023 Non-Final Office Action dated Nov. 12, 2025.
U.S. Appl. No. 18/641,181, filed Apr. 19, 2024 Restriction Requirement dated Oct. 21, 2025.

* cited by examiner

INTERMITTENT-CATHETER ASSEMBLY AND METHODS THEREOF

PRIORITY

This application is a U.S. national stage of International Patent Application No. PCT/US2021/049867, filed Sep. 10, 2021, which claims the benefit of priority to U.S. Provisional Patent Application No. 63/077,469, filed Sep. 11, 2020, each of which is incorporated by reference in its entirety into this application.

BACKGROUND

Users of urinary catheters such as intermittent catheters self-catheterize four to six times a day. As such, a simple-to-use intermittent catheter that ensures sterility before use and facilitates cleanliness after use is needed.

Disclosed herein are intermittent-catheter assemblies and methods thereof that address the foregoing.

SUMMARY

Disclosed herein is an intermittent-catheter assembly including, in some embodiments, an intermittent catheter and a catheter housing. The intermittent catheter includes a funnel and a catheter tube fluidly coupled to the funnel. The catheter housing includes the intermittent catheter disposed in the catheter housing while in a packaged state of the intermittent-catheter assembly. The catheter housing includes an inner sleeve and an outer sleeve. The inner sleeve includes a longitudinal cavity containing a majority of the intermittent catheter in the packaged state of the intermittent-catheter assembly. The outer sleeve is slidably disposed over the inner sleeve. The catheter housing is configured to expose the intermittent catheter for removal from the catheter housing when the outer sleeve is grasped and slid toward an exposed end of the inner sleeve in opposition to a force applied to the exposed end of the inner sleeve.

In some embodiments, the inner sleeve includes longitudinal ribs extending into the longitudinal cavity. The ribs stabilize the intermittent catheter in the inner sleeve in the packaged state of the intermittent-catheter assembly.

In some embodiments, the catheter housing further includes a displaceable cap sealing an opening of the outer sleeve opposite the exposed end of the inner sleeve. The cap seals the opening of the outer sleeve and maintains sterility of the intermittent catheter in the packaged state of the intermittent-catheter assembly.

In some embodiments, the cap sits in a seat formed within the opening of the outer sleeve, the cap tethered to the inner sleeve by a tether.

In some embodiments, the tether is a polymeric ribbon. The ribbon includes an opening configured to weaken a structural integrity of the ribbon around the opening such that the ribbon and the cap tethered thereto bend away from a centerline of the catheter housing as the outer sleeve is slid toward the exposed end of the inner sleeve. So configured, the ribbon facilitates access to the intermittent catheter.

In some embodiments, the cap includes an annular gasket disposed in a recess around a rim of the cap. The gasket sits between the cap and the outer sleeve securing the cap in the outer sleeve in the packaged state of the intermittent-catheter assembly.

In some embodiments, the cap includes a funnel insert along a centerline of the cap. The funnel insert is inserted into the funnel of the intermittent catheter in the packaged state of the intermittent-catheter assembly, which stabilizes the intermittent catheter in the inner sleeve.

In some embodiments, the cap sits on a seat formed around the opening of the outer sleeve in the packaged state of the intermittent-catheter assembly. The cap is coupled to the outer sleeve by a living hinge.

In some embodiments, the cap and the outer sleeve include complementary snap-fit features securing the cap on the outer sleeve in the packaged state of the intermittent-catheter assembly.

In some embodiments, the inner sleeve includes a longitudinal side opening to the longitudinal cavity. The inner sleeve includes an end cap integrated into the inner sleeve opposite the exposed end of the inner sleeve.

In some embodiments, a connecting portion of the inner sleeve is coterminous with ends of the side opening. The connecting portion is molded with a bias such that the connecting portion and the end cap coupled thereto bend away from a centerline of the catheter housing as the outer sleeve is slid toward the exposed end of the inner sleeve. So configured, the connecting portion facilitates access to the intermittent catheter.

In some embodiments, the intermittent-catheter assembly further includes a drainage bag. The drainage bag is fluidly coupled to the funnel for voiding urine into the drainage bag upon catheterization with the intermittent catheter.

Also disclosed herein is an intermittent-catheter assembly including, in some embodiments, an intermittent catheter and a catheter housing. The intermittent catheter includes a funnel and a catheter tube fluidly coupled to the funnel. The catheter housing includes the intermittent catheter disposed in the catheter housing while in a packaged state of the intermittent-catheter assembly. The catheter housing includes a sleeve and a cap. The sleeve includes a longitudinal cavity containing a majority of the intermittent catheter in the packaged state of the intermittent-catheter assembly. The cap is coupled to the sleeve by a living hinge. The cap seals an opening of the sleeve opposite a closed end of the sleeve. The cap seals the opening of the sleeve and maintains sterility of the intermittent catheter in the packaged state of the intermittent-catheter assembly.

In some embodiments, the opening includes a longitudinal extension into the sleeve. The longitudinal extension into the sleeve is configured to expose a longitudinal portion of the funnel when the cap is moved from a closed position in the packaged state of the intermittent-catheter assembly to an open position about the living hinge.

In some embodiments, the cap includes a pull tab coupled to the cap on a same side of the catheter housing as the living hinge. A portion of the pull tab is configured to peel away from the cap toward an opposite side of the catheter housing from the living hinge when the pull tab is initially pulled to extend a lever arm with respect to the living hinge sufficient for subsequently pulling the cap away from the opening of the sleeve by the pull tab.

In some embodiments, the cap includes a push tab extending from an opposite side of the catheter housing from the living hinge. The push tab is configured to extend a lever arm with respect to the living hinge sufficient for pushing the cap away from the opening of the sleeve by the push tab.

In some embodiments, the cap includes a push button. The push button is configured to deform the cap and disengage complementary snap-fit features between the cap and the sleeve for subsequently pushing the cap away from the opening of the sleeve by the push button.

In some embodiments, the intermittent-catheter assembly further includes a drainage bag. The drainage bag is fluidly coupled to the funnel for voiding urine into the drainage bag upon catheterization with the intermittent catheter.

Also disclosed herein is an intermittent-catheter assembly including, in some embodiments, an intermittent catheter and a catheter housing. The intermittent catheter includes a funnel and a catheter tube fluidly coupled to the funnel. The catheter housing includes the intermittent catheter disposed in the catheter housing while in a packaged state of the intermittent-catheter assembly. The catheter housing includes a sleeve and a removable cap. The sleeve includes a longitudinal cavity containing a majority of the intermittent catheter in the packaged state of the intermittent-catheter assembly. The cap includes another longitudinal cavity configured to contain a remainder of the intermittent catheter. The cap seals an opening of the sleeve opposite a closed end of the sleeve. The cap seals the opening of the sleeve and maintains sterility of the intermittent catheter in the packaged state of the intermittent-catheter assembly.

In some embodiments, the sleeve includes longitudinal ribs extending into the longitudinal cavity. The ribs stabilize the intermittent catheter in the sleeve in the packaged state of the intermittent-catheter assembly.

In some embodiments, the sleeve is approximately coextensive with the catheter tube and the cap is approximately coextensive with the funnel.

In some embodiments, the cap and the sleeve include complementary snap-fit features. The snap-fit features secure the cap on the sleeve in the packaged state of the intermittent-catheter assembly.

In some embodiments, the intermittent-catheter assembly further includes shrink-wrap packaging over an entirety of the cap and at least a portion of the sleeve. The packaging includes a pull tab extending from the packaging configured to break open the packaging when the pull tab is pulled.

In some embodiments, the cap includes internal threads about an open-ended portion of the cap and the sleeve includes complementary external threads about an open-ended portion of the sleeve including the opening. The cap includes recesses or ribs around the cap configured to facilitate gripping and screwing the cap off the sleeve.

In some embodiments, the intermittent-catheter assembly further includes a drainage bag. The drainage bag is fluidly coupled to the funnel for voiding urine into the drainage bag upon catheterization with the intermittent catheter.

Also disclosed herein is an intermittent-catheter assembly including, in some embodiments, an intermittent catheter and a catheter housing. The intermittent catheter includes a funnel and a catheter tube fluidly coupled to the funnel. The catheter housing includes the intermittent catheter disposed in the catheter housing while in a packaged state of the intermittent-catheter assembly. The catheter housing includes a sleeve, a reinforcing insert, and an adhesive tab. The sleeve includes a longitudinal cavity containing a majority of the intermittent catheter in the packaged state of the intermittent-catheter assembly. The reinforcing insert is suspended in a longitudinal sleeve gap. The reinforcing insert includes a longitudinal insert gap such that the sleeve gap and the insert gap combine to provide major-side openings for grasping the funnel and removing the intermittent catheter from the catheter housing. The adhesive tab covers the major-side openings of the catheter housing.

In some embodiments, the reinforcing insert includes major-side protrusions from which the reinforcing insert is suspended in the sleeve gap.

In some embodiments, the reinforcing insert includes minor-side protrusions from which the reinforcing insert is suspended in the sleeve gap.

In some embodiments, the intermittent-catheter assembly further includes a drainage bag. The drainage bag is fluidly coupled to the funnel for voiding urine into the drainage bag upon catheterization with the intermittent catheter.

Also disclosed herein is an intermittent-catheter assembly including, in some embodiments, an intermittent catheter and a catheter housing. The intermittent catheter includes a funnel and a catheter tube fluidly coupled to the funnel. The catheter housing includes the intermittent catheter disposed in the catheter housing while in a packaged state of the intermittent-catheter assembly for maintaining sterility of the intermittent catheter. The catheter housing includes an end piece, a collapsible sheath, a pull tab, and a removable cap. The collapsible sheath includes a distal portion coupled to the end piece and a proximal portion coupled to the funnel. An entirety of the catheter tube is disposed in the collapsible sheath in the packaged state of the intermittent-catheter assembly. The pull tab seals a distal opening of the end piece in the packaged state of the intermittent-catheter assembly. The removable cap seals a proximal opening of the funnel in the packaged state of the intermittent-catheter assembly.

In some embodiments, the intermittent-catheter assembly further includes a drainage bag. The drainage bag is fluidly coupled to the funnel for voiding urine into the drainage bag upon catheterization with the intermittent catheter.

Also disclosed herein is an intermittent-catheter assembly including, in some embodiments, an intermittent catheter and a catheter housing. The intermittent catheter includes a funnel and a catheter tube fluidly coupled to the funnel. The catheter housing includes the intermittent catheter disposed in the catheter housing while in a packaged state of the intermittent-catheter assembly for maintaining sterility of the intermittent catheter. The catheter housing includes a bottle and a pull tab. The bottle includes a neck. An entirety of the catheter tube is disposed in the bottle with the funnel fitted into the neck in the packaged state of the intermittent-catheter assembly. The pull tab seals the intermittent catheter in the bottle in the packaged state of the intermittent-catheter assembly.

In some embodiments, a proximal opening of the funnel and a proximal opening of the bottle are concentric. Being concentric, the pull tab simultaneously seals the funnel and the bottle in the packaged state of the intermittent-catheter assembly.

In some embodiments, the bottle is configured to be fluidly coupled to the funnel for voiding urine into the bottle upon catheterization with the intermittent catheter.

Also disclosed herein is a method of an intermittent-catheter assembly including, in some embodiments, a catheter assembly-obtaining step, an intermittent catheter-exposing step, an intermittent catheter-removing step, a catheter tube-inserting step, and a urine-voiding step. The catheter assembly-obtaining step includes obtaining the intermittent-catheter assembly in a packaged state of the intermittent-catheter assembly. The intermittent-catheter assembly has an intermittent catheter disposed in a catheter housing in the packaged state of the intermittent-catheter assembly. The intermittent catheter-exposing step includes exposing the intermittent catheter for removal from the catheter housing, which includes an outer sleeve-grasping step, a force-applying step, and an outer sleeve-sliding step. The outer sleeve-grasping step includes grasping an outer sleeve of the catheter housing. The force-applying step includes applying a force to an exposed end of an inner sleeve of the catheter housing. The outer sleeve-sliding step includes sliding the outer sleeve toward the exposed end of the inner sleeve in opposition to the force applied to the exposed end of the inner sleeve. The intermittent catheter-removing step includes removing the intermittent catheter from the catheter housing. The catheter tube-inserting step includes inserting a catheter tube of the intermittent catheter into a urethra. The urine-voiding step includes voiding urine from a bladder.

In some embodiments, the method further includes a catheter tube-removing step and a catheter assembly-disposing step. The catheter tube-removing step includes removing the catheter tube from the urethra after the urine-voiding step. The catheter assembly-disposing step includes disposing of the intermittent catheter and the catheter housing. Optionally, the intermittent catheter and the catheter housing are disposed of in a reassembled state or partially reassembled state of the intermittent-catheter assembly during the catheter assembly-disposing step.

Also disclosed herein is a method of an intermittent-catheter assembly including, in some embodiments, a catheter assembly-obtaining step, an intermittent catheter-exposing step, a catheter tube-inserting step, and a urine-voiding step. The catheter assembly-obtaining step includes obtaining the intermittent-catheter assembly in a packaged state of the intermittent-catheter assembly. The intermittent-catheter assembly has an intermittent catheter disposed in a catheter housing in the packaged state of the intermittent-catheter assembly. The intermittent catheter-exposing step includes exposing the intermittent catheter for insertion into a urethra, which includes a pull tab-removing step, an end piece-grasping step, and an end piece-sliding step. The pull tab-removing step includes removing a pull tab sealing a distal opening of an end piece of the catheter housing. The end piece-grasping step includes grasping the end piece. The end piece-sliding step includes proximally sliding the end piece over the catheter tube toward a funnel of the intermittent catheter. The catheter tube-inserting step includes inserting the catheter tube of the intermittent catheter into the urethra. The urine-voiding step includes voiding urine from a bladder.

In some embodiments, the method further includes a catheter tube-removing step and a catheter assembly-disposing step. The catheter tube-removing step includes removing the catheter tube from the urethra after the urine-voiding step. The catheter assembly-disposing step includes disposing of the intermittent catheter and the catheter housing. Optionally, the intermittent catheter and the catheter housing are disposed of in a reassembled state or partially reassembled state of the intermittent-catheter assembly during the catheter assembly-disposing step.

These and other features of the concepts provided herein will become more apparent to those of skill in the art in view of the accompanying drawings and following description, which describe particular embodiments of such concepts in greater detail.

DRAWINGS

7
8

Figure 14:
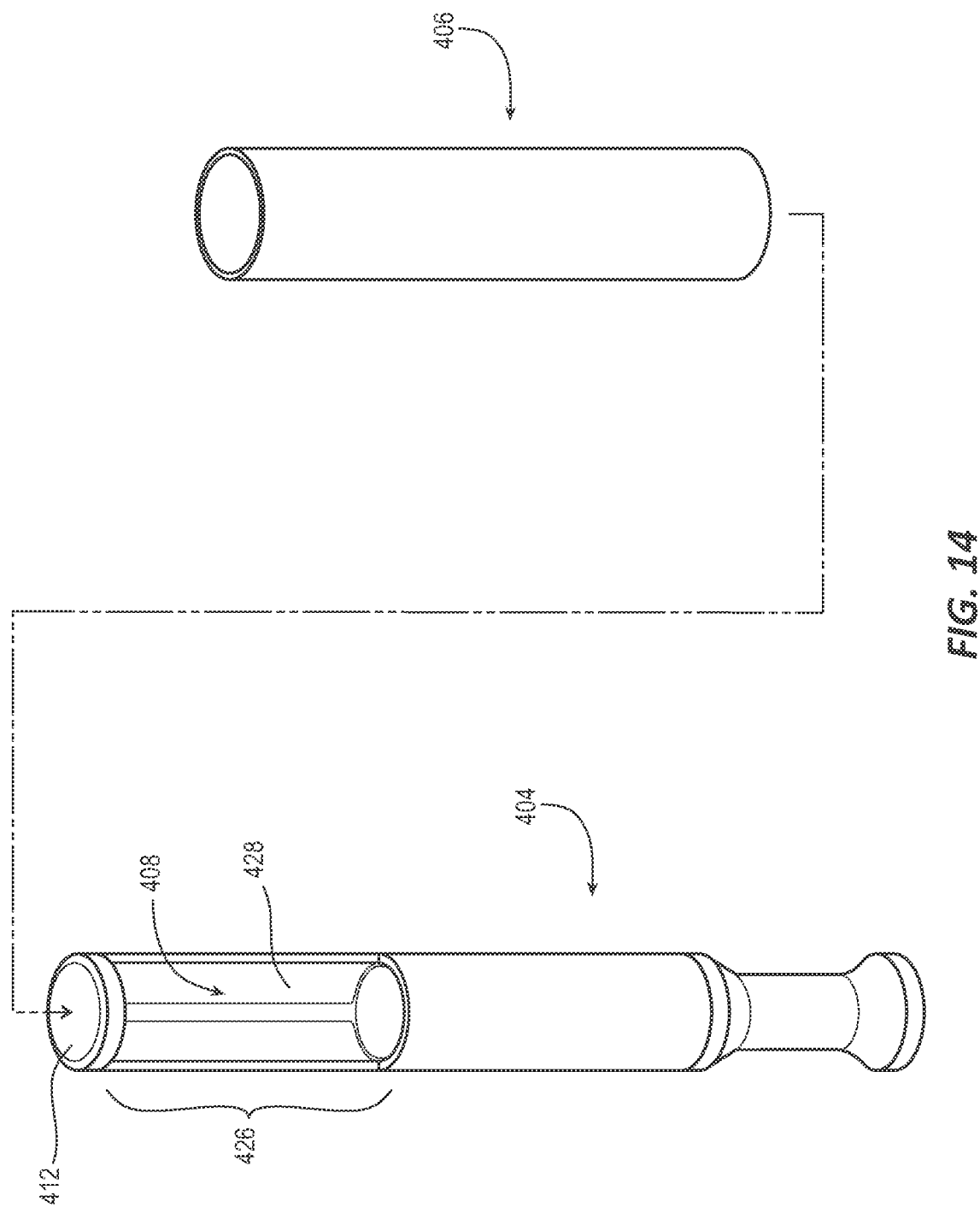

FIG. 14 illustrates the outer sleeve and the inner sleeve of the catheter housing separated from each other in accordance with some embodiments.

Figure 15C:
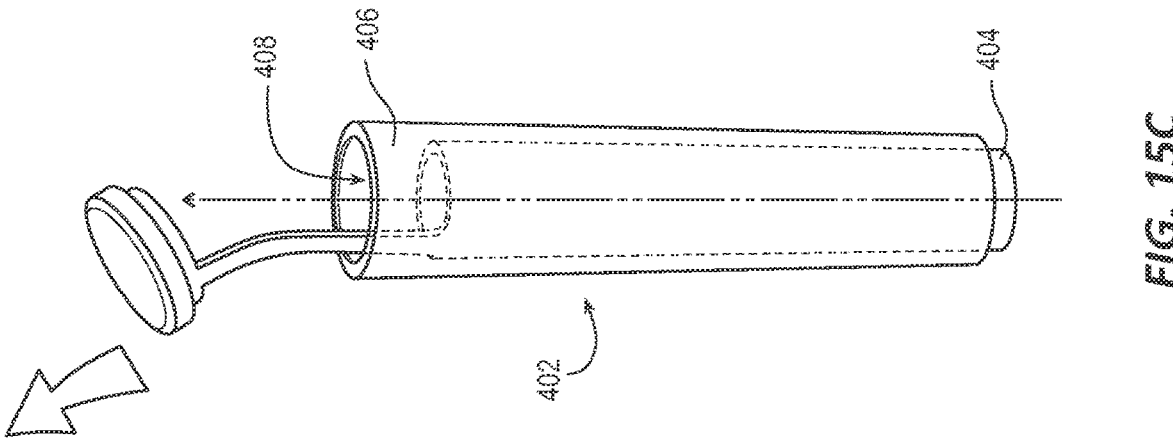
Figure 15B:
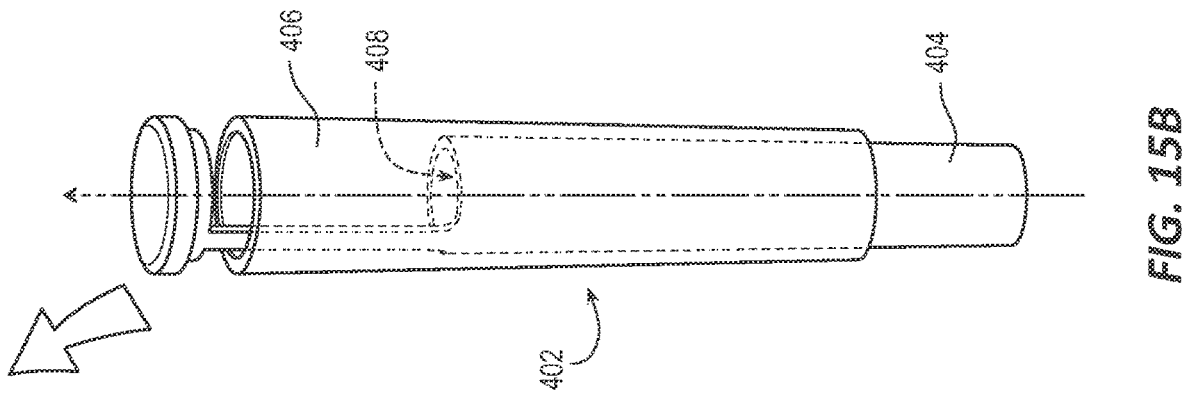
Figure 15A:
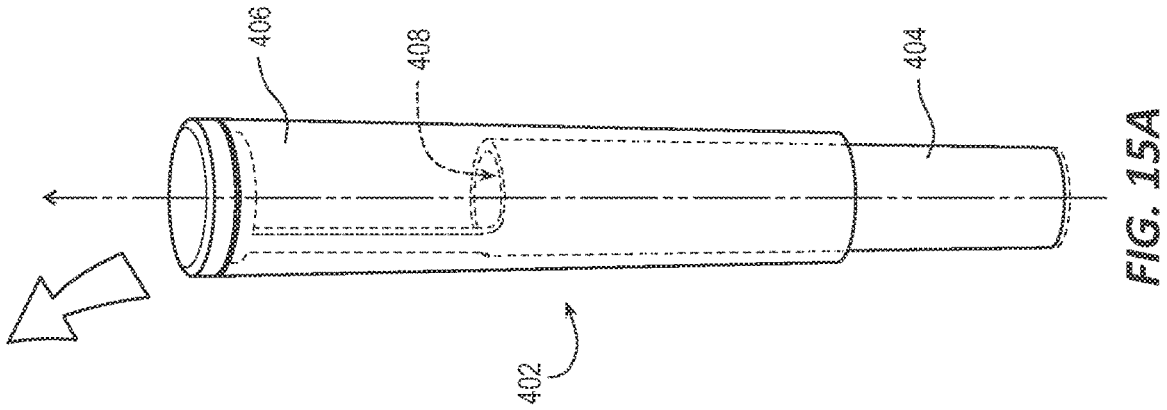

FIG. 15A illustrates a connecting portion of the inner sleeve disposed in the catheter housing in accordance with some embodiments.

FIG. 15B illustrates the connecting portion of the inner sleeve bending away from a centerline of the catheter housing in accordance with some embodiments.

FIG. 15C illustrates the connecting portion of the inner sleeve further bending away from the centerline of the catheter housing in accordance with some embodiments.

Figure 16C:
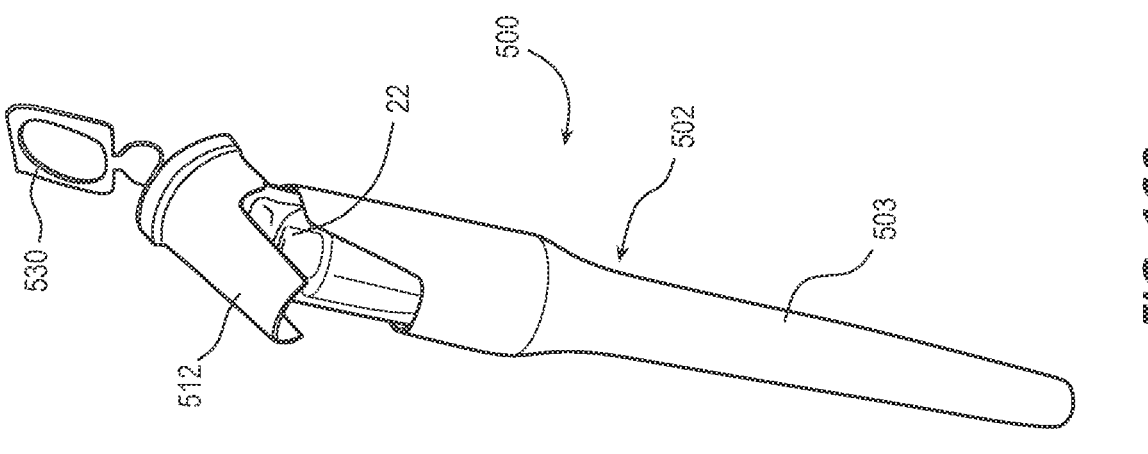
Figure 16B:
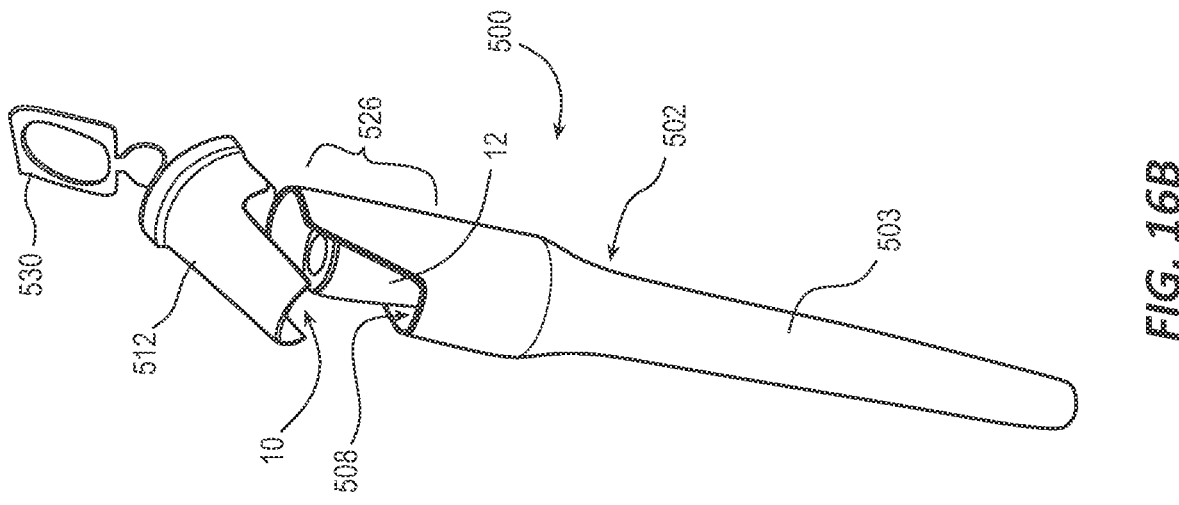
Figure 16A:
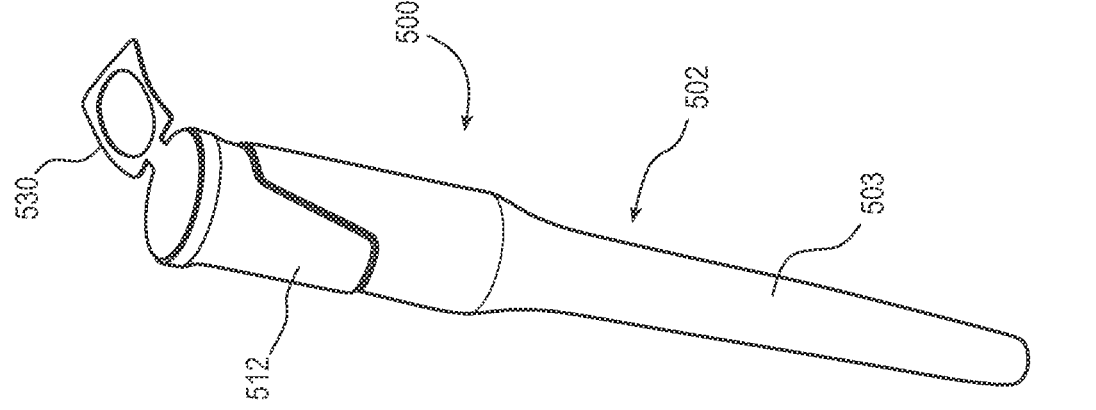

FIG. 16A illustrates a fifth intermittent-catheter assembly in a packaged state of the intermittent-catheter assembly in accordance with some embodiments.

FIG. 16B illustrates the fifth intermittent-catheter assembly with an intermittent catheter ready to be removed from a catheter housing in accordance with some embodiments.

FIG. 16C illustrates the fifth intermittent-catheter assembly with the intermittent catheter and a drainage bag ready to be removed from the catheter housing in accordance with some embodiments.

Figures 17, 18, 19:
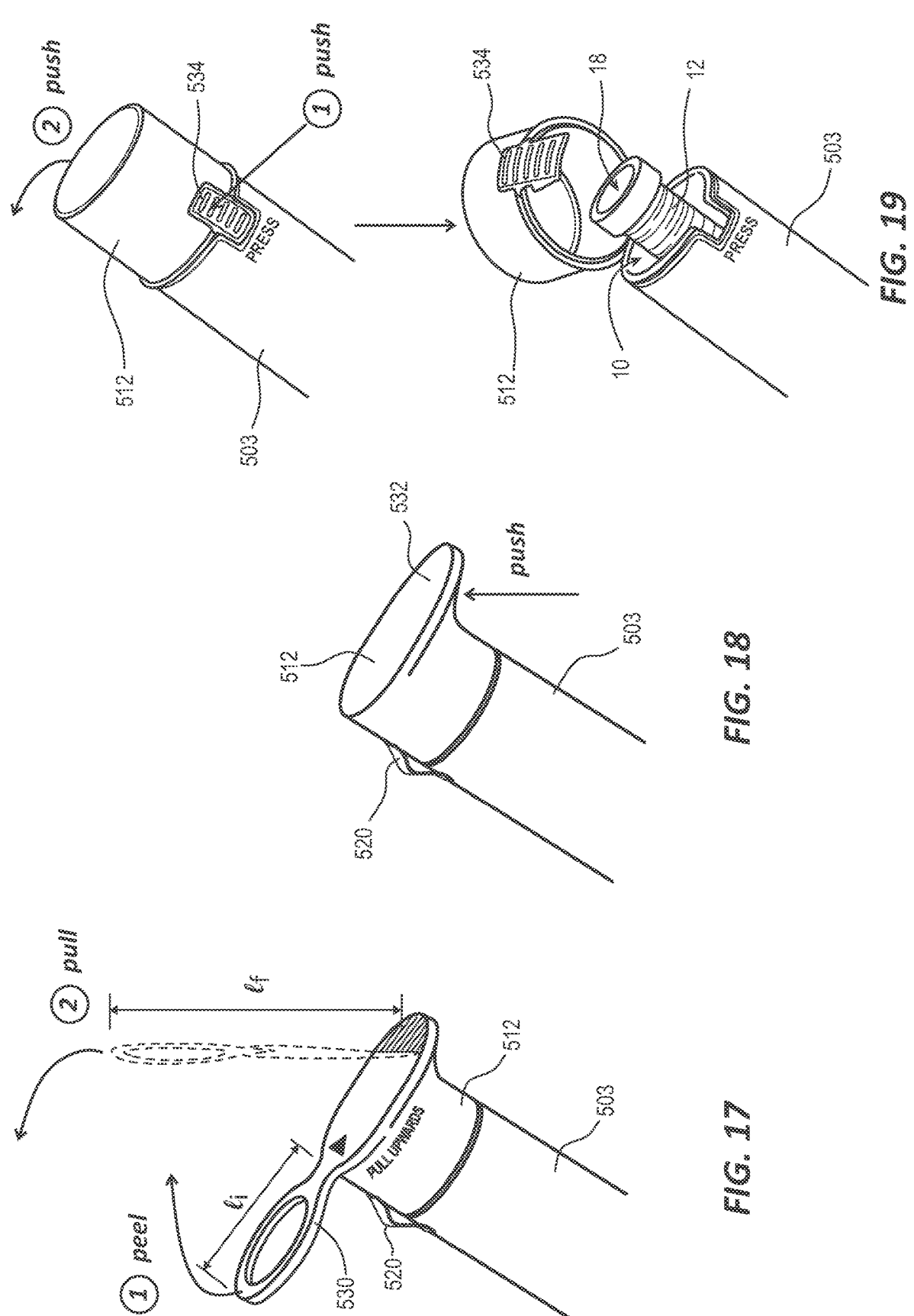

FIG. 17 illustrates a cap including a pull tab in accordance with some embodiments.

FIG. 18 illustrates a cap including a push tab in accordance with some embodiments.

FIG. 19 illustrates a cap including a push button in accordance with some embodiments.

Figures 20, 21:
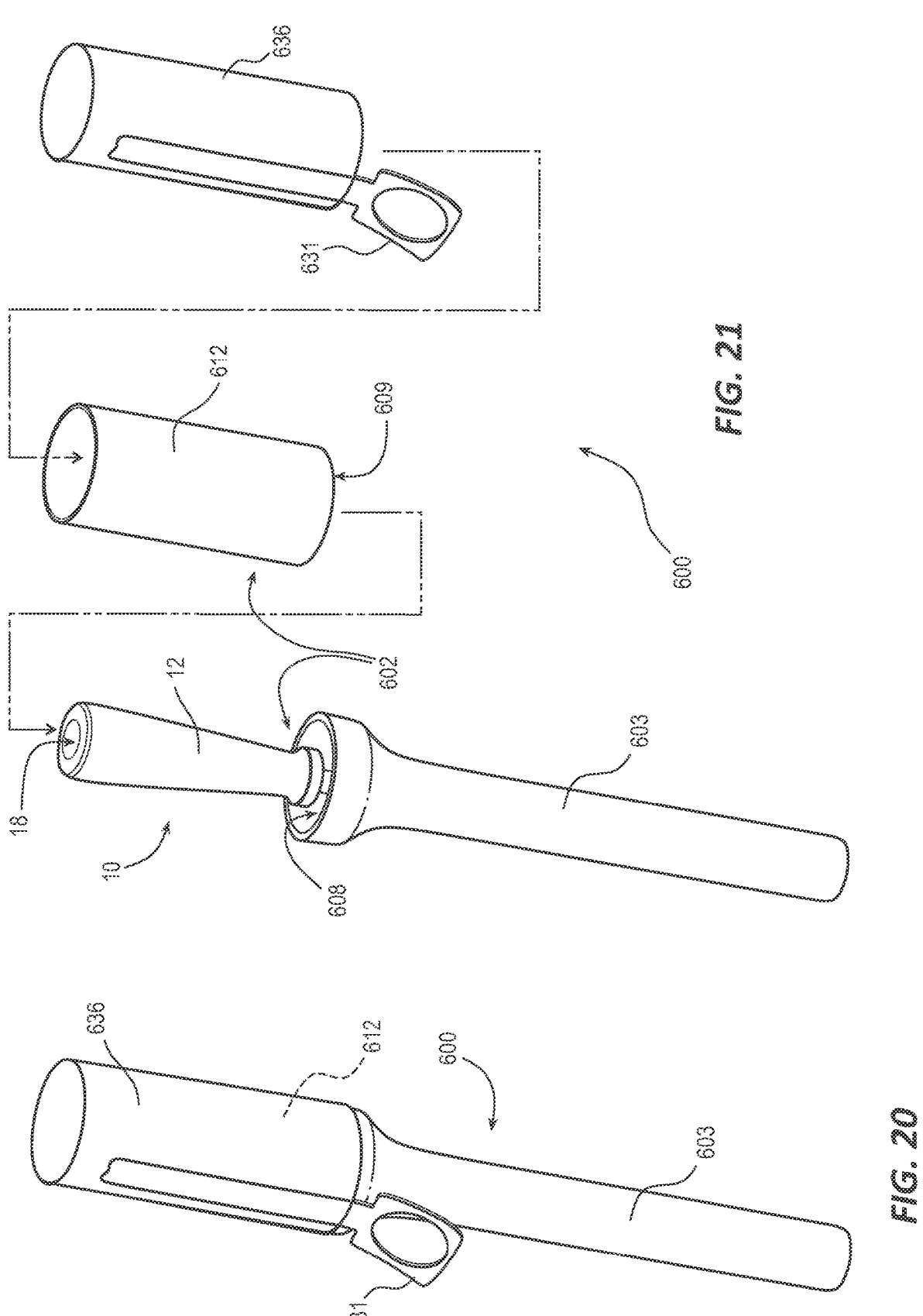

FIG. 20 illustrates a sixth intermittent-catheter assembly in a packaged state of the intermittent-catheter assembly in accordance with some embodiments.

FIG. 21 illustrates a sleeve, a cap, and shrink-wrap packaging of the intermittent-catheter assembly of FIG. 20 separated from each other in accordance with some embodiments.

Figures 22, 23:
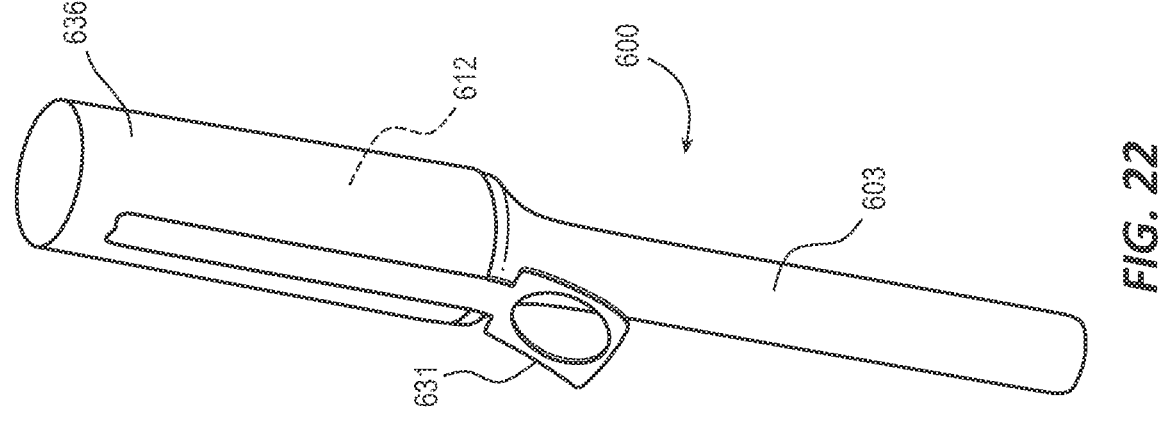

FIG. 22 illustrates the sixth intermittent-catheter assembly including a drainage bag in a packaged state of the intermittent-catheter assembly in accordance with some embodiments.

FIG. 23 illustrates a sleeve, a cap, and shrink-wrap packaging of the intermittent-catheter assembly of FIG. 22 separated from each other in accordance with some embodiments.

Figure 24:
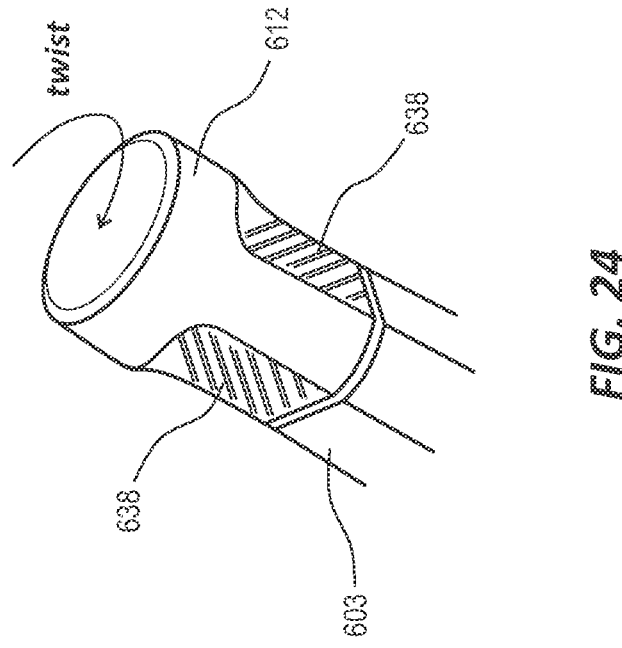

FIG. 24 illustrates a first cap including internal threads for screwing the cap off the sleeve in accordance with some embodiments.

Figure 25:
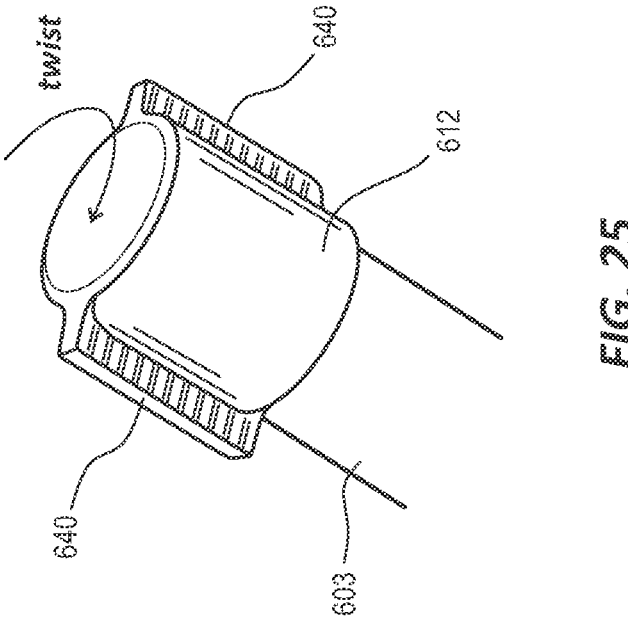

FIG. 25 illustrates a second cap including internal threads for screwing the cap off the sleeve in accordance with some embodiments.

Figure 26:
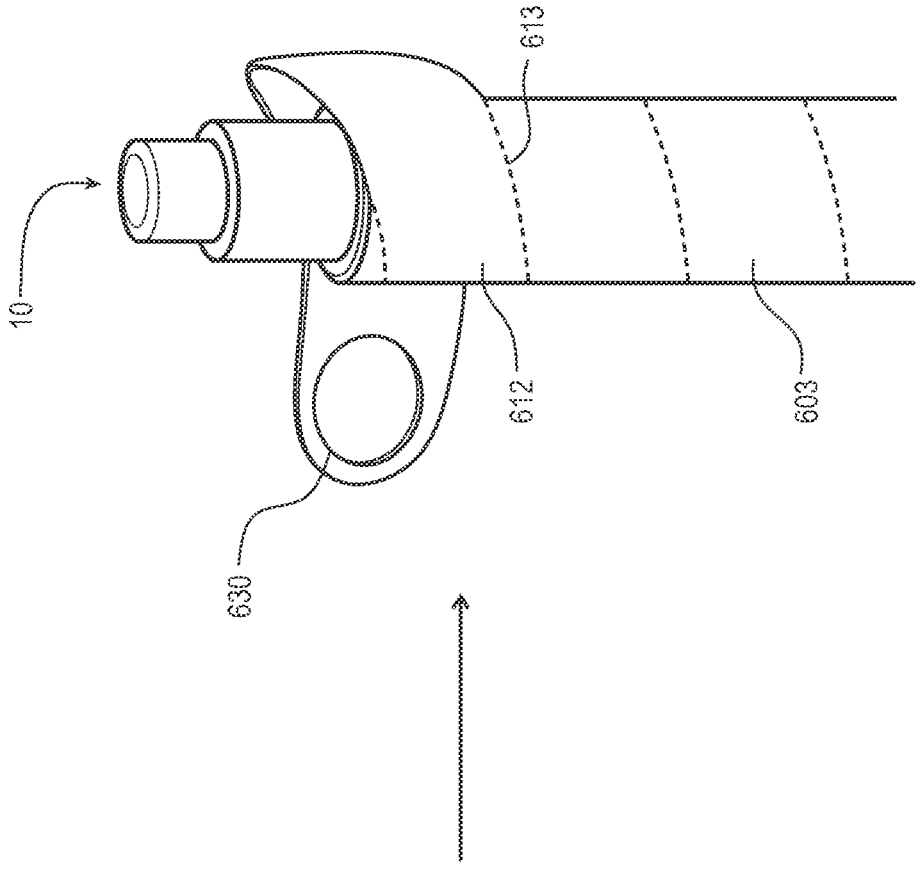
Figure 26:
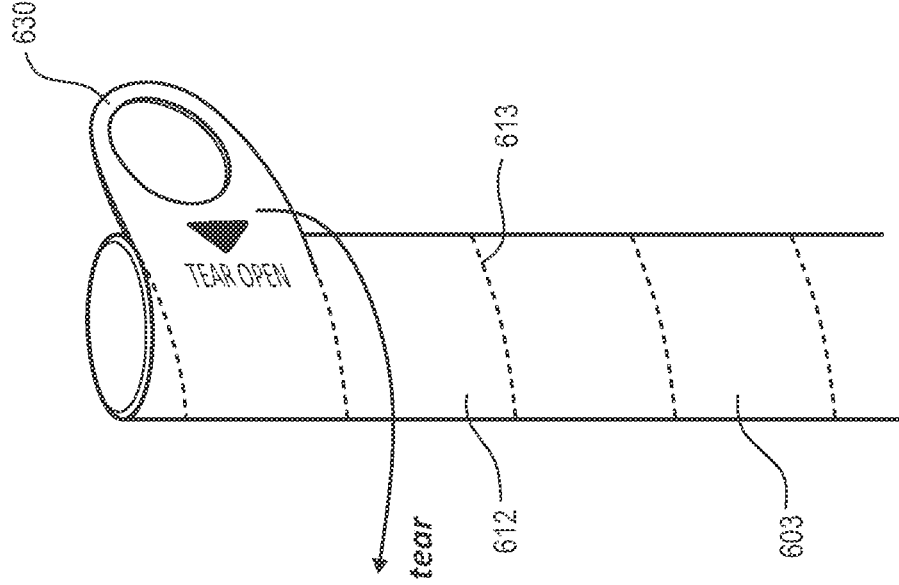

FIG. 26 illustrates a third cap configured for tearing the cap away from the sleeve in accordance with some embodiments.

Figure 27B:
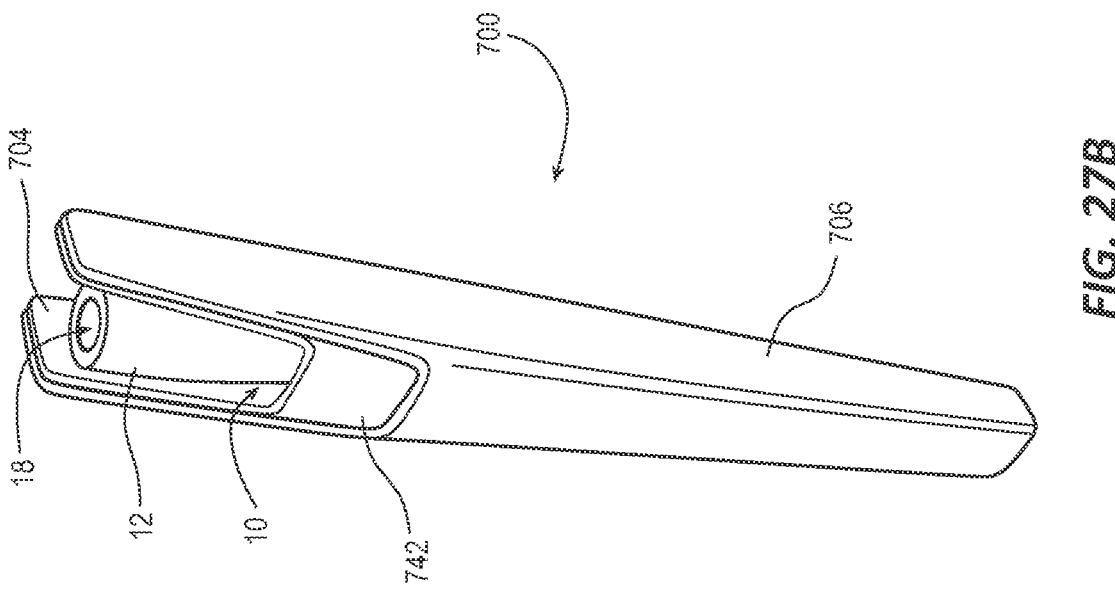
Figure 27A:
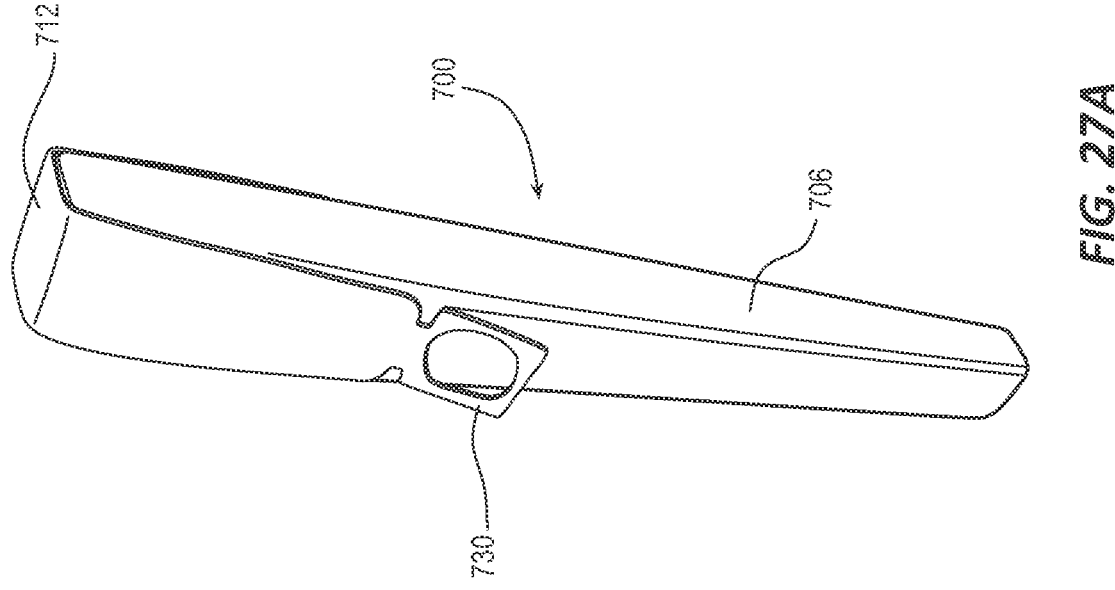

FIG. 27A illustrates a seventh intermittent-catheter assembly in a packaged state of the intermittent-catheter assembly in accordance with some embodiments.

FIG. 27B illustrates the seventh intermittent-catheter assembly with an intermittent catheter ready to be removed from a catheter housing in accordance with some embodiments.

Figure 28:
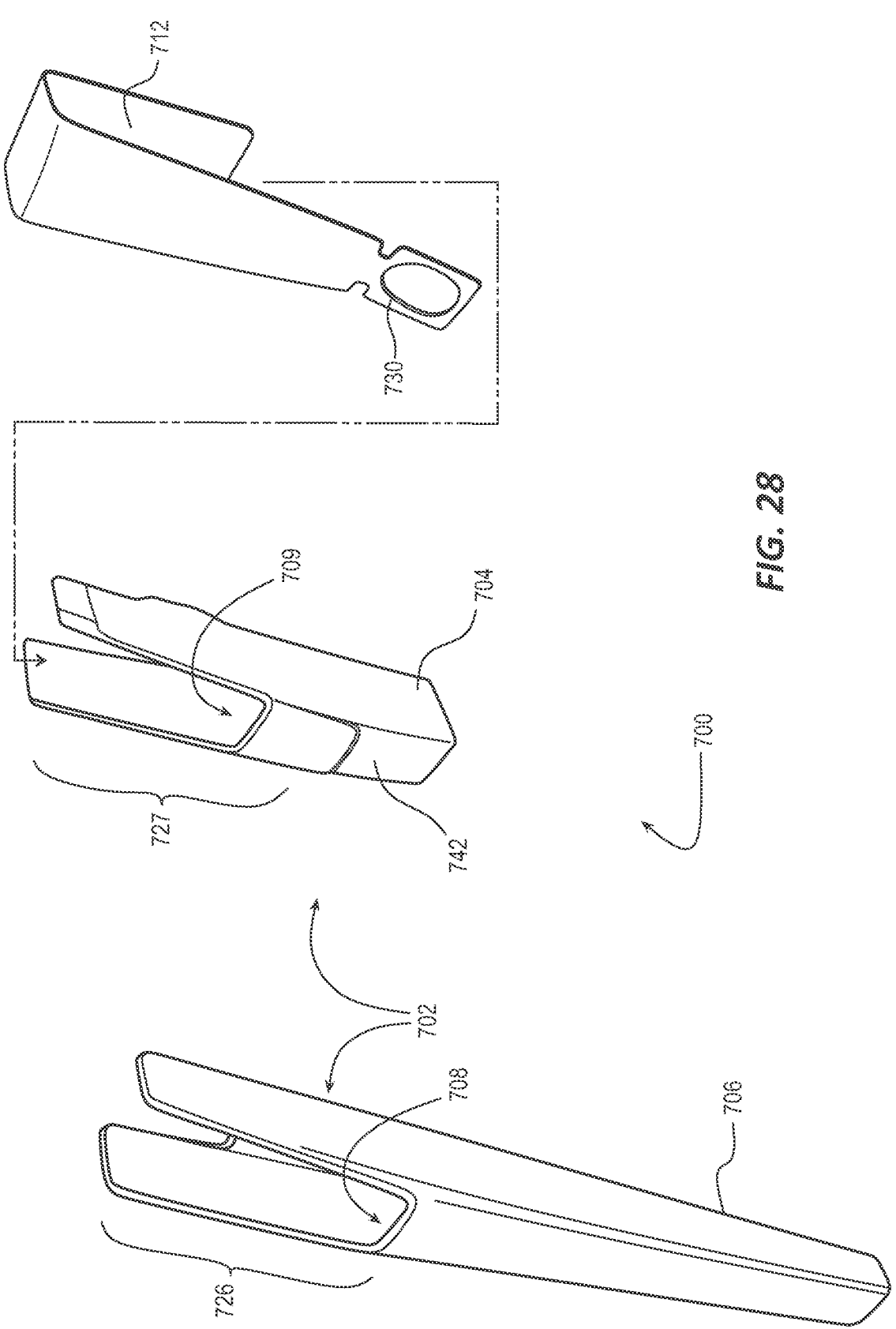

FIG. 28 illustrates a sleeve, a reinforcing insert, and an adhesive tab separated from each other in accordance with some embodiments.

Figure 29B:
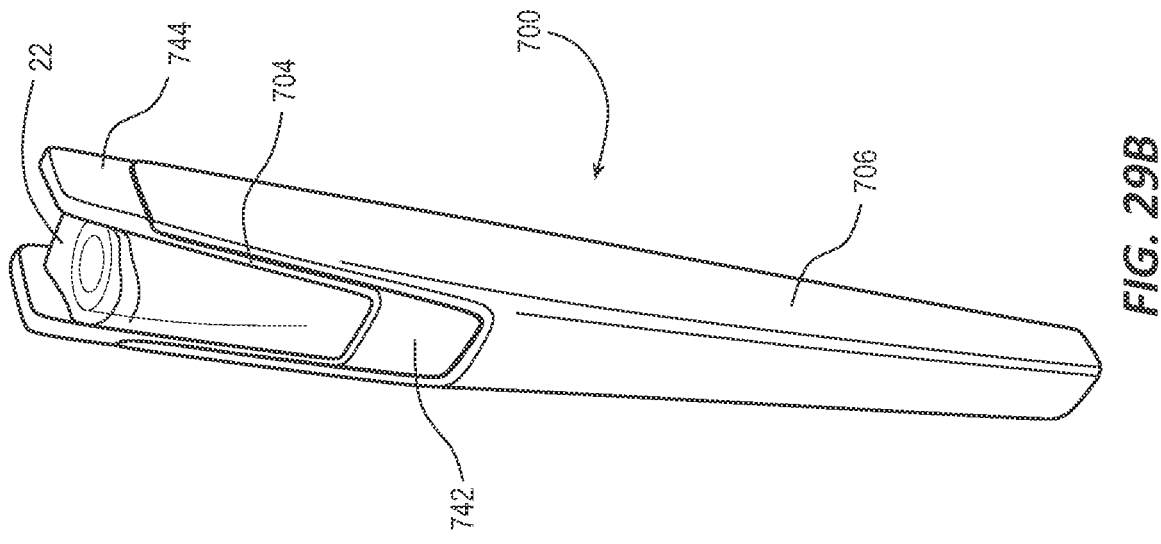
Figure 29A:
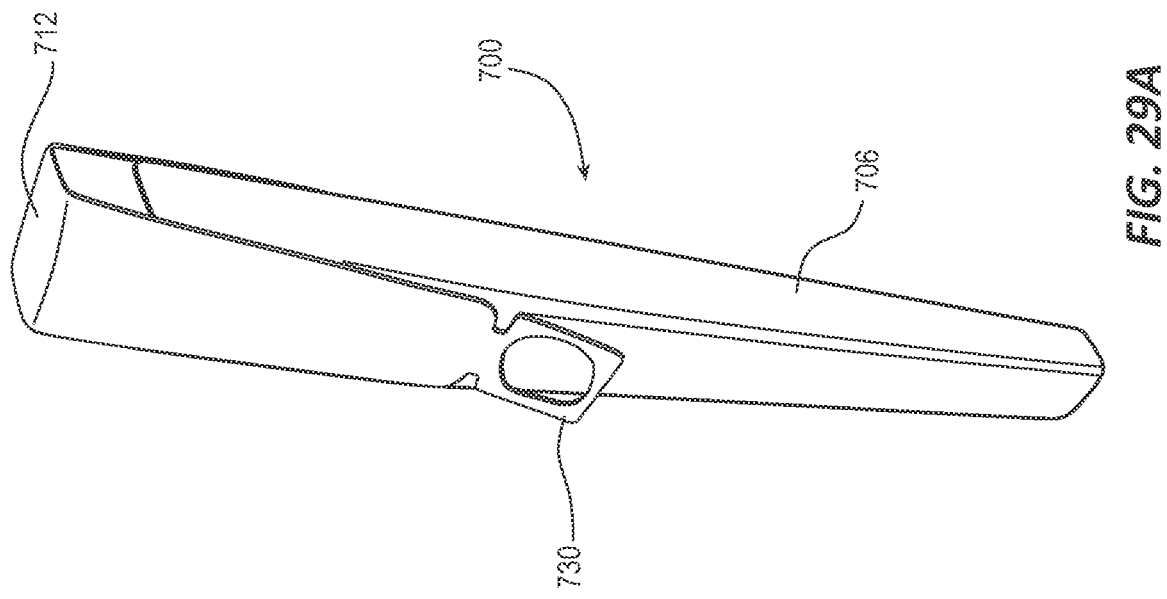

FIG. 29A illustrates a seventh intermittent-catheter assembly including a drainage bag in a packaged state of the intermittent-catheter assembly in accordance with some embodiments.

FIG. 29B illustrates the seventh intermittent-catheter assembly with the intermittent catheter and the drainage bag ready to be removed from a catheter housing in accordance with some embodiments.

Figure 30:
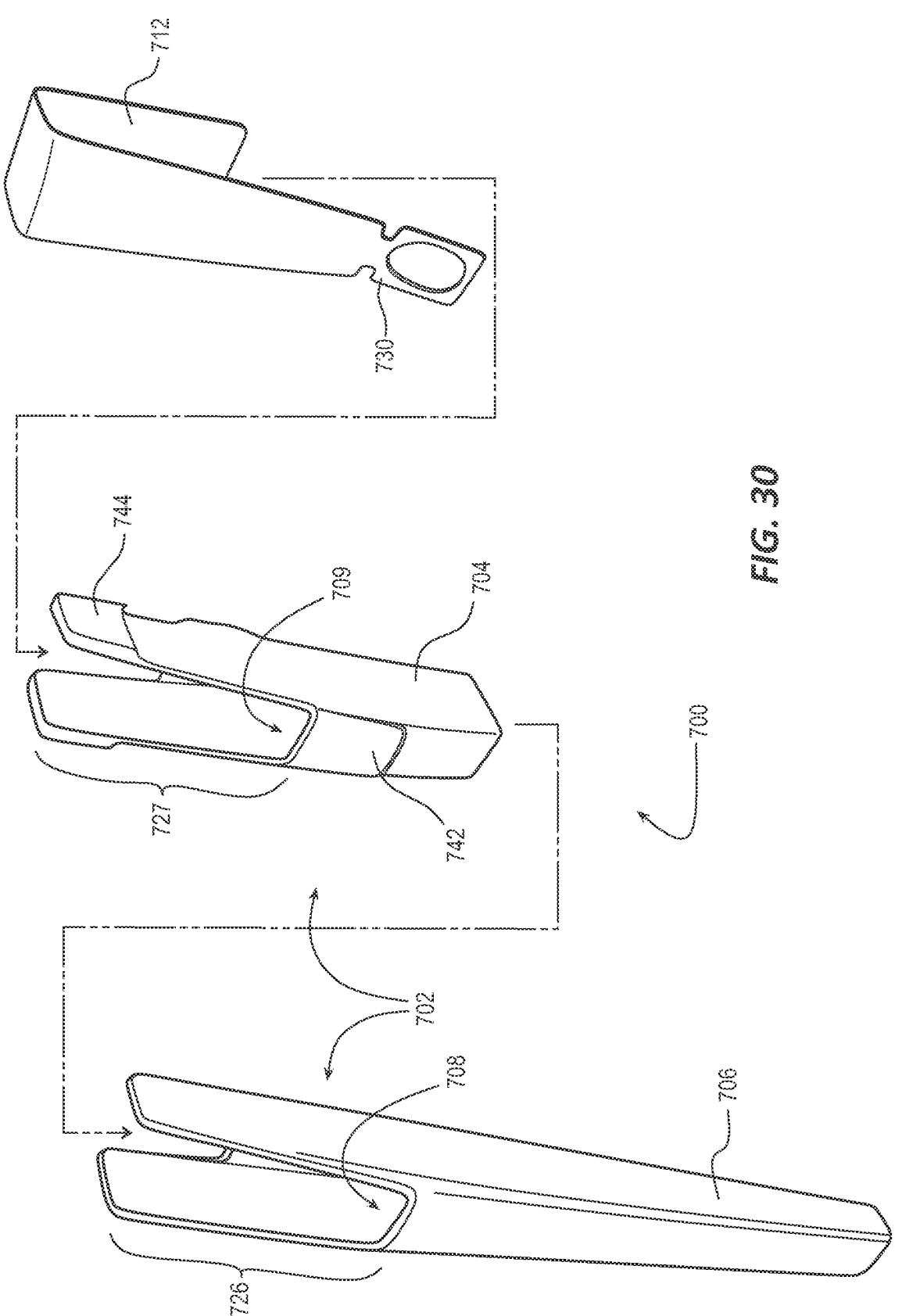

FIG. 30 illustrates the sleeve, the reinforcing insert, and the adhesive tab of the intermittent-catheter assembly of FIGS. 29A and 29B separated from each other in accordance with some embodiments.

Figure 31B:
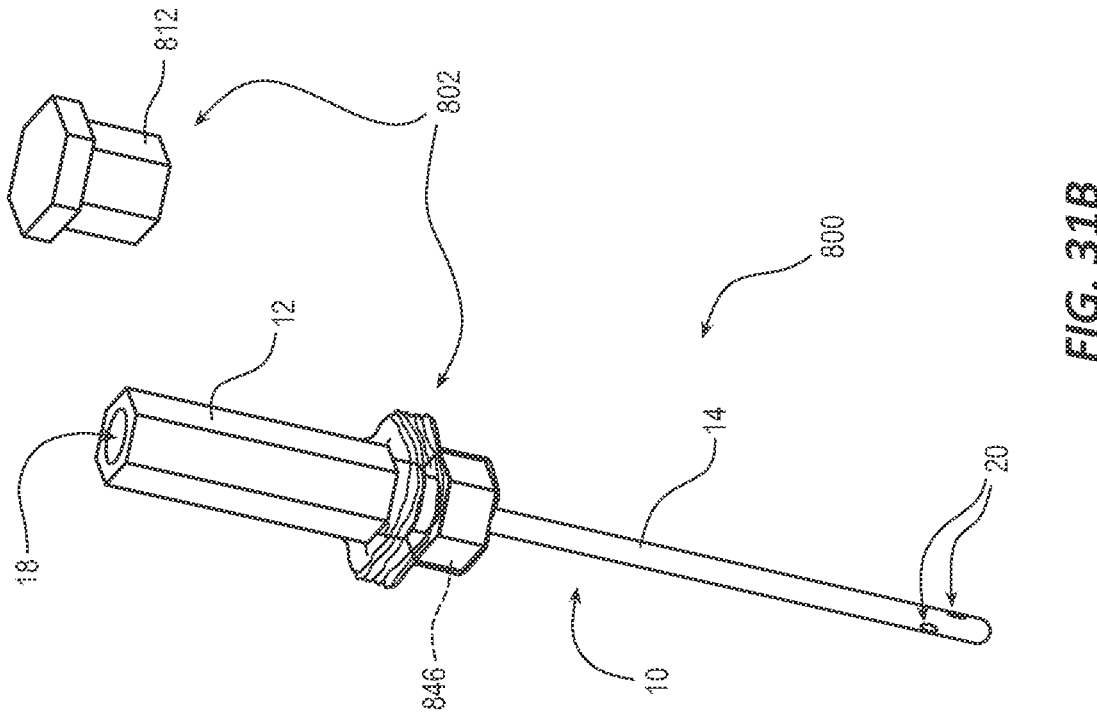
Figure 31A:
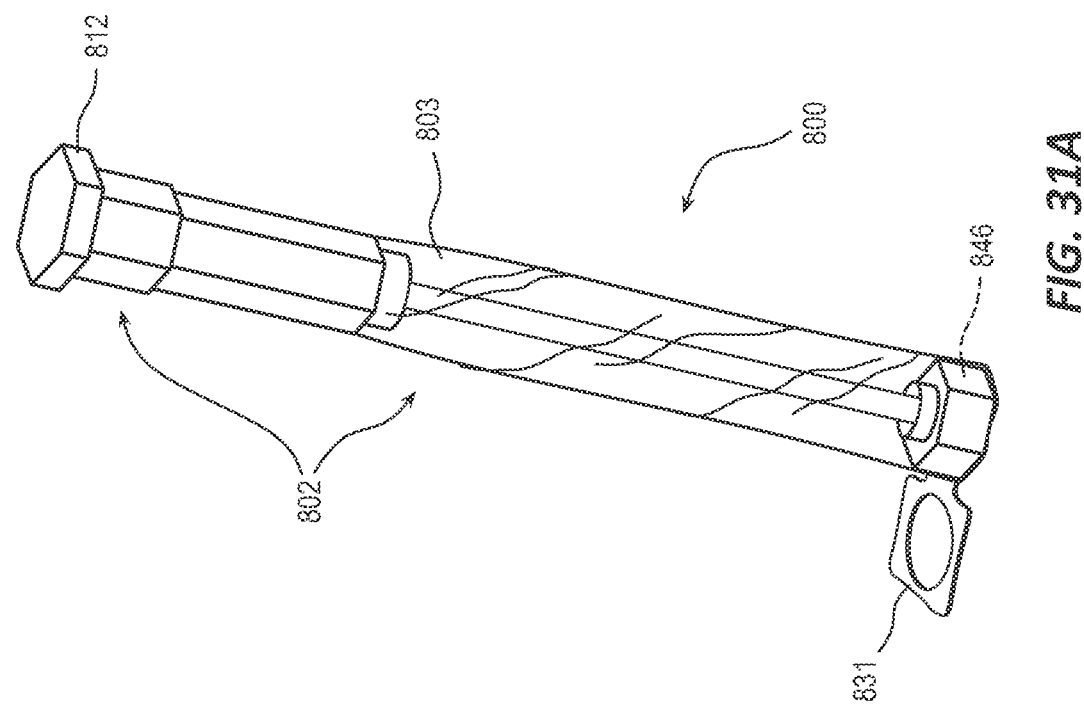

FIG. 31A illustrates an eighth intermittent-catheter assembly in a packaged state of the intermittent-catheter assembly in accordance with some embodiments.

FIG. 31B illustrates the eighth intermittent-catheter assembly with an intermittent catheter ready to be inserted into a urethra in accordance with some embodiments.

Figure 32B:
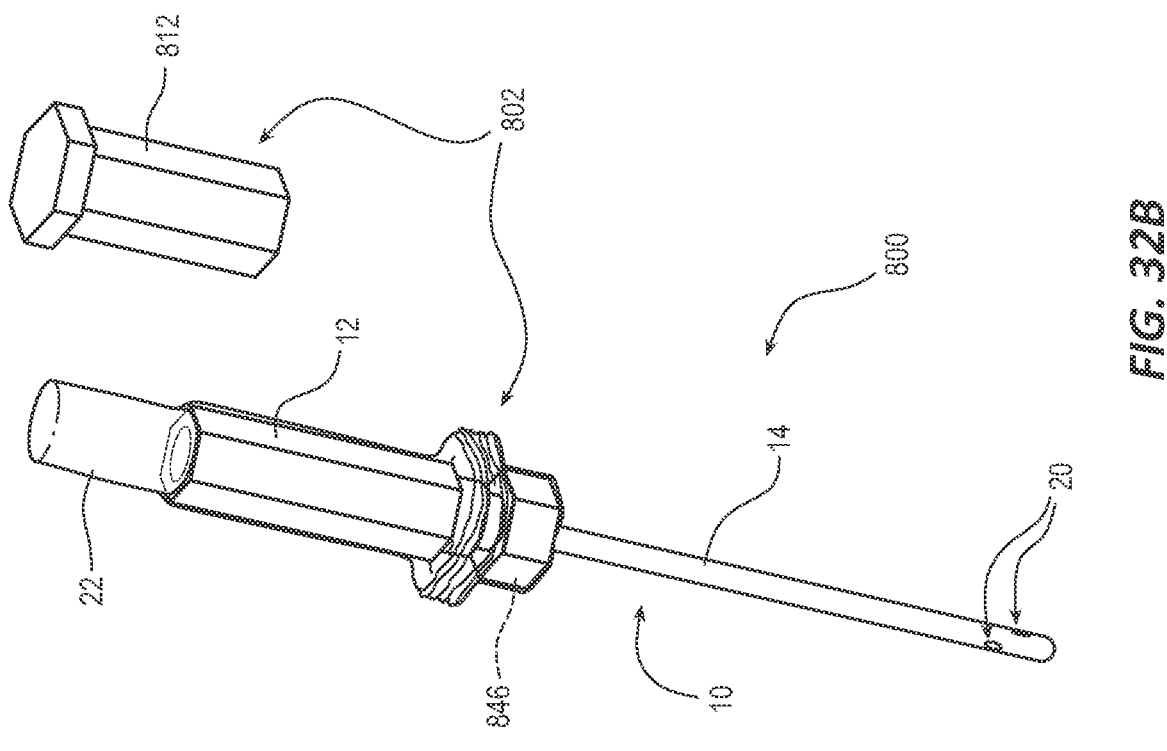
Figure 32A:
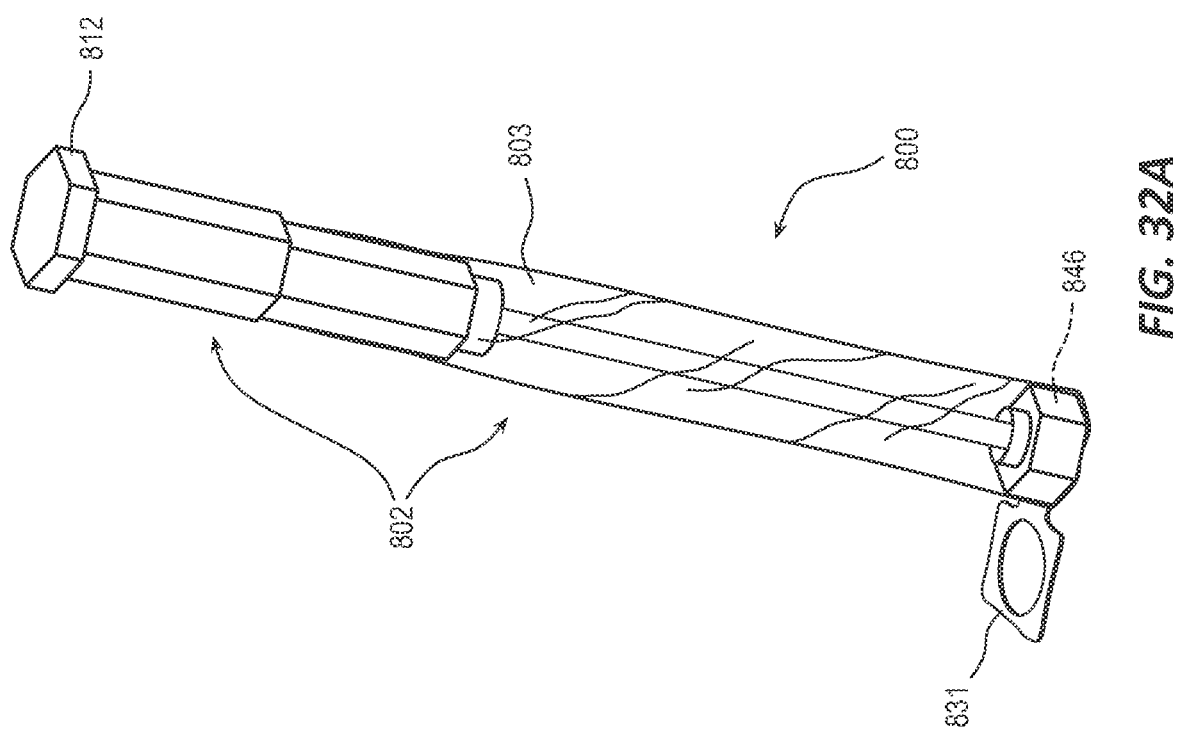

FIG. 32A illustrates the eighth intermittent-catheter assembly including a drainage bag in a packaged state of the intermittent-catheter assembly in accordance with some embodiments.

FIG. 32B illustrates the eighth intermittent-catheter assembly of FIG. 32A with the intermittent catheter ready to be inserted into a urethra in accordance with some embodiments.

Figure 33:
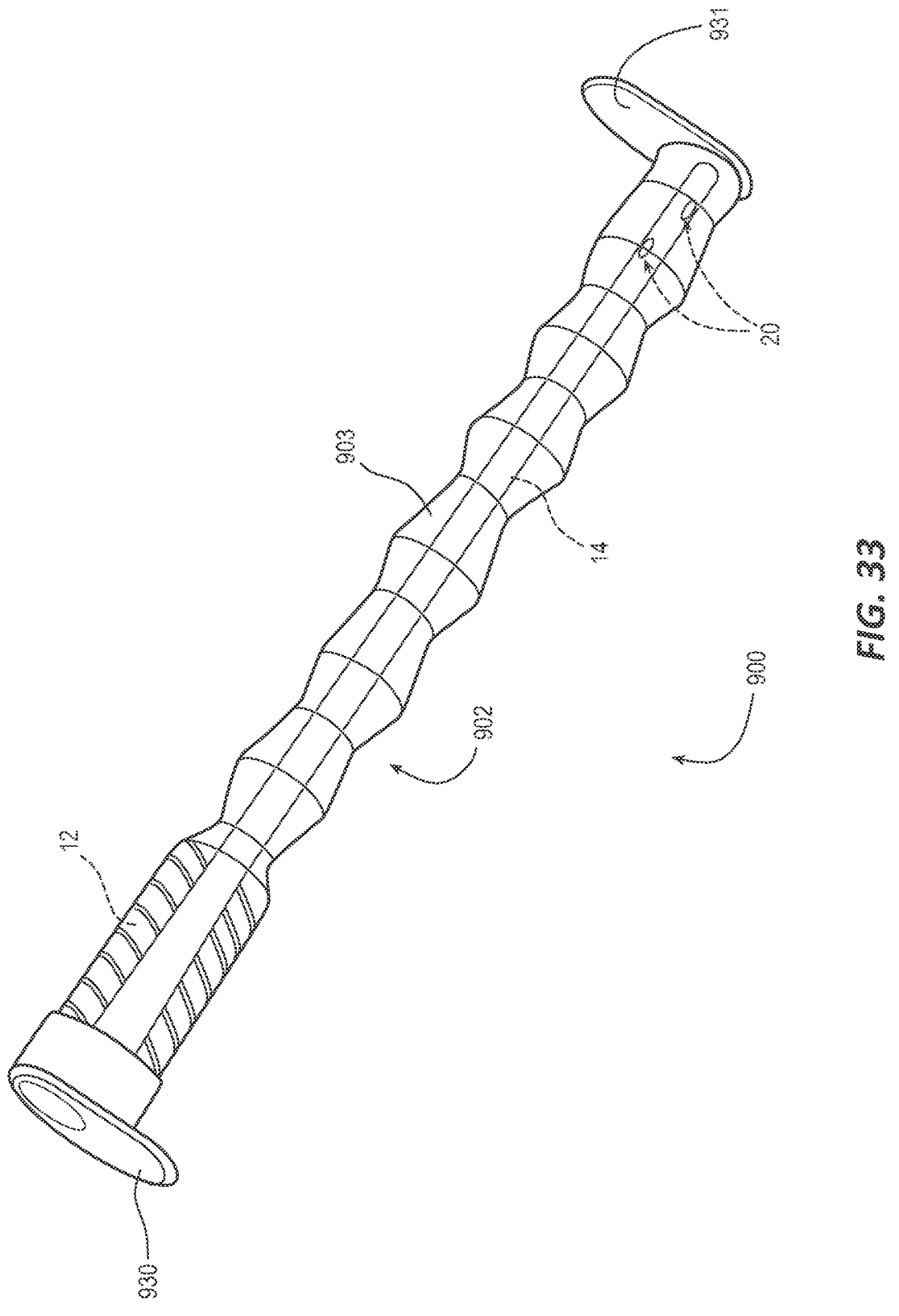

FIG. 33 illustrates a ninth intermittent-catheter assembly in a packaged state of the intermittent-catheter assembly in accordance with some embodiments.

Figure 34:
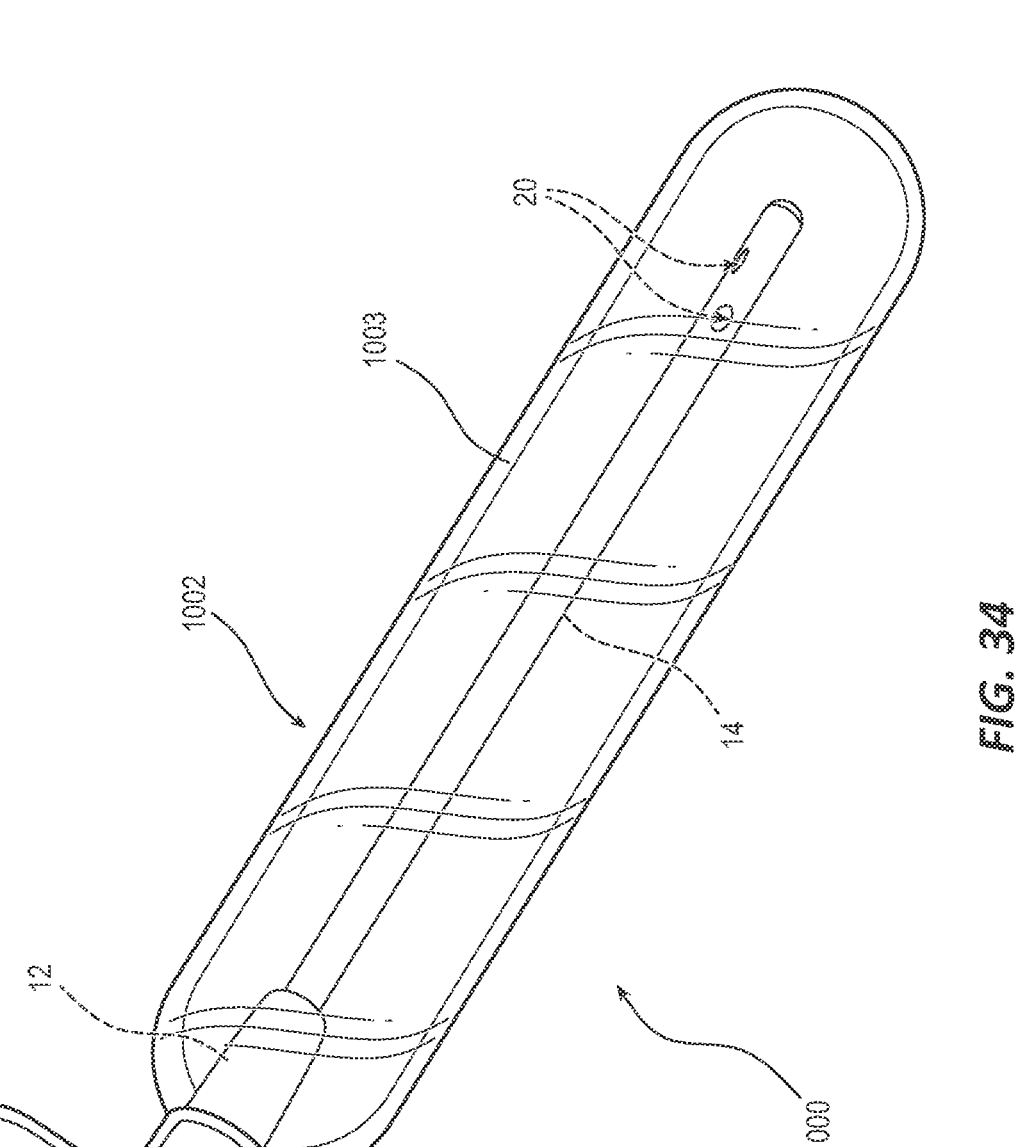

FIG. 34 illustrates a tenth intermittent-catheter assembly in a packaged state of the intermittent-catheter assembly in accordance with some embodiments.

Figure 35:
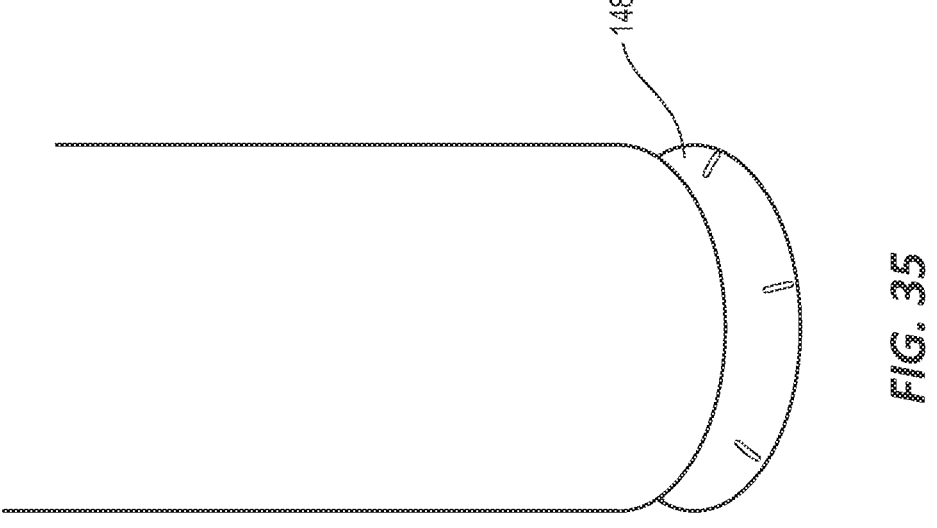

FIG. 35 illustrates a bottom suction cup for an intermittent-catheter assembly in accordance with some embodiments.

Figure 36:
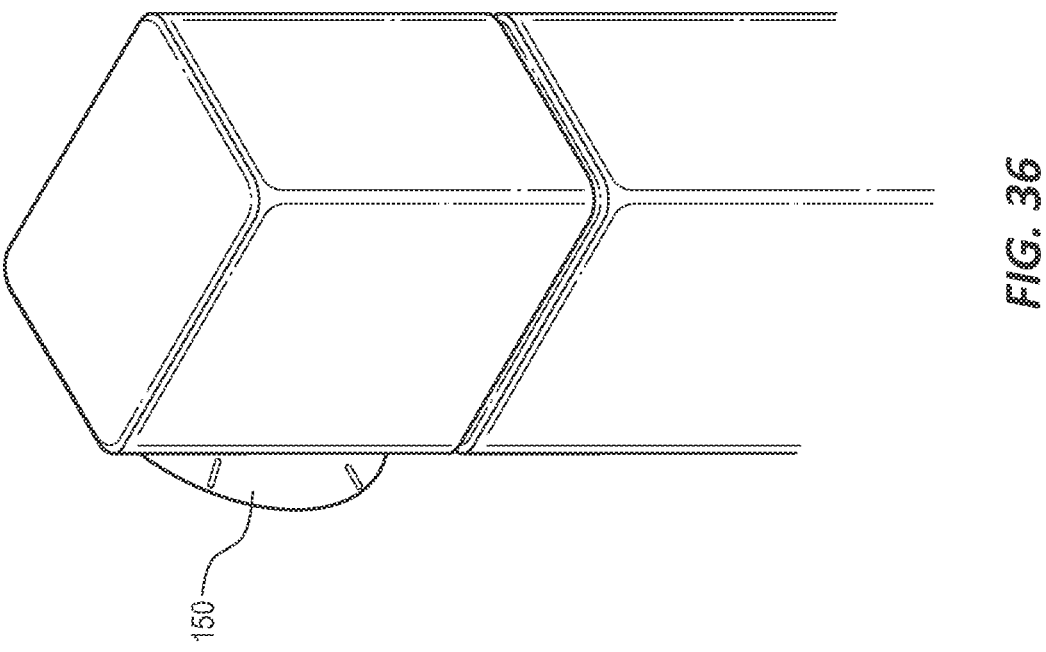

FIG. 36 illustrates a side suction cup for an intermittent-catheter assembly in accordance with some embodiments.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, users of urinary catheters such as intermittent catheters self-catheterize four to six times a day. As such, a simple-to-use intermittent catheter that ensures sterility before use and facilitates cleanliness after use is needed.

Disclosed herein are intermittent-catheter assemblies and methods thereof that address the foregoing.

The intermittent-catheter assemblies set forth below include an intermittent catheter and a catheter housing. The intermittent catheter can generally be used in any of the intermittent-catheter assemblies. As such, the intermittent catheter is described first followed by a number of different intermittent-catheter assemblies, which assemblies largely focus on the catheter housings thereof. Should the intermittent catheter need any modifications for use with a particular intermittent-catheter assembly, such modifications are described in relation to the particular intermittent-catheter assembly if useful for understanding the particular intermittent-catheter assembly. Methods of the intermittent-catheter assemblies are described after the intermittent-catheter assemblies.

Intermittent Catheters

As shown in any figure of a number of figures, an intermittent catheter 10 (e.g., a female intermittent catheter) includes a funnel 12 and a catheter tube 14 fluidly coupled to the funnel 12.

The funnel 12 is configured to provide a handle for holding the intermittent catheter 10 while removing the intermittent catheter 10 from a catheter housing or voiding urine through a proximal opening 18 of the funnel 12. The funnel 12 can include a neck 16 into which the catheter tube 14 is inserted. If the intermittent catheter 10 does not include the neck 16, the catheter tube 14 is inserted into a distal opening of the funnel 12. The funnel 12, the neck 16, or both the funnel 12 and the neck 16 can include a plurality of ridges integrated into an outer surface thereof. The ridges can be circumferential ridges configured for gripping the funnel 12 or the neck 16 as a handle while removing the intermittent catheter from the catheter housing or voiding the urine.

The catheter tube 14 is configured for insertion into a urethra for voiding urine from a bladder. The catheter tube 14 includes one or more eyelets 20 proximate a catheter tip. (See FIGS. 31B, 32B, 33, 34) The one-or-more eyelets 20 are in fluid communication with the proximal opening 18 of the funnel 12 by way of a catheter-tube lumen extending along a length of the catheter tube 14.

The intermittent catheter 10 can further include a lubricant disposed on the catheter tube 14 such as coating the catheter tube 14.

Intermittent Catheter Assemblies

Figure 5C:
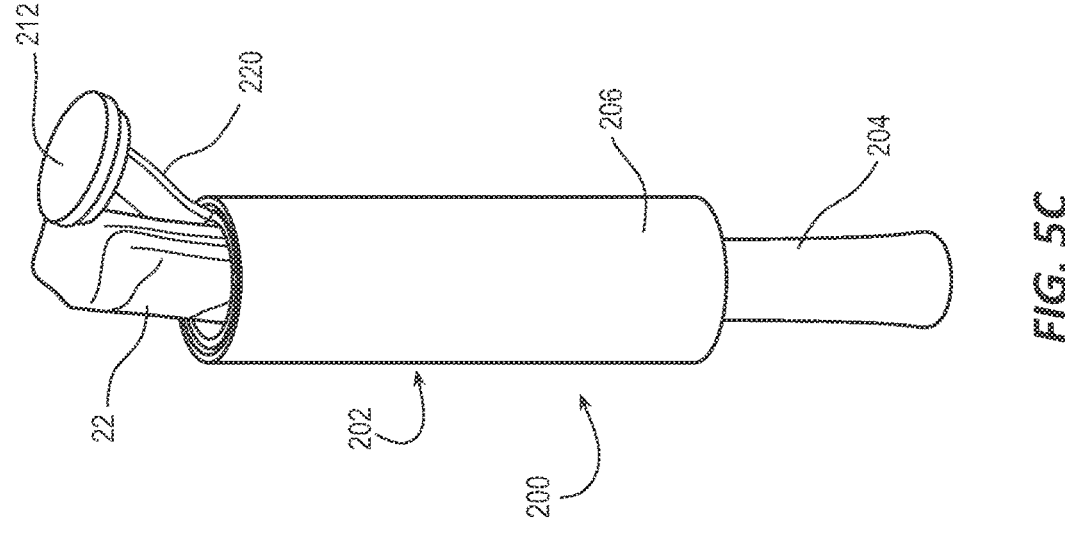
FIG. 5C illustrates the second intermittent-catheter assembly with the intermittent catheter and a drainage bag ready to be removed from the catheter housing in accordance with some embodiments.
Figure 5B:
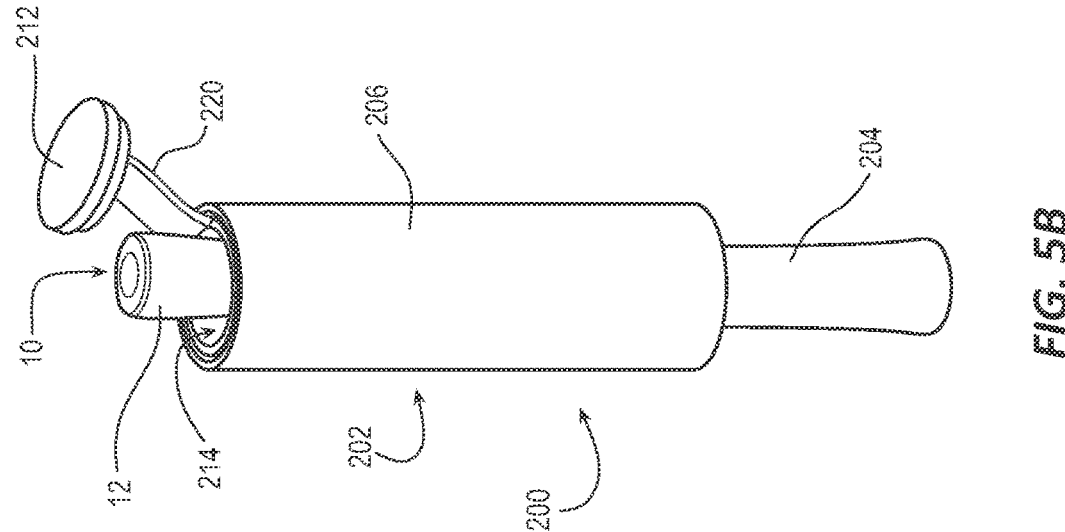
FIG. 5B illustrates the second intermittent-catheter assembly with an intermittent catheter ready to be removed from a catheter housing in accordance with some embodiments.
Figure 5A:
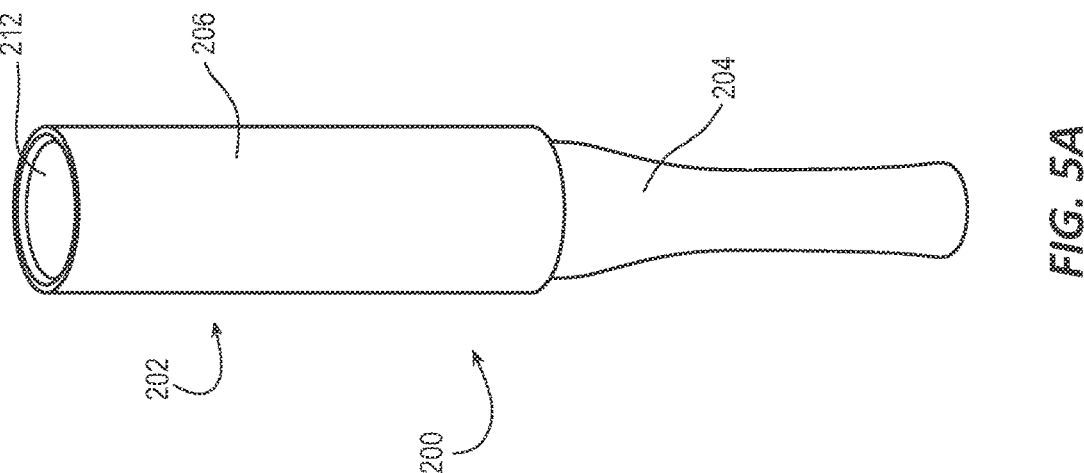
FIG. 5A illustrates a second intermittent-catheter assembly in a packaged state of the intermittent-catheter assembly in accordance with some embodiments.
Figures 7A, 7B, 8:
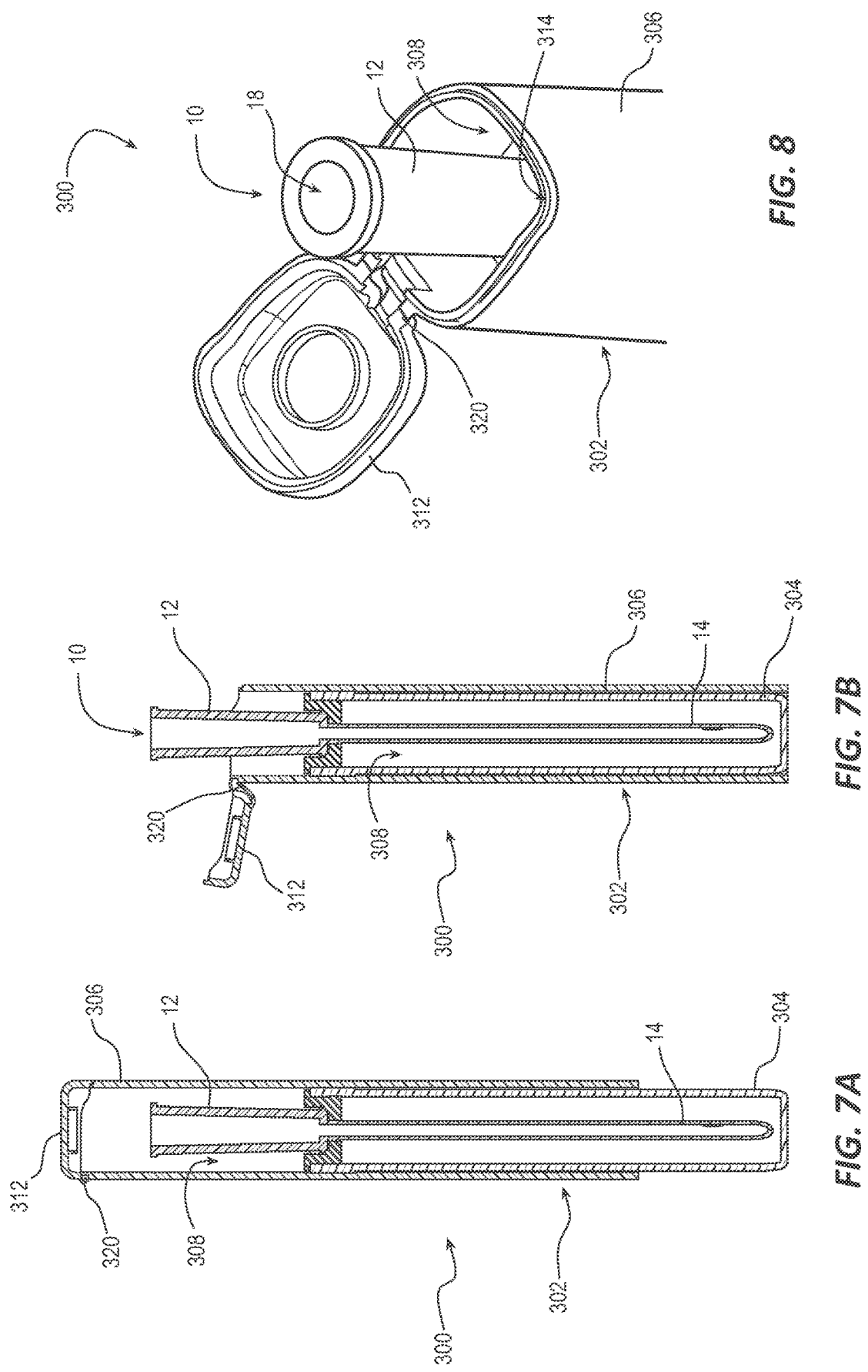
FIG. 7A illustrates a cross section of a third intermittent-catheter assembly in a packaged state of the intermittent-catheter assembly in accordance with some embodiments.
FIG. 7B illustrates a cross section of the third intermittent-catheter assembly with an intermittent catheter ready to be removed from a catheter housing in accordance with some embodiments.
FIG. 8 illustrates a detailed view of the third intermittent-catheter assembly with the intermittent catheter ready to be removed from the catheter housing in accordance with some embodiments.
Figures 9, 10, 11, 12:
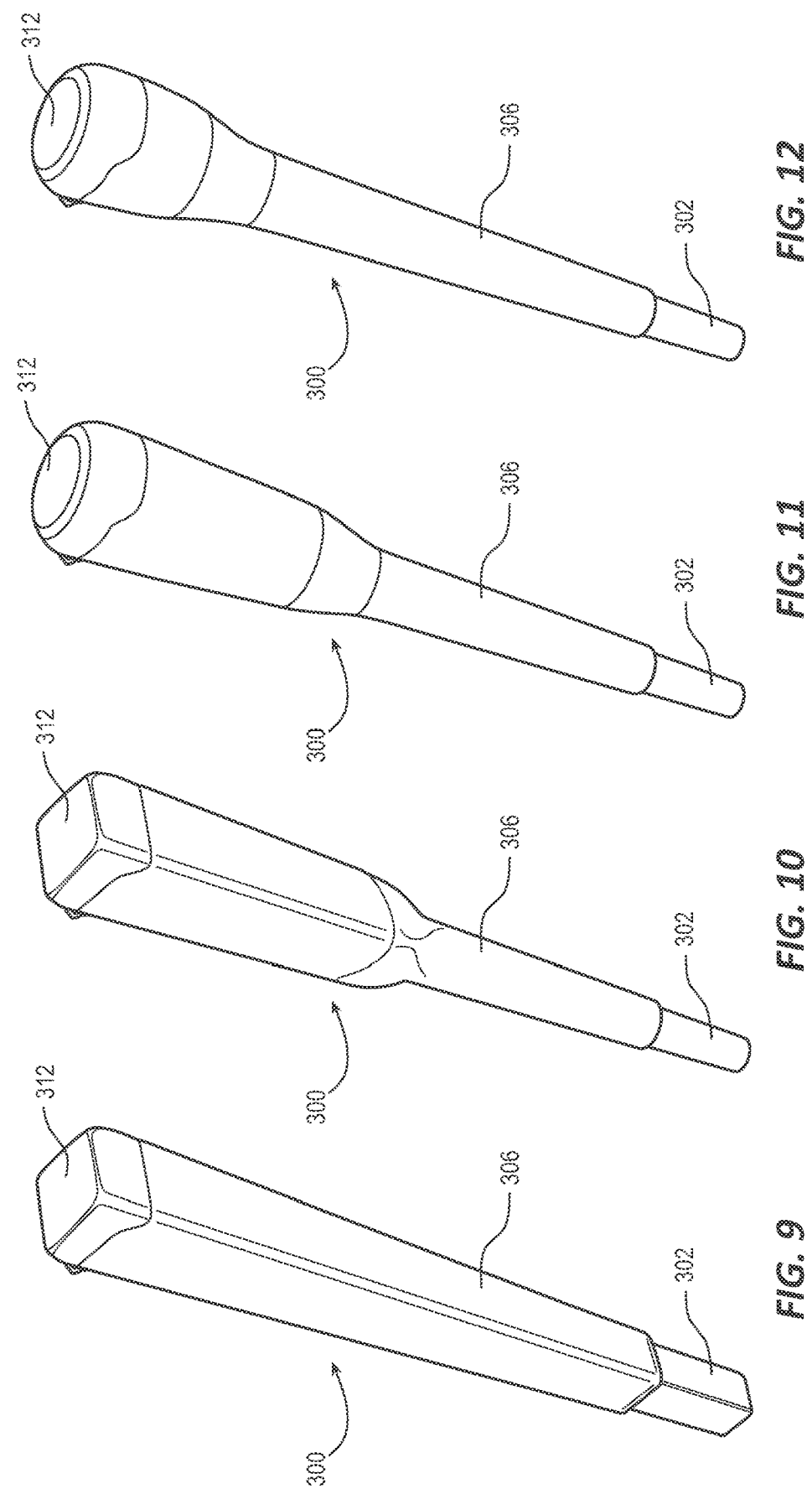
FIG. 9 illustrates the third intermittent-catheter assembly with a first form factor in accordance with some embodiments.
FIG. 10 illustrates the third intermittent-catheter assembly with a second form factor in accordance with some embodiments.
FIG. 11 illustrates the third intermittent-catheter assembly with a third form factor in accordance with some embodiments.
FIG. 12 illustrates the third intermittent-catheter assembly with a fourth form factor in accordance with some embodiments.
Figure 13C:
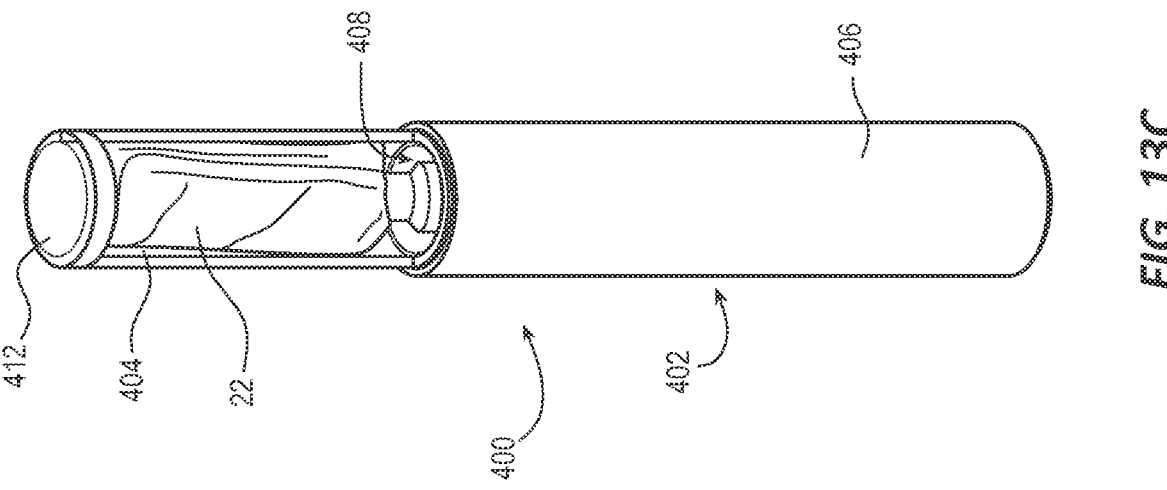
FIG. 13C illustrates the fourth intermittent-catheter assembly with an intermittent catheter and drainage bag ready to be removed from the catheter housing in accordance with some embodiments.
Figure 13B:
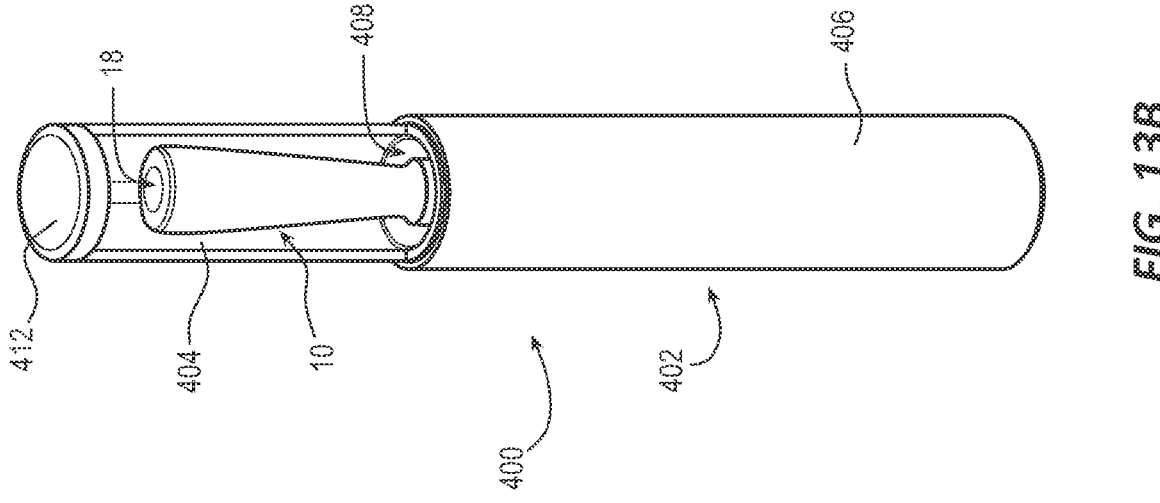
FIG. 13B illustrates the fourth intermittent-catheter assembly when an outer sleeve of a catheter housing is slid toward an exposed end of an inner sleeve of the catheter housing in accordance with some embodiments.
Figure 13A:
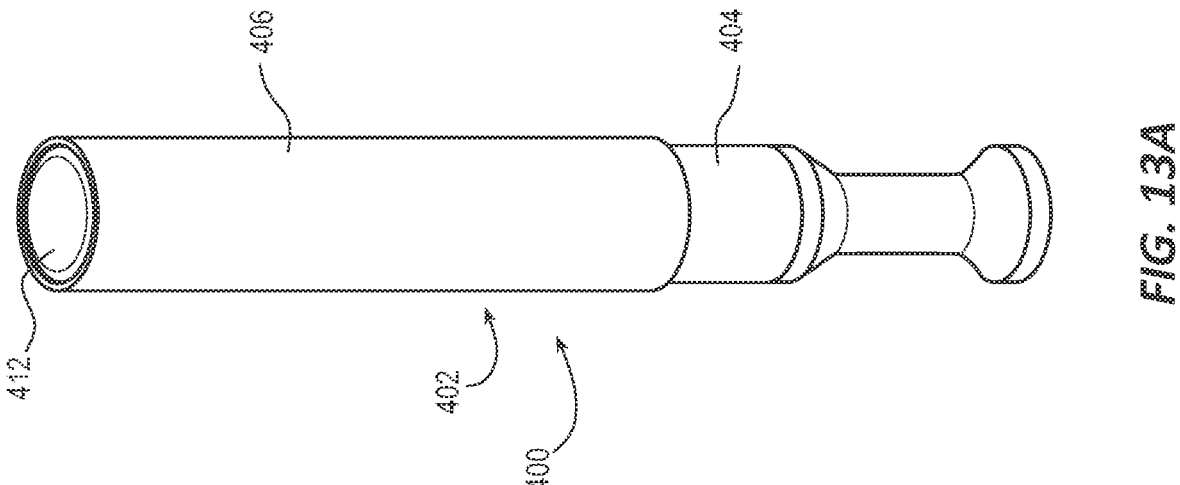
FIG. 13A illustrates a fourth intermittent-catheter assembly in a packaged state of the intermittent-catheter assembly in accordance with some embodiments.

FIGS. 1A-1C and 2A-2C illustrate different views of a first intermittent-catheter assembly 100 in different states in accordance with some embodiments. FIGS. 5A-5C illustrate a second intermittent-catheter assembly 200 in different states in accordance with some embodiments. FIGS. 7A, 7B, and 8 illustrate a third intermittent-catheter assembly 300 in different states in accordance with some embodiments. In consideration of the intermittent-catheter assembly 300 of FIGS. 7A, 7B, and 8 having a first form factor, FIGS. 9-12 illustrate second, third, fourth, and fifth form factors for the intermittent-catheter assembly 300 in accordance with some embodiments. FIGS. 13A-13C illustrate a fourth intermittent-catheter assembly 400 in different states in accordance with some embodiments.

As shown, the intermittent-catheter assembly 100, 200, 300, or 400 includes the intermittent catheter 10 and a catheter housing 102, 202, 302, or 402. The intermittent catheter 10 is disposed in the catheter housing 102, 202, 302, or 402 while in a packaged state of the intermittent-catheter assembly 100, 200, 300, or 400 for maintaining sterility of the intermittent catheter 10.

The catheter housing 102, 202, 302, or 402 includes an inner sleeve 104, 204, 304, or 404 and an outer sleeve 106, 206, 306, or 406. The inner sleeve 104, 204, 304, or 404 includes a longitudinal cavity 108, 208, 308, or 408 containing a majority of the intermittent catheter 10 in the packaged state of the intermittent-catheter assembly 100, 200, 300, or 400. The outer sleeve 106, 206, 306, or 406 is slidably disposed over the inner sleeve 104, 204, 304, or 404. The catheter housing 102, 202, 302, or 402 is configured to expose the intermittent catheter 10 for removal from the catheter housing 102, 202, 302, or 402 when the outer sleeve 106, 206, 306, or 406 is grasped and slid toward an exposed end of the inner sleeve 104, 204, 304, or 404 in opposition to a force (e.g., a normal force $F_n$) applied to the exposed end of the inner sleeve 104, 204, 304, or 404 such as by holding the exposed end of the inner sleeve 104, 204, 304, or 404 against a surface (e.g., a tabletop, a palm of a hand, etc.).

Figures 1A, 1B, 1C:
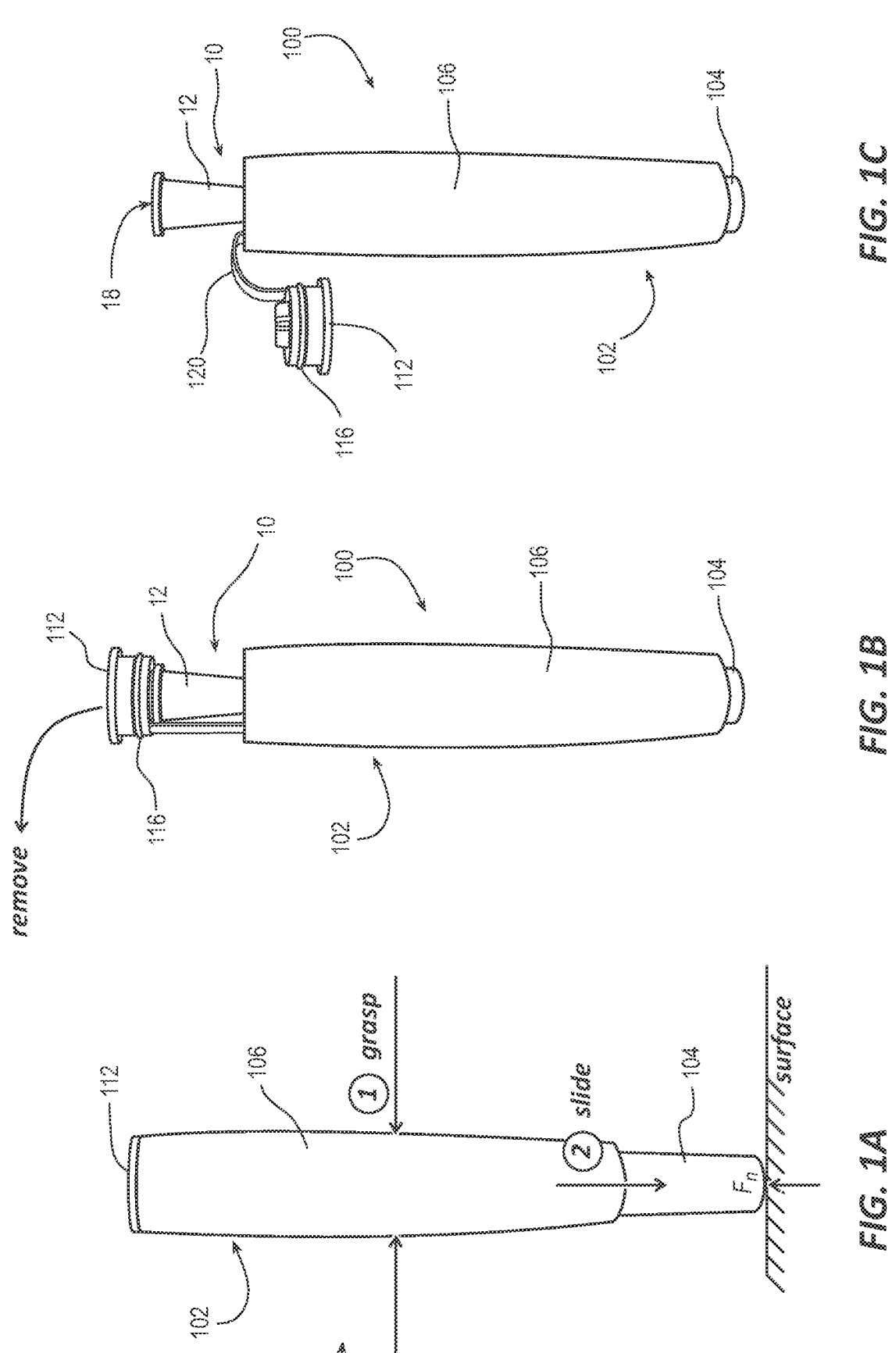
FIG. 1A illustrates a first intermittent-catheter assembly in a packaged state of the intermittent-catheter assembly in accordance with some embodiments.
FIG. 1B illustrates the first intermittent-catheter assembly when an outer sleeve of a catheter housing is slid toward an exposed end of an inner sleeve of the catheter housing in accordance with some embodiments.
FIG. 1C illustrates the first intermittent-catheter assembly with an intermittent catheter ready to be removed from the catheter housing in accordance with some embodiments.
Figures 2A, 2B, 2C:
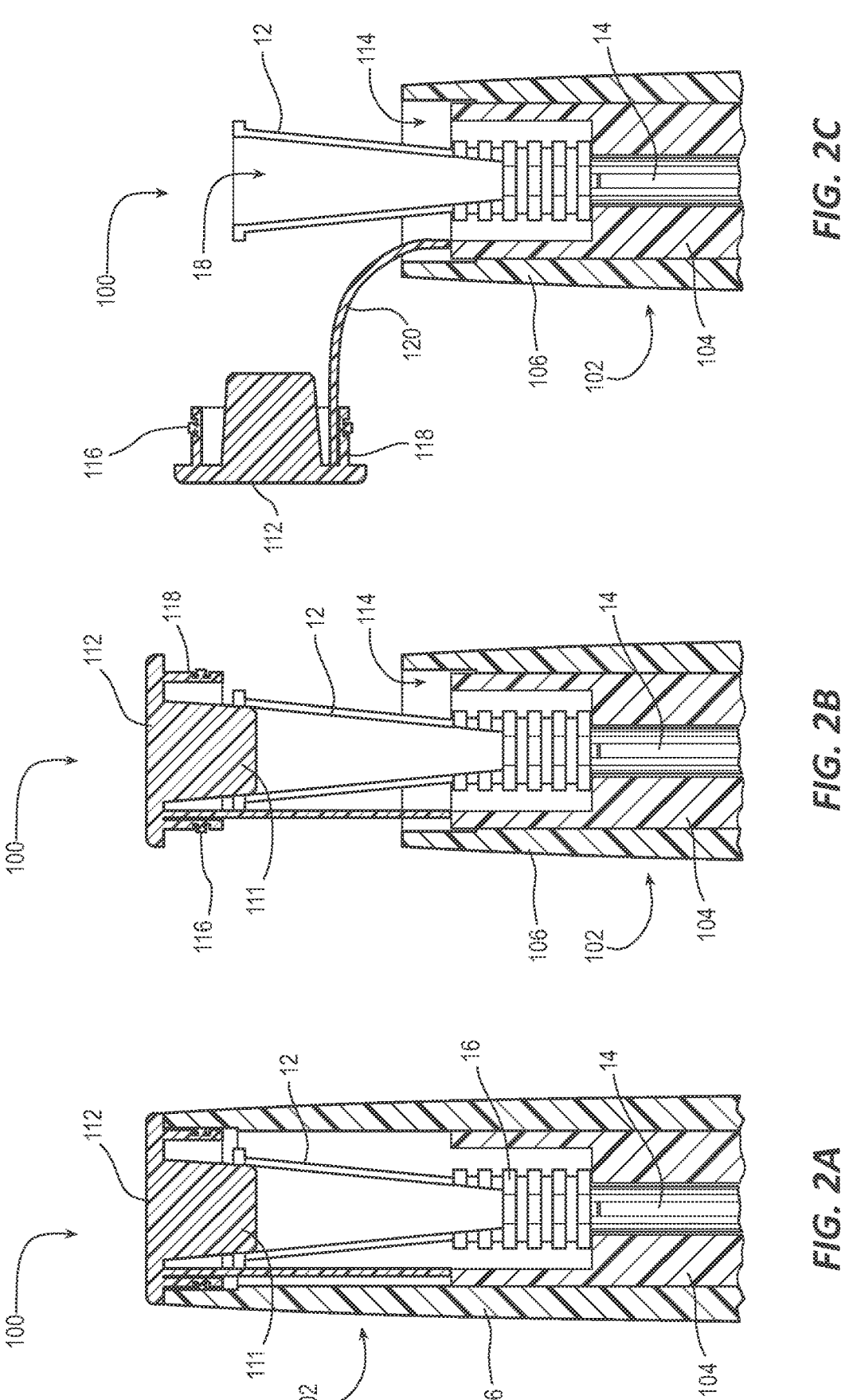
FIG. 2A illustrates a cross section of the first intermittent-catheter assembly of FIG. 1A in accordance with some embodiments.
FIG. 2B illustrates a cross section of the first intermittent-catheter assembly of FIG. 1B in accordance with some embodiments.
FIG. 2C illustrates a cross section of the first intermittent-catheter assembly of FIG. 1C in accordance with some embodiments.
Figure 4:
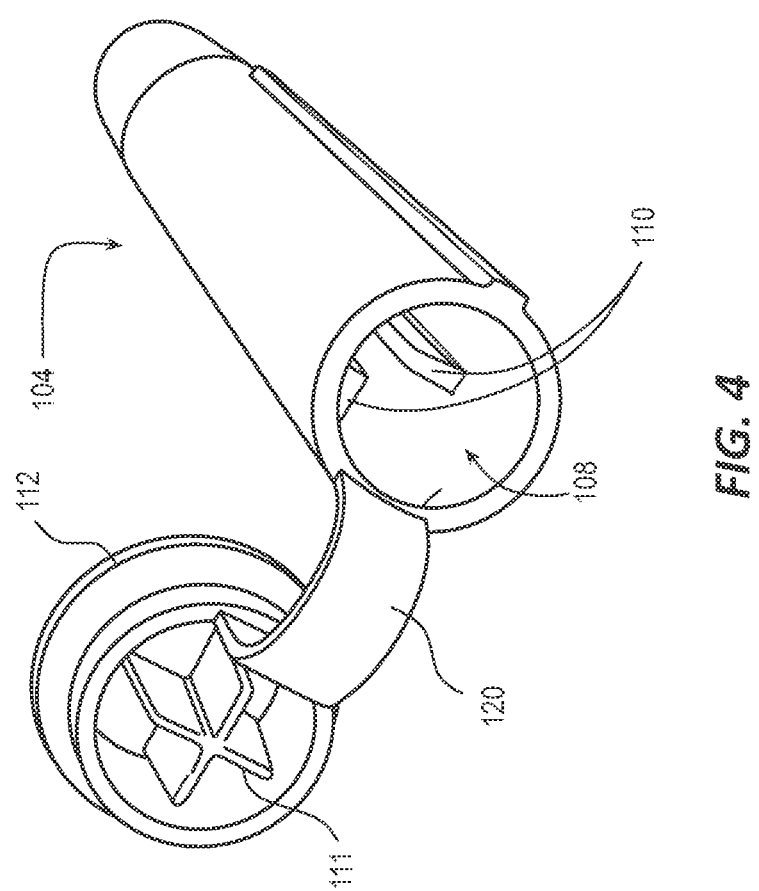
FIG. 4 illustrates a perspective view of the catheter housing in accordance with some embodiments.
Figure 3:
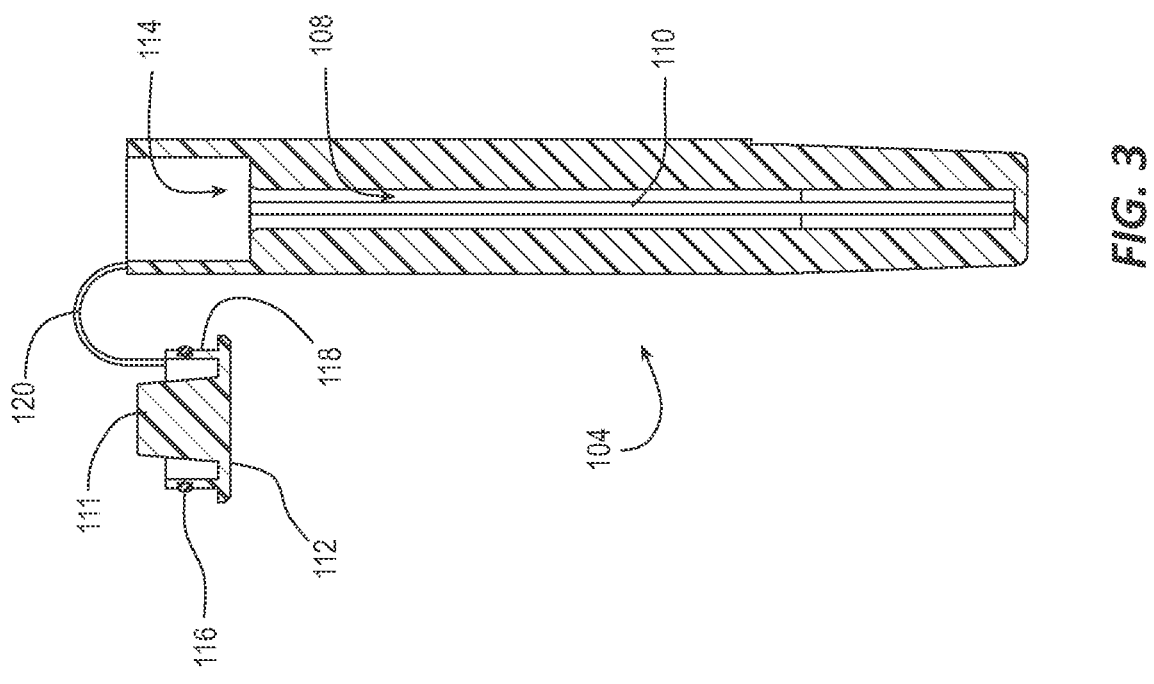
FIG. 3 illustrates a longitudinal cross section of the catheter housing in accordance with some embodiments.

FIG. 3 illustrates a longitudinal cross section of the catheter housing 102 in accordance with some embodiments. FIG. 4 illustrates a perspective view of the catheter housing 102 in accordance with some embodiments.

As shown by the longitudinal cross section of the catheter housing 102, the inner sleeve 104, 204, 304, or 404 can include longitudinal ribs 110 such as those shown for the inner sleeve 104 extending into the cavity 108. When present, the ribs 110 stabilize the intermittent catheter 10 in the inner sleeve 104, 204, 304, or 404 in the packaged state of the intermittent-catheter assembly 100, 200, 300, or 400.

In addition to the ribs 110, at least the cap 112 or 212 set forth below can include a funnel insert 111 along a centerline of the cap 112 or 212 as shown in FIGS. 3 and 4 for the catheter housing 102. Indeed, the funnel insert 111 is shown inboard of the rim 118 of the cap 112. When present, the funnel insert 111 is inserted into the funnel 12 of the intermittent catheter 10 in the packaged state of the inter-mittent-catheter assembly 100 or 200, which stabilizes the intermittent catheter 10 in the inner sleeve 104 or 204.

To reduce redundancy in description set forth herein, the ribs 110, the funnel insert 111, or both the ribs 110 and the funnel insert 111 can be incorporated into any intermittent-catheter assembly of those set forth herein to the same effect as the foregoing. This is with the understanding that certain modifications within the skill of a person of ordinary skill in the art might need to be made to the intermittent-catheter assembly to which the ribs 110 or the funnel insert 111 is added.

Adverting to the intermittent-catheter assemblies 100 and 200, the inner sleeve 104 or 204 includes a displaceable cap 112 or 212 sealing an opening of the outer sleeve 106 or 206 opposite the exposed end of the inner sleeve 104 or 204 in the packaged state of the intermittent-catheter assembly 100 or 200. Indeed, the cap 112 or 212 seals the opening of the outer sleeve 106 or 206 and maintains sterility of the intermittent catheter 10 in the packaged state of the inter-mittent-catheter assembly 100 or 200.

The cap 112 or 212 sits in a seat 114 or 214 formed within the opening of the outer sleeve 106 or 206. As shown for the catheter housing 102, the cap 112 or 212 can include an annular gasket 116 such as that disposed in a recess around a rim 118 of the cap 112. When present, the gasket 116 sits between the cap 112 or 212 and the outer sleeve 106 or 206 securing and sealing the cap 112 or 212 in the outer sleeve 106 or 206 in the packaged state of the intermittent-catheter assembly 100 or 200.

Figure 6B:
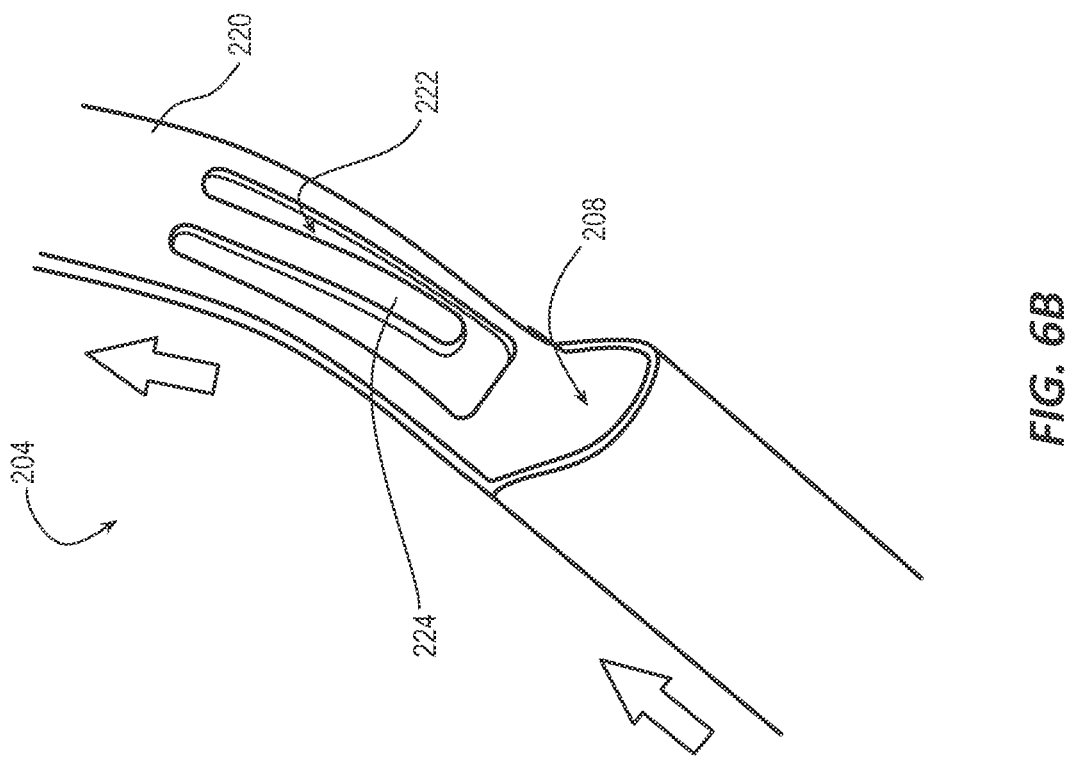
FIG. 6B illustrates the tether bending away from a centerline of the catheter housing in accordance with some embodiments.
Figure 6A:
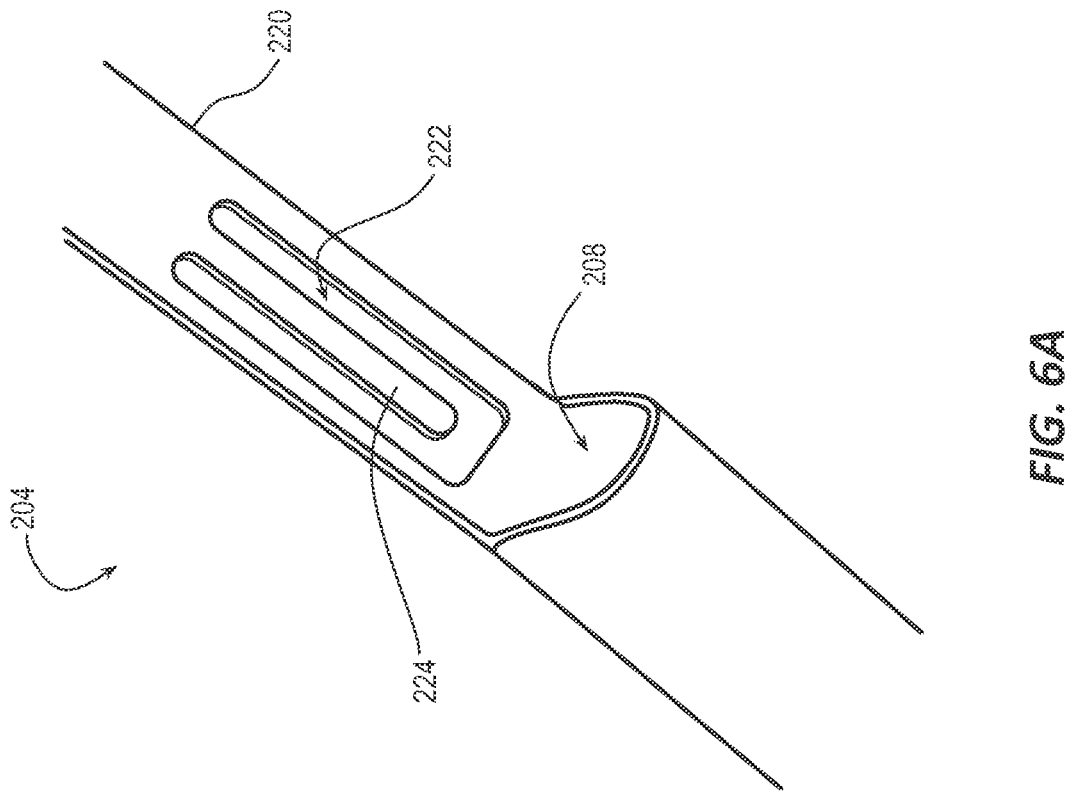
FIG. 6A illustrates a tether of the second intermittent-catheter assembly in accordance with some embodiments.

FIG. 6A illustrates a tether 220 of the catheter housing 202 in accordance with some embodiments. FIG. 6B illus-trates the tether 220 bending away from a centerline of the catheter housing 202 in accordance with some embodi-ments.

As shown in FIGS. 1C, 2C, 3, and 4 for the catheter housing 102 and FIGS. 5B, 5C, 6A, and 6B for the catheter housing 202, the cap 112 or 212 can be tethered to the inner sleeve 104 or 204 by the tether 120 or 220 to keep the cap 112 or 212 with the catheter housing 102 or 202. Upon grasping the outer sleeve 106 or 206 and sliding the outer sleeve 106 or 206 toward the exposed end of the inner sleeve 104 or 204 in opposition to a force (e.g., a normal force $F_n$) applied to the exposed end of the inner sleeve 104 or 204, the cap 112 or 212 pops open to expose the funnel 12 of the intermittent catheter 10 but remains attached to the inner sleeve 104 or 204 by the tether 120 or 220.

The tether 120 or 220 can be a polymeric wire or ribbon. As to the tether 220, the tether 220 is shown in FIGS. 6A and 6B as a ribbon with an opening 222 configured to weaken a structural integrity of the tether 220 around the opening 222 such that the tether 220 and the cap 212 tethered thereto bend away from a centerline of the catheter housing 202 as the outer sleeve 206 is slid toward the exposed end of the inner sleeve 204. So configured, the tether 220 facilitates access to the intermittent catheter 10 once exposed. In addition, the opening 222 can include a tongue 224 in about a same plane or surface as the opening 222, which tongue can be used like a belt clip to suspend the intermittent-catheter assembly 200. Likewise, the tether 120 can include such an opening an optional tongue.

Adverting to the intermittent-catheter assembly 300, the outer sleeve 306 includes a displaceable cap 312 sealing an opening of the outer sleeve 306 opposite the exposed end of the inner sleeve 304 in the packaged state of the intermittent-catheter assembly 300. Indeed, the cap 312 seals the opening of the outer sleeve 306 and maintains sterility of the inter-mittent catheter 10 in the packaged state of the intermittent-catheter assembly 300.

The cap 312 sits on a seat 314 formed around the opening of the outer sleeve 306 in the packaged state of the inter-mittent-catheter assembly 300. As shown, the cap 312 and the outer sleeve 306 can include complementary snap-fit features. When present, the complementary snap-fit features secure the cap 312 on the outer sleeve 306 in the packaged state of the intermittent-catheter assembly 300.

As best shown in FIG. 8, the cap 312 can be coupled to the outer sleeve 306 by a living hinge 320 to keep the cap 312 with the catheter housing 302. Upon grasping the outer sleeve 306 and sliding the outer sleeve 306 toward the exposed end of the inner sleeve 304 in opposition to a force (e.g., a normal force $F_n$) applied to the exposed end of the inner sleeve 304, the cap 312 pops open to expose the funnel 12 of the intermittent catheter 10 but remains attached to the outer sleeve 306 by the living hinge 320.

FIG. 14 illustrates the inner sleeve 404 and the outer sleeve 406 of the catheter housing 402 separated from each other in accordance with some embodiments.

Adverting to the intermittent-catheter assembly 400, the inner sleeve 404 includes an end cap 412 integrated into the inner sleeve 404. Indeed, the inner sleeve 404 includes a longitudinal side opening 426 to the longitudinal cavity 408 with the end cap 412 integrated into the inner sleeve 404 on an end of the side opening 426 opposite the exposed end of the inner sleeve 404 in the packaged state of the intermittent-catheter assembly 300.

FIG. 15A illustrates a connecting portion 428 of the inner sleeve 404 disposed in the catheter housing 402 in accor-dance with some embodiments, and FIGS. 15B and 15C illustrate the connecting portion 428 of the inner sleeve bending away from a centerline of the catheter housing 402 in accordance with some embodiments.

As shown, the connecting portion 428 of the inner sleeve 404 is coterminous with ends of the side opening 426. The connecting portion 428 is molded with a bias such that the connecting portion 428 and the end cap 412 coupled thereto bend away from the centerline of the catheter housing 402 as the outer sleeve 406 is slid toward the exposed end of the inner sleeve 404. So configured, the connecting portion 428 facilitates access to the intermittent catheter 10. Indeed, upon grasping the outer sleeve 406 and sliding the outer sleeve 406 toward the exposed end of the inner sleeve 404 in opposition to a force (e.g., a normal force $F_n$) applied to the exposed end of the inner sleeve 404, the connecting portion 428 bends away from the centerline of the catheter housing 402 and the funnel 12 of the intermittent catheter 10.

As shown in FIGS. 5C and 13C by the intermittent-catheter assemblies 200 and 400, the intermittent-catheter assembly 100, 200, 300, or 400 can include a drainage bag 22. The drainage bag 22 is fluidly coupled to the funnel 12 for voiding urine into the drainage bag 22 upon catheter-ization with the intermittent catheter 10.

To reduce redundancy in description set forth herein, the drainage bag can be incorporated into any intermittent-catheter assembly of those set forth herein to the same effect as the foregoing. This is with the understanding that certain modifications within the skill of a person of ordinary skill in the art might need to be made to the intermittent-catheter assembly to which the drainage bag 22 is added.

FIGS. 16A-16C illustrate a fifth intermittent-catheter assembly 500 in different states in accordance with some embodiments.

As shown, the intermittent-catheter assembly 500 includes the intermittent catheter 10 and a catheter housing 502. The intermittent catheter 10 is disposed in the catheter housing 502 while in a packaged state of the intermittent-catheter assembly 500 for maintaining sterility of the intermittent catheter 10.

The catheter housing 502 includes a sleeve 503 and a cap 512 for sealing an opening of the sleeve 503 opposite a closed end of the sleeve 503. Indeed, the cap 512 seals the opening of the sleeve 503 and maintains sterility of the intermittent catheter 10 in the packaged state of the intermittent-catheter assembly 500.

The sleeve 503 includes a longitudinal cavity 508 containing a majority of the intermittent catheter 10 in the packaged state of the intermittent-catheter assembly 500. The cavity 508 is accessible by way of a longitudinal extension 526 of the opening into the sleeve 503. The extension 526 into the sleeve 503 is configured to expose a longitudinal portion of the funnel 12 when the cap 512 is moved from a closed position in the packaged state of the intermittent-catheter assembly to an open position such as the open position of the cap 512 about the living hinge 520 set forth below.

The cap 512 can be coupled to the sleeve 503 by a living hinge 520 to keep the cap 512 with the catheter housing 502. (See FIGS. 17 and 18.) As set forth below, the cap 512 can alternatively be any cap of the those set forth in FIGS. 16A-16C and 17-19, which might require certain modifications to the sleeve 503 as well.

FIG. 17 illustrates the cap 512 including a pull tab 530 in accordance with some embodiments. In consideration of the cap 512 of FIGS. 16A and 16B having a first form factor, FIG. 17 illustrates a second form factor for the cap 512 of the intermittent-catheter assembly 500 in accordance with some embodiments. Indeed, the second form factor of the cap 512 does not extend into a longitudinal extension of the opening of the sleeve 503. That, and the second form factor of the cap 512 develops a longer lever arm than the first form factor of the cap 512 when the pull tab 530 is pulled away from the cap 512 as set forth below.

As shown, the cap 512 of FIGS. 16A, 16B, and 17 includes the pull tab 530 coupled to the cap 512 on a same side of the catheter housing 502 as the living hinge 520. A portion of the pull tab 530 is configured to peel away from the cap 512 toward an opposite side of the catheter housing 502 from the living hinge 520 when the pull tab 530 is initially pulled to extend a lever arm $\ell$ with respect to the living hinge 520 from an initial lever arm $\ell_i$ to a final lever arm $\ell_f$ sufficient for subsequently pulling the cap 512 away from the opening of the sleeve 503 by the pull tab 530. Advantageously, when the pull tab 530 is intact (i.e., not pulled toward the opposite side of the catheter housing 502), the pull tab 530 indicates the intermittent-catheter assembly 500 has not been opened or tampered with by another party.

FIG. 18 illustrates the cap 512 including a push tab 532 in accordance with some embodiments.

As shown, the cap 512 of FIG. 18 includes the push tab 532 extending from an opposite side of the catheter housing 502 from the living hinge 520. The push tab 532 is configured to extend the lever arm e with respect to the living hinge 520 over that of the cap 512 without the push tab 532 such that the lever arm e is sufficient for pushing the cap 512 away from the opening of the sleeve 503 by the push tab 532.

FIG. 19 illustrates the cap 512 including a push button 534 in accordance with some embodiments.

As shown, the cap 512 of FIG. 19 includes the push button 534 on an opposite side of the catheter housing 502 from the living hinge 520. The push button 534 is configured to deform the cap 512 and disengage complementary snap-fit features between the cap 512 and the sleeve 503 for subsequently pushing the cap 512 away from the opening of the sleeve 503 by the push button 534.

To reduce redundancy in description set forth herein, the cap 512 set forth in any figure of FIGS. 16A-16C and 17-19 can be incorporated into any intermittent-catheter assembly of those set forth herein to the same effect as the foregoing. This is with the understanding that certain modifications within the skill of a person of ordinary skill in the art might need to be made to the intermittent-catheter assembly to which the cap 512 is added.

As shown in FIG. 16C, the intermittent-catheter assembly 500 can include the drainage bag 22. The drainage bag 22 is fluidly coupled to the funnel 12 for voiding urine into the drainage bag 22 upon catheterization with the intermittent catheter 10.

FIG. 20 illustrates a sixth intermittent-catheter assembly 600 in a packaged state of the intermittent-catheter assembly 600 in accordance with some embodiments. FIG. 21 illustrates a sleeve 603, a removable cap 612, and shrink-wrap packaging 636 of the intermittent-catheter assembly 600 of FIG. 20 separated from each other in accordance with some embodiments. FIGS. 22 and 23 illustrate the same intermittent-catheter assembly 600 albeit with an elongated form factor for inclusion of the drainage bag 22.

As shown, the intermittent-catheter assembly 600 includes the intermittent catheter 10 and a catheter housing 602. The intermittent catheter 10 is disposed in the catheter housing 602 while in the packaged state of the intermittent-catheter assembly 600 for maintaining sterility of the intermittent catheter 10.

The catheter housing 602 includes the sleeve 603 and the cap 612 for sealing an opening of the sleeve 603 opposite a closed end of the sleeve 603. Indeed, the cap 612 seals the opening of the sleeve 603 and maintains sterility of the intermittent catheter 10 in the packaged state of the intermittent-catheter assembly 600.

The sleeve 603 includes a longitudinal cavity 608 containing a majority of the intermittent catheter 10 in the packaged state of the intermittent-catheter assembly 600. The sleeve 603 including the cavity 608 thereof is approximately coextensive with the catheter tube 14 of the intermittent catheter 10.

While not shown, the sleeve 603 can include the ribs 110 extending into the cavity 108. When present, the ribs 110 stabilize the intermittent catheter 10 in the sleeve 603 in the packaged state of the intermittent-catheter assembly 600.

The cap 612 includes another longitudinal cavity 609 configured to contain a remainder of the intermittent catheter 10. The cap 612 including the cavity 609 thereof is approximately coextensive with the funnel 12 of the intermittent catheter 10.

The sleeve 603 and the cap 612 can include complementary snap-fit features. When present, the complementary snap-fit features secure the cap 612 on the sleeve 603 in the packaged state of the intermittent-catheter assembly 600. In addition, the cap 612 can be configured to deform when squeezed. When the cap 612 is squeezed and deformed, the snap-fit features of the cap 612 disengage from those of the sleeve 603 for subsequently removing the cap 612. As set forth below, the cap 612 can be any cap of the those set forth in FIGS. 24-26, which might require certain modifications to the sleeve 603 as well.

FIG. 24 illustrates the cap 612 including longitudinal recesses 638 around an outside of the cap 612 in accordance with some embodiments. FIG. 25 illustrates the cap 612 including longitudinal ribs 640 around the outside of the cap 612 in accordance with some embodiments.

While not shown, the cap 612 of FIGS. 24 and 25 includes internal threads about an open-ended portion of the cap 612. In addition, the sleeve 603 includes complementary external threads about an open-ended portion of the sleeve 603 terminating with the opening of the sleeve 603. The recesses 638 or the ribs 640 around the outside of the cap 612 are configured to facilitate gripping the cap 612 and screwing the cap 612 off of the sleeve 603 or onto the sleeve 603.

FIG. 26 illustrates the cap 612 including a pull tab 630 in accordance with some embodiments.

As shown, the cap 612 of FIG. 26 includes a circumferential weakened area 613 (e.g., a spiral perforation) around the cap 612, which can be a portion of the sleeve 603 opposite the closed end of the sleeve 603. The pull tab 630 is configured for gripping the cap 612 and tearing the cap 612 away from the sleeve 603. Advantageously, when the cap 612 is intact (i.e., not torn away from the sleeve 603), the cap 612 indicates the intermittent-catheter assembly 600 has not been opened or tampered with by another party.

To reduce redundancy in description set forth herein, the cap 612 set forth in any figure of FIGS. 20-26 can be incorporated into any intermittent-catheter assembly of those set forth herein to the same effect as the foregoing. This is with the understanding that certain modifications within the skill of a person of ordinary skill in the art might need to be made to the intermittent-catheter assembly to which the cap 612 is added.

The packaging 636 is over the entirety of the cap 612 and at least a portion of the sleeve 603 in at least the embodiments of the intermittent-catheter assembly 600 shown in FIGS. 20-23. The packaging 636 includes a pull tab 631 extending from the packaging 636 configured to break open the packaging 636 when the pull tab 631 is pulled.

As shown in FIG. 23, the intermittent-catheter assembly 600 can include the drainage bag 22. The drainage bag 22 is fluidly coupled to the funnel 12 for voiding urine into the drainage bag 22 upon catheterization with the intermittent catheter 10.

FIGS. 27A and 27B illustrate a seventh intermittent-catheter assembly 700 in different states of the intermittent-catheter assembly 700 in accordance with some embodiments. FIG. 28 illustrates a sleeve 706, a reinforcing insert 704, and an adhesive tab 712 of the intermittent-catheter assembly 700 of FIGS. 27A and 27B separated from each other in accordance with some embodiments. FIGS. 28A, 28B, and 29 illustrate the same intermittent-catheter assembly 700 albeit with an elongated form factor for inclusion of the drainage bag 22.

As shown, the intermittent-catheter assembly 700 includes the intermittent catheter 10 and a catheter housing 702. The intermittent catheter 10 is disposed in the catheter housing 702 while in a packaged state of the intermittent-catheter assembly 700 for maintaining sterility of the intermittent catheter.

The sleeve 706 includes a longitudinal cavity 708 containing a majority of the intermittent catheter 10 up to an entirety of the intermittent catheter 10 in the packaged state of the intermittent-catheter assembly 700. The sleeve 706 also includes a longitudinal sleeve gap 726 in major sides (e.g., a front and a back) of the sleeve 706 configured to provide access to the intermittent catheter 10 as set forth below.

The reinforcing insert 704 includes a longitudinal cavity 709 containing a portion (e.g., the funnel 12) of the intermittent catheter 10 in the packaged state of the intermittent-catheter assembly 700. The reinforcing insert 704 includes a longitudinal insert gap 727 and major-side protrusions 742, minor-side protrusions 744, or both the major-side protrusions 742 and the minor-side protrusions 744. The major-side and minor-side protrusions 742 and 744 are configured to suspend the reinforcing insert 704 in the sleeve gap 726 of the sleeve 706 such that the sleeve gap 726 and the insert gap 727 combine to provide major-side openings in the catheter housing 702 for grasping the funnel 12 and removing the intermittent catheter 10 from the catheter housing after the adhesive tab 712 is removed.

The adhesive tab 712 covers the major-side openings of the catheter housing 702 in the packaged state of the intermittent-catheter assembly 700. The adhesive tab 712 includes a pull tab 730 extending from the adhesive tab 712 configured to peel the adhesive tab 712 away from the major-side openings of the catheter housing 702 when the pull tab 730 is pulled.

As shown in FIG. 29B, the intermittent-catheter assembly 700 can include the drainage bag 22. The drainage bag 22 is fluidly coupled to the funnel 12 for voiding urine into the drainage bag 22 upon catheterization with the intermittent catheter 10. Notably, the reinforcing insert 704 includes the minor-side protrusions 744 to lengthen the catheter housing 702 for accommodating the drainage bag 22 in the elongated form factor of the intermittent-catheter assembly 700 of FIGS. 29A, 29B, and 30.

FIGS. 31A and 31B illustrate an eighth intermittent-catheter assembly 800 in different states of the intermittent-catheter assembly 800 in accordance with some embodiments. FIGS. 32A and 32B illustrate the same intermittent-catheter assembly 800 albeit with an elongated form factor for inclusion of the drainage bag 22. FIG. 33 illustrates a ninth intermittent-catheter assembly 900 in a packaged state of the intermittent-catheter assembly 900 in accordance with some embodiments.

As shown, the intermittent-catheter assembly 800 or 900 includes the intermittent catheter 10 and a catheter housing 802 or 902. The intermittent catheter 10 is disposed in the catheter housing 802 or 902 while in a packaged state of the intermittent-catheter assembly 800 or 900 for maintaining sterility of the intermittent catheter 10. The catheter tube 14 of the intermittent catheter 10 is exposed with the collapsible sheath 803 or 903 set forth below cinched up to the funnel 12 of the intermittent catheter 10 while in ready-to-used state of the intermittent-catheter assembly 800 or 900.

The catheter housing 802 or 902 includes at least a collapsible sheath 803 or 903 and a pull tab 831 or 931, which pull tab 831 or 931 may instead be considered packaging of the intermittent-catheter assembly 800 or 900 in the packaged state of the intermittent-catheter assembly 800 or 900. As to the intermittent-catheter assembly 800, the catheter housing 802 also includes an end piece 846 around the catheter tube 14 of the intermittent catheter 10 and a removable cap 812 sealing a proximal opening of the funnel 12 of the intermittent catheter 10 in the packaged state of the intermittent-catheter assembly 800. An end piece such as the end piece 846 is optional in the intermittent-catheter assembly 900. Also, instead of the removable cap 812 or the like, the intermittent-catheter assembly 900 includes another pull tab 930 for sealing the proximal opening of the funnel 12 and maintaining sterility of the intermittent catheter 10 in the packaged state of the intermittent-catheter assembly 900.

The collapsible sheath 803 or 903 includes a proximal portion coupled to the funnel 12 of the intermittent catheter 10. A distal portion of the collapsible sheath 803 is coupled to the end piece 846, which end piece, in turn, includes a distal opening sealed by the pull tab 831 in the packaged state of the intermittent-catheter assembly 800. In intermittent-catheter assemblies without an end piece such as the intermittent-catheter assembly 900 shown in FIG. 33, a distal opening of the collapsible sheath 903 is sealed by the pull tab 931 in the packaged state of the intermittent-catheter assembly 900. An entirety of the catheter tube 14 of the intermittent catheter 10 is disposed in the collapsible sheath 803 or 903 in the packaged state of the intermittent-catheter assembly 800 or 900, thereby maintaining sterility of the intermittent catheter 10.

As shown in FIG. 32B, the intermittent-catheter assembly 800 can include the drainage bag 22. The drainage bag 22 is fluidly coupled to the funnel 12 for voiding urine into the drainage bag 22 upon catheterization with the intermittent catheter 10. Notably, the cap 812 has a greater length in the intermittent-catheter assembly 800 of FIGS. 32A and 32B than in the intermittent-catheter assembly 800 of FIGS. 31A and 31B to accommodate the drainage bag 22.

FIG. 34 illustrates a tenth intermittent-catheter assembly 1000 in a packaged state of the intermittent-catheter assembly 1000 in accordance with some embodiments.

As shown, the intermittent-catheter assembly 1000 includes the intermittent catheter 10 and a catheter housing 1002. The intermittent catheter 10 is disposed in the catheter housing 1002 while in the packaged state of the intermittent-catheter assembly 1000 for maintaining sterility of the intermittent catheter 10.

The catheter housing 1002 includes a bottle 1003. An entirety of the catheter tube 14 of the intermittent catheter 10 is disposed in the bottle 1003 with at least a portion of the funnel 12 of the intermittent catheter 10 fitted into a neck 1048 of the bottle 1003 in the packaged state of the intermittent-catheter assembly 1000. A proximal opening of the funnel 12 and a proximal opening of the bottle 1003 or the neck 1048 can be concentric in the packaged state of the intermittent-catheter assembly 1000. An inner diameter of the neck 1048 can be larger than an outer diameter of the funnel 12, thereby configuring the bottle 1003 to be fluidly coupled to the funnel 12 for voiding urine into the bottle 1003 upon catheterization with the intermittent catheter 10. Optionally, the funnel 12 can include a longitudinal channel or notch along a side thereof allowing therethrough an exchange of air in the bottle for urine voided from a bladder, particularly if the inner diameter of the neck 1048 is commensurate with the outer diameter of the funnel 12 and otherwise restricts fluid exchange.

A pull tab 1030 seals the intermittent catheter 10 in the bottle 1003 in the packaged state of the intermittent-catheter assembly 1000. When the proximal opening of the funnel 12 and the proximal opening of the bottle 1003 or neck 1048 are concentric, the pull tab 1030 simultaneously seals the funnel 12 and the bottle 1003 in the packaged state of the intermittent-catheter assembly 1000.

FIG. 35 and FIG. 36 respectively illustrate a bottom suction cup 148 and a side suction cup 150 for any intermittent-catheter assembly of those set forth herein. Such suction cups can be incorporated into a catheter housing (e.g., a sleeve or a cap) of an intermittent-catheter assembly for sticking the intermittent-catheter assembly or the catheter housing thereof to a surface (e.g., bathroom stall divider or door, top of a toilet, etc.) when desired or needed during catheterization. Such suction cups are particular useful for maintaining sterility in tight spaces such as bathroom stalls where available surface are limited or of questionable cleanliness.

Methods

Methods of intermittent-catheter assemblies such as those set forth above include methods of using them. For example, a method of using any intermittent-catheter assembly of those set forth above includes one or more steps selected from a catheter assembly-obtaining step, an intermittent catheter-exposing step, an intermittent catheter-removing step, a catheter tube-inserting step, and a urine-voiding step.

For expository expediency, the foregoing steps are set forth in detail below with respect to the intermittent-catheter assemblies 100 and 800. However, the steps detailed below are set forth with the understanding that the steps can be practiced with other intermittent-catheter assemblies set forth above, albeit with certain modifications in view of the different configurations of the intermittent-catheter assemblies. As to such modifications, it should be understood that the intermittent-catheter assemblies or components thereof set forth above "configured to" or "configured for" effectuating some action often employ a user to effectuate that action.

The catheter assembly-obtaining step includes obtaining the intermittent-catheter assembly 100 or 800 in the packaged state of the intermittent-catheter assembly 100 or 800. The intermittent-catheter assembly 100 or 800 has the intermittent catheter 10 disposed in the catheter housing 102 or 802 in the packaged state of the intermittent-catheter assembly 100 or 800.

The intermittent catheter-exposing step depends upon the configuration of the intermittent-catheter assembly 100 or 800 used in practicing the method.

With respect to the intermittent-catheter assembly 100, the intermittent catheter-exposing step includes exposing the intermittent catheter 10 for removal from the catheter housing 102, which includes an outer sleeve-grasping step, a force-applying step, and an outer sleeve-sliding step. The outer sleeve-grasping step includes grasping the outer sleeve 106 of the catheter housing 102. The force-applying step includes applying a force to the exposed end of the inner sleeve 104 of the catheter housing 102. The outer sleeve-sliding step includes sliding the outer sleeve 106 toward the exposed end of the inner sleeve 104 in opposition to the force applied to the exposed end of the inner sleeve 104.

With respect to the intermittent-catheter assembly 800, the intermittent catheter-exposing step includes exposing the intermittent catheter 10 for insertion into a urethra, which includes a pull tab-removing step, an end piece-grasping step, and an end piece-sliding step. The pull tab-removing step includes removing the pull tab 831 sealing the distal opening of the end piece 846 of the catheter housing 802. The end piece-grasping step includes grasping the end piece 846. The end piece-sliding step includes proximally sliding the end piece 846 over the catheter tube 14 of the intermittent catheter 10 toward the funnel 12 of the intermittent catheter 10.

The intermittent catheter-removing step includes removing the intermittent catheter 10 from the catheter housing 102 or 802 after the intermittent catheter-exposing step. However, the intermittent catheter 10 of FIG. 32A need not be removed from the catheter housing 802.

The catheter tube-inserting step includes inserting the catheter tube 14 of the intermittent catheter 10 into a urethra.

The urine-voiding step includes voiding urine from a bladder with the intermittent catheter 10.

The method can further include a catheter tube-removing step and a catheter assembly-disposing step. The catheter tube-removing step includes removing the catheter tube 14 from the urethra after the urine-voiding step. The catheter assembly-disposing step includes disposing of the intermittent catheter 10 and the catheter housing 102 or 802. Optionally, the intermittent catheter 10 and the catheter housing 802 are disposed of in a reassembled state or partially reassembled state of the intermittent-catheter assembly 100 or 800 during the catheter assembly-disposing step.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An intermittent-catheter assembly, comprising:
an intermittent catheter including:
a funnel; and
a catheter tube fluidly coupled to the funnel; and
a catheter housing including the intermittent catheter disposed in the catheter housing in a packaged state of the intermittent-catheter assembly, the catheter housing including:
an inner sleeve including a longitudinal cavity containing a majority of the intermittent catheter in the packaged state of the intermittent-catheter assembly;
an outer sleeve slidably disposed over the inner sleeve but exposing an exposed end of the inner sleeve; and
a cap sealing an opening of the outer sleeve opposite the exposed end of the inner sleeve for maintaining sterility in the packaged state of the intermittent-catheter assembly or disposing the intermittent-catheter assembly in a reassembled state of the intermittent-catheter assembly,
the catheter housing configured to expose the intermittent catheter for removal from the catheter housing when the outer sleeve is grasped and slid toward the exposed end of the inner sleeve in opposition to a force applied to the exposed end of the inner sleeve.

2. The intermittent-catheter assembly of claim 1, wherein the inner sleeve includes longitudinal ribs extending into the longitudinal cavity, the longitudinal ribs stabilizing the intermittent catheter in the inner sleeve in the packaged state of the intermittent-catheter assembly.

3. The intermittent-catheter assembly of claim 1, wherein the cap sits in a seat formed within the opening of the outer sleeve, the cap tethered to the inner sleeve by a tether.

4. The intermittent-catheter assembly of claim 3, wherein the tether is a polymeric ribbon including an opening configured to weaken a structural integrity of the polymeric ribbon around the opening such that the polymeric ribbon and the cap tethered thereto bend away from a centerline of the catheter housing as the outer sleeve is slid toward the exposed end of the inner sleeve, thereby facilitating access to the intermittent catheter.

5. The intermittent-catheter assembly of claim 1, wherein the cap includes an annular gasket disposed in a recess around a rim of the cap, the annular gasket sitting between the cap and the outer sleeve securing the cap in the outer sleeve in the packaged state of the intermittent-catheter assembly.

6. The intermittent-catheter assembly of claim 5, wherein the cap includes a funnel insert along a centerline of the cap, the funnel insert inserted into the funnel of the intermittent catheter stabilizing the intermittent catheter in the inner sleeve in the packaged state of the intermittent-catheter assembly.

7. The intermittent-catheter assembly of claim 1, wherein the cap sits on a seat formed around the opening of the outer sleeve in the packaged state of the intermittent-catheter assembly, the cap coupled to the outer sleeve by a living hinge.

8. The intermittent-catheter assembly of claim 7, wherein the cap and the outer sleeve include complementary snap-fit features securing the cap on the outer sleeve in the packaged state of the intermittent-catheter assembly.

9. The intermittent-catheter assembly of claim 1, wherein the inner sleeve includes a longitudinal side opening to the longitudinal cavity, the inner sleeve including the cap integrated into the inner sleeve opposite the exposed end of the inner sleeve.

10. The intermittent-catheter assembly of claim 9, wherein a connecting portion of the inner sleeve coterminous with ends of the longitudinal side opening is molded with a bias such that the connecting portion and the cap coupled thereto bend away from a centerline of the catheter housing as the outer sleeve is slid toward the exposed end of the inner sleeve, thereby facilitating access to the intermittent catheter.

11. The intermittent-catheter assembly of claim 1, further comprising a drainage bag fluidly coupled to the funnel for voiding urine into the drainage bag upon catheterization with the intermittent catheter.

* * * * *